US010485857B2

(12) United States Patent
Fischer et al.

(10) Patent No.: US 10,485,857 B2
(45) Date of Patent: Nov. 26, 2019

(54) HEARTWORM VACCINE, METHODS AND USES THEREOF

(71) Applicant: BOEHRINGER INGELHEIM ANIMAL HEALTH USA INC., Duluth, GA (US)

(72) Inventors: Laurent Fischer, Sainte Foy les Lyon (FR); Yovany Moreno, Alpharetta, GA (US); Cecile Sigoillot-Claude, Ouillins (FR); Frederic Beugnet, Thurins (FR)

(73) Assignee: BOEHRINGER INGELHEIM ANIMAL HEALTH USA INC., Duluth, GA (US)

( * ) Notice: Subject to any disclaimer, the term of this patent is extended or adjusted under 35 U.S.C. 154(b) by 0 days.

(21) Appl. No.: 15/480,345

(22) Filed: Apr. 5, 2017

(65) Prior Publication Data

US 2017/0290895 A1 Oct. 12, 2017

Related U.S. Application Data

(60) Provisional application No. 62/319,731, filed on Apr. 7, 2016, provisional application No. 62/423,174, filed on Nov. 16, 2016.

(51) Int. Cl.

| | |
|---|---|
| ***A61K 39/00*** | (2006.01) |
| ***C07H 21/04*** | (2006.01) |
| ***A61K 39/002*** | (2006.01) |
| ***C07K 16/20*** | (2006.01) |
| ***A61K 39/02*** | (2006.01) |
| ***C07K 14/435*** | (2006.01) |

(52) U.S. Cl.
CPC ...... *A61K 39/0003* (2013.01); *A61K 39/0233* (2013.01); *C07K 14/4354* (2013.01); *C07K 16/20* (2013.01); *C07K 14/43536* (2013.01)

(58) Field of Classification Search
CPC .............................. A61K 39/00; A61K 39/002
USPC ............................... 424/184.1, 185.1, 265.1
See application file for complete search history.

(56) References Cited

U.S. PATENT DOCUMENTS

| | | | |
|---|---|---|---|
| 4,761,281 | A | 8/1988 | Scherr |
| 4,842,999 | A | 6/1989 | Fuller et al. |
| 5,492,695 | A | 2/1996 | Grieve et al. |
| 5,744,593 | A | 4/1998 | Klimowski et al. |
| 5,750,393 | A | 5/1998 | Tripp et al. |
| 2002/0086974 | A1 | 7/2002 | Tripp et al. |
| 2013/0236490 | A1 | 9/2013 | Kalyanasundaram |
| 2017/0051024 | A1 | 2/2017 | Makepeace et al. |

FOREIGN PATENT DOCUMENTS

| | | |
|---|---|---|
| WO | WO 1993/010225 | 5/1993 |
| WO | WO 2015/121646 | 8/2015 |

OTHER PUBLICATIONS

McGonigle et al. Immunisation of mice with fractions derived from the intestines of Dirofilaria immitis. International Journal for Parasitology 31 (2001) 1459-1466.

Bennuru. Understanding Hidden Antigens and Targeting Parasitic Nematodes. EBioMedicine 2 (2015) 1010-1011.

Fu et al., Novel Insights into the Transcriptome of *Dirofilaria immitis* Jul. 2012 | vol. 7 | Issue 7 | e41639.

Godel et al. FASEB J. Nov. 2012;26(11):4650-61. doi: 10.1096/fj.12-205096. Epub Aug. 13, 2012. The genome of the heartworm, *Dirofilaria immitis* , reveals drug and vaccine targets.

Hewitson et al. Vaccination against helminth parasite infections.

Luck et al. Concurrent transcriptional profiling of Dirofilaria immitis and its Wolbachia endosymbiont throughout the nematode life cycle reveals coordinated gene expression 11, BMC Genomics, Biomed Central Ltd, London, UK, vol. 15, No. 1, Nov. 29, 2014.

Morris et al. Vaccination with intestinal tract antigens does not induce protective immunity in a permissive model of filariasis. Experimental Parasitology vol. 135, Issue 1, Sep. 2013, pp. 87-95.

Morris et al. A Comprehensive, Model-Based Review of Vaccine and Repeat Infection Trials for Filariasis, Clinical Microbiology Reviews., vol. 26, No. 3, Jul. 1, 2013, pp. 381-421.

Morris et al. A Proteomic Analysis of the Body Wall, Digestive Tract, and Reproductive Tract of *Brugia malayi*. PLOS Neglected Tropical Diseases | DOI:10.1371/journal.pntd.0004054 Sep. 14, 2015.

Munn et al. Rational design of nematode vaccines: hidden antigens. Int J Parasitol 1997;27:359-66.

Nag et al. *Wolbachia* translation initiationfactor-1 iscopiously expressed by the adult, microfilariae and infective larvae of *Brugia malayi* and competitively inhibited by tetracycline. Acta Tropica138(2014)51-59.

Wang et al. Pan-Nematoda Transcriptomic Elucidation of Essential Intestinal Functions and Therapeutic Targets With Broad Potential. EBioMedicine 2 (2015) 1079-1089.

Anonymous: "*Dirofilaria immitis* (dog heartworm nematode) glutathione S-transferase (= cathepsin)" In: EMBL AAA21585, Jan. 1, 2005.

Keiser et al: "Vaccines for Filarial Infections" In: The Filaria, Jan. 1, 2002, Kluwer Academic Publishers, Boston, vol. 5, pp. 167-178.

*Primary Examiner* — Rodney P Swartz
(74) *Attorney, Agent, or Firm* — Judy Jarecki-Black; Suzanne Shope

(57) ABSTRACT

The present invention encompasses a vaccine composition and method of use for treating heartworm infestation in mammals. The vaccine composition includes chimeric antigens engineered and manufactured using the genetic code (i.e., the amino acid or protein sequence) of the target sequence. After introduction of the vaccine composition containing the target antigen into the host (e.g., a canine), the host will generate antibodies as part of its robust immune response to the antigen. As the antibodies circulate through the host's plasma, heartworm larvae will consume the antibodies as they feed on the plasma. The antibodies will then act on internal targets of the worm recognized as antigens.

7 Claims, 6 Drawing Sheets

Specification includes a Sequence Listing.

| SEQ ID NO | Type | Description |
|---|---|---|
| 1 | PRT | Murine IgK chain leader |
| 2 | PRT | C-myc tag |
| 3 | PRT | Serpin segment of SSFI Chimera |
| 4 | PRT | Syntenin segment of SSFI Chimera |
| 5 | PRT | Fukutin segment of SSFI Chimera |
| 6 | PRT | IF1 segment of SSFI Chimera |
| 7 | PRT | SSFI Chimera with 5' Murine IgK chain leader and 3' C-myc tag |
| 8 | DNA | Serpin segment of SSFI Chimera |
| 9 | DNA | Syntenin segment of SSFI Chimera |
| 10 | DNA | Fukutin segment of SSFI Chimera |
| 11 | DNA | IF1 segment of SSFI Chimera |
| 12 | DNA | SSFI Chimera with 5' Murine IgK chain leader and 3' C-myc tag |
| 13 | PRT | M1 segment of M1-UDP-Exp2-IF1-GST (MUEIG) Chimera |
| 14 | PRT | UDP segment of MUEIG Chimera |
| 15 | PRT | Exp2 segment of MUEIG Chimera |
| 16 | PRT | IF1 segment of MUEIG Chimera |
| 17 | PRT | GST segment of MUEIG Chimera |
| 18 | PRT | MUEIG Chimera with 5' Murine IgK chain leader and 3' C-myc tag |
| 19 | DNA | M1 segment of MUEIG Chimera |
| 20 | DNA | UDP segment of MUEIG Chimera |
| 21 | DNA | Exp2 segment of MUEIG Chimera |
| 22 | DNA | IF1 segment of MUEIG Chimera |
| 23 | DNA | GST segment of MUEIG Chimera |
| 24 | DNA | MUEIG Chimera with 5' Murine IgK chain leader and 3' C-myc tag |
| 25 | PRT | Necepsin segment of Necepsin-Prof2-TPP-ShTK (NPTS) Chimera |
| 26 | PRT | Prof2 segment of NPTS Chimera |
| 27 | PRT | TPP segment of NPTS Chimera |
| 28 | PRT | ShTK segment of NPTS Chimera |
| 29 | PRT | NPTS Chimera with 5' Murine IgK chain leader and 3' C-myc tag |
| 30 | DNA | Necepsin segment of NPTS Chimera |
| 31 | DNA | Prof2 segment of NPTS Chimera |
| 32 | DNA | TPP segment of NPTS Chimera |
| 33 | DNA | ShTK segment of NPTS Chimera |
| 34 | DNA | NPTS Chimera with 5' Murine IgK chain leader and 3' C-myc tag |
| 35 | PRT | Reprolysine segment of Reprolysin-Mrp5-Nas4 (RMN) Chimera |
| 36 | PRT | Mrp5 segment of Reprolysin-Mrp5-Nas4 (RMN) Chimera |
| 37 | PRT | Nas4 segment of Reprolysin-Mrp5-Nas4 (RMN) Chimera |
| 38 | PRT | RMN Chimera with 5' Murine IgK chain leader and 3' C-myc tag |
| 39 | DNA | Reprolysine segment of RMN Chimera |
| 40 | DNA | Mrp5 segment of Reprolysin-Mrp5-Nas4 (RMN) Chimera |
| 41 | DNA | Nas4 segment of Reprolysin-Mrp5-Nas4 (RMN) Chimera |
| 42 | DNA | RMN Chimera with 5' Murine IgK chain leader and 3' C-myc tag |
| 43 | PRT | Fat3 segment of Fat3-Enolase-DiTG-Tropomyosin (FEDT) Chimera |
| 44 | PRT | Enolase segment of FEDT Chimera |
| 45 | PRT | DiTG segment of FEDT Chimera |
| 46 | PRT | Tropomyosin segment of FEDT Chimera |
| 47 | PRT | FEDT Chimera with 5' Murine IgK chain leader and 3' C-myc tag |
| 48 | DNA | Fat3 segment of Fat3-Enolase-DiTG-Tropomyosin (FEDT) Chimera |
| 49 | DNA | Enolase segment of FEDT Chimera |
| 50 | DNA | DiTG segment of FEDT Chimera |

*FIG. 6*

| SEQ ID NO | Type | Description |
|---|---|---|
| 51 | DNA | Tropomyosin segment of FEDT Chimera |
| 52 | DNA | FEDT Chimera with 5' Murine IgK chain leader and 3' C-myc tag |
| 53 | PRT | GST segment of GST-Cathepsin (GC) Chimera |
| 54 | PRT | Cathepsin segment of GC Chimera |
| 55 | PRT | GC Chimera with 5' Murine IgK chain leader and 3' C-myc tag |
| 56 | DNA | GST segment of GST-Cathepsin (GC) Chimera |
| 57 | DNA | Cathepsin segment of GC Chimera |
| 58 | DNA | GC Chimera with 5' Murine IgK chain leader and 3' C-myc tag |

*FIG. 6 (Cont'd)*

HEARTWORM VACCINE, METHODS AND USES THEREOF

CROSS-REFERENCE TO RELATED APPLICATIONS

This application claims priority to both U.S. provisional application No. 62/319,731, filed Apr. 7, 2016, and U.S. provisional application No. 62/423,174, filed Nov. 16, 2016, both of which are incorporated herein by reference in their entireties.

INCORPORATION BY REFERENCE

Any foregoing applications and all documents cited therein or during their prosecution ("application cited documents") and all documents cited or referenced in the application cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention. Citation or identification of any such document in this application is not an admission that such document is available as prior art to the present invention and does not reflect any view of the validity, patentability and/or enforceability of such cited patent documents. All sequences referenced herein by GenBank Accession numbers are herein incorporated by reference in their entirety, and said sequences are as set forth in GenBank at as of the filing date of the present application.

STATEMENT REGARDING SEQUENCE LISTING

The Sequence Listing associated with this application is provided in text format in lieu of a paper copy, and is hereby incorporated by reference into the specification. The name of the text file containing the Sequence Listing is MER_16_298_ST25.txt. The text file is 53 KB; it was created on 14 Nov. 2016; and it is being submitted electronically via EFS-Web, concurrent with the filing of the specification.

FIELD OF THE INVENTION

The present invention encompasses non-naturally occurring chimeric heartworm vaccines, compositions and methods of use.

BACKGROUND

Cardiopulmonary dirofilariasis, (i.e., heartworm disease) is a severe vector-borne helminthiasis of dogs and cats worldwide. It is transmitted by Culicidae (i.e., mosquito) bites and caused by the development of a filarial nematode, *Dirofilaria immitis*, in the pulmonary arteries and the right ventricle of the heart. Clinically, it leads to irreversible cardiac insufficiency that can result in the death of the animal. Treatment is difficult and prevention is critical for dirofilariasis control.

Current prevention methods are based exclusively on the regular use of macrocyclic lactones to kill infective larvae inoculated by mosquitoes. An exemplary product is HEARTGARD®, which contains ivermectin as the active ingredient against the tissue stage of *D. immitis*. For about a decade, however, resistant strains of *D. immitis* have emerged, for example, in the United States, posing a problem for the control of the disease and jeopardizing the registration of new drugs.

The problem of drug resistance with respect to heartworm control is likely to spread in the coming decades. Accordingly, there is a strong need for an alternative prevention program to be used either in conjunction with current therapy or as a standalone treatment. The instant invention meets this need using a novel vaccine strategy to internal targets of *D. immitis*.

Other attempts at heartworm vaccines are known in the art. For example, U.S. Pat. No. 4,842,999 to Fuller et al., discloses a vaccine and diagnostic test for canine heartworm. The '999 patent more specifically pertains to cell lines IDi10, which produces the IDi10 monoclonal antibody directed against the 14 kD *D. immitis* antigen, and IDi76, which produces the IDi76 monoclonal antibody directed against glycoprotein antigens.

Another example, U.S. Pat. No. 5,744,593 to Klimowski et al., discloses parasitic helminth thiol specific antioxidant (TSA) larval proteins; to parasitic helminth larval TSA nucleic acid molecules, including those that encode such TSA proteins; to antibodies raised against such TSA proteins; and to compounds that inhibit parasitic helminth larval TSA activity.

Another example is found in U.S. Pat. No. 5,750,393 to Tripp et al. The '393 patent discloses antibodies raised against parasite astacin metalloendopeptidase and filarid cysteine protease proteins.

WO 1993/010225 to Grieve et al., discloses a vaccine targeting a protease that is important for life cycle transition in *D. immitis*.

Finally, U.S. Pat. No. 4,761,281 discloses a non-toxic amount of water-soluble fraction of an extract of adult *Dirofilaria* organisms and of an acid-soluble fraction of an extract of adult *Dirofilaria* organisms for use as a vaccine.

None of the above references or references not mentioned herein has produced a viable commercial product. Most efforts so far have focused on incoming L3s larvae or recombinant antigens from L3. These antigens were typically excretory-secretory antigens from the larvae epicuticle/cuticle. They are immunogenic in dogs but poorly so due to their immunosuppressive properties. Furthermore, some of them can be sloughed off leading to immune evasion. Both aspects may explain the limited efficacy of vaccines tested so far. The vaccine compound and method of treatment of the present invention seeks to improve on the prior art in a novel and nonobvious way.

SUMMARY

In one aspect, the invention is a vaccine composition against internal antigens of *Dirofilaria immitis* larvae and/or against the endosymbiont *Wolbachia pipientis*. In another aspect, the invention is a method for alleviating dirofilariasis by vaccinating a canine with a vaccine composition against internal antigens of *Dirofilaria immitis* larvae and/or against the endosymbiont *Wolbachia pipientis*. The composition and method of the instant invention may lead to more effective protective immunity against canine heartworm disease. This innovative vaccine strategy may become a useful integrated solution along with chemotherapy in the face of growing concerns related to resistance mechanisms.

BRIEF DESCRIPTION OF THE FIGURES

FIG. 6 summarizes the sequences presented in this application.

DETAILED DESCRIPTION OF THE INVENTION

Figure 1A:
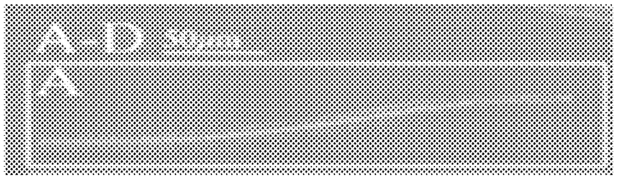
FIG. 1A shows antibody labeled with green fluorescence protein inside a *D. immitis* larvae that was incubated with plasma containing the antibody.

A vaccine against infesting immature stages of *Dirofilaria immitis* (e.g., for canine) offers a new approach for the control of heartworm disease while limiting the development of resistant parasites. It is expected to generate a balance of regulatory and effector immunity that, while not completely controlling infestation, reduces quantitatively the burden of parasite larvae and/or interferes qualitatively with their development leading to less pathogenic sterile adults. This will prevent severe disease (due to adult worms) and provide an integrated solution along with chemoprevention.

The asymptomatic pre-patent phase of *D. immitis* infection (approx. 3-4 months) offers a window of opportunity for protective immunity when the larvae are located in subcutaneous and muscular tissues, before their migration to the pulmonary arteries and right heart ventricle. There is data in dogs supporting partial protection by vaccination with irradiated larvae or with purified or recombinant parasite surface proteins. Further evidence supporting partial protection by vaccination with irradiated larvae exists in cats and cattle. Asymptomatic humans in areas endemic for onchocerciasis or lymphatic filariasis provide additional evidence.

Instead of focusing on surface antigens of larvae (an approach that has shown limitations in the past), the vaccine composition of the instant invention targets internal (i.e., "hidden" antigens) of larvae. This approach is advantageous for four reasons. First, larvae typically reside in granulomas which are accessible and attractive to immune effectors (both antibodies and cell-based immunity). Larvae ingest components of their environment (i.e., cells, lymph and proteins including antibodies). Second, the recent *D. immitis* transcriptome and full genome publications reveal targets for relevant internal *D. immitis* antigens. This idea is specifically supported by the recent publication of the proteomic analysis of the body wall, digestive and reproductive tracts of *Brugia malayi*, a related filarial. Accordingly, some of these proteins may be accessible to antibodies ingested by the worm.

Third, internal antigens are unlikely to be involved in immunomodulation, creating an opportunity for more intense and sustained immune responses than with surface antigens. In addition, internal antigens are unlikely to be involved in parasite-induced immunopathology. Because internal antigens are not involved in immune escape mechanisms, they are likely to be conserved between different heartworms (e.g., *D. immitis, D. repens*) thereby leading to broad cross protection that may be relevant to other filariasis (including human) vaccines.

Finally, internal antigens may be identified on the larvae themselves and also on their bacterial endosymbiont *Wolbachia*. Antibodies against *Wolbachia* have already been described in a *Brugia malayi* model suggesting that an immune response against the endosymbiont could kill or cripple the parasite as previously suggested by antibiotic therapy of the infected dogs. The published transcriptional profiling of *D. immitis* and its *Wolbachia* will facilitate the identification of relevant antigens in *Wolbachia*.

The present invention utilizes the strategy of antibodies targeting internal antigen targets of *D. immitis* and/or their bacterial endosymbiont *Wolbachia*. In this manner, when the larvae feed on the host plasma, the antibodies will be ingested and act on the target, killing the larvae before becoming pathogenic adult worms.

Figure 1B:
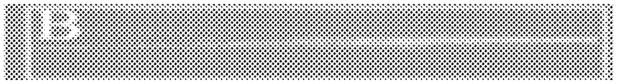
FIG. 1B shows antibody labeled with green fluorescence protein inside a *D. immitis* larvae that was incubated with plasma containing the antibody.
Figure 1C:
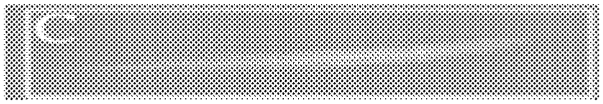
FIG. 1C shows antibody labeled with green fluorescence protein inside a *D. immitis* larvae that was incubated with plasma containing the antibody.
Figure 1D:
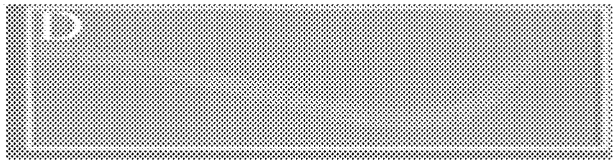
FIG. 1D shows antibody labeled with green fluorescence protein inside a *D. immitis* larvae that was incubated with plasma containing the antibody.
Figure 1F:
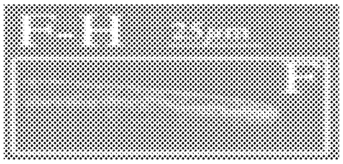
FIG. 1F shows antibody labeled with green fluorescence protein inside a *D. immitis* larvae that was incubated with plasma containing the antibody.
Figure 1G:
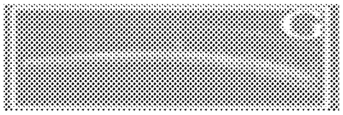
FIG. 1G shows antibody labeled with green fluorescence protein inside a *D. immitis* larvae that was incubated with plasma containing the antibody.
Figure 1H:
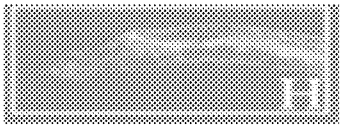
FIG. 1H shows antibody labeled with green fluorescence protein inside a *D. immitis* larvae that was incubated with plasma containing the antibody.
Figure 1E:
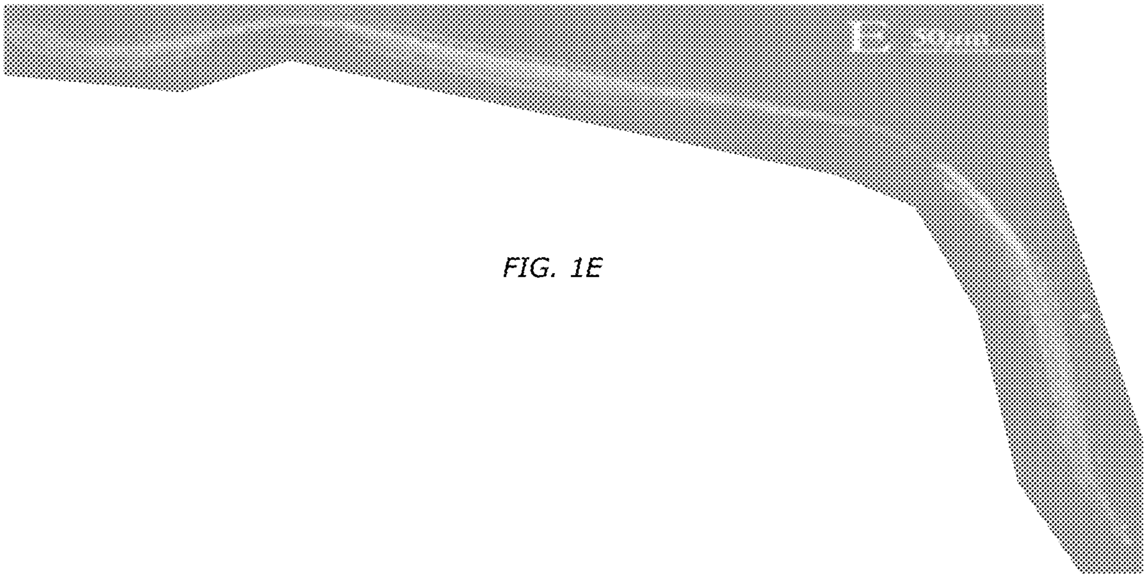
FIG. 1E shows antibody labeled with green fluorescence protein inside a *D. immitis* larvae that was incubated with plasma containing the antibody.
Figure 2:
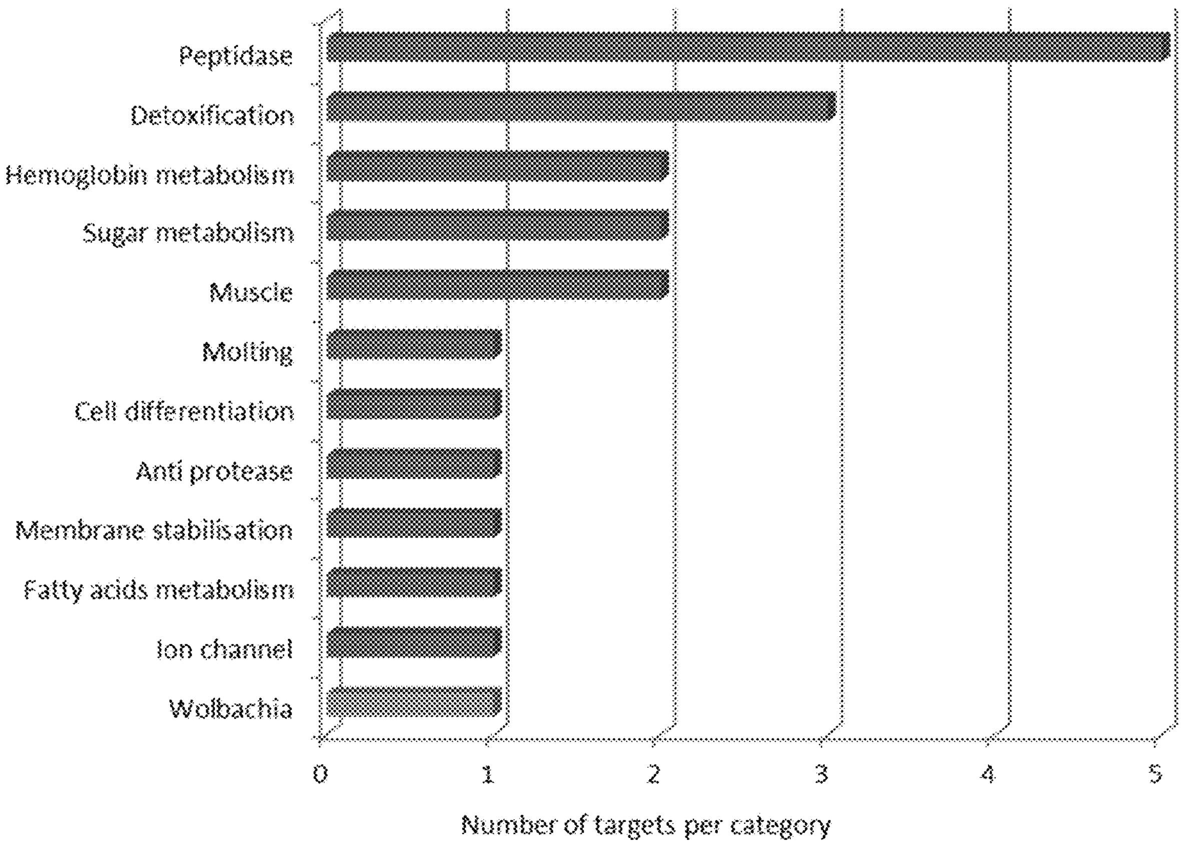
FIG. 2 is a graph showing antigenic targets by category.
Figure 3:
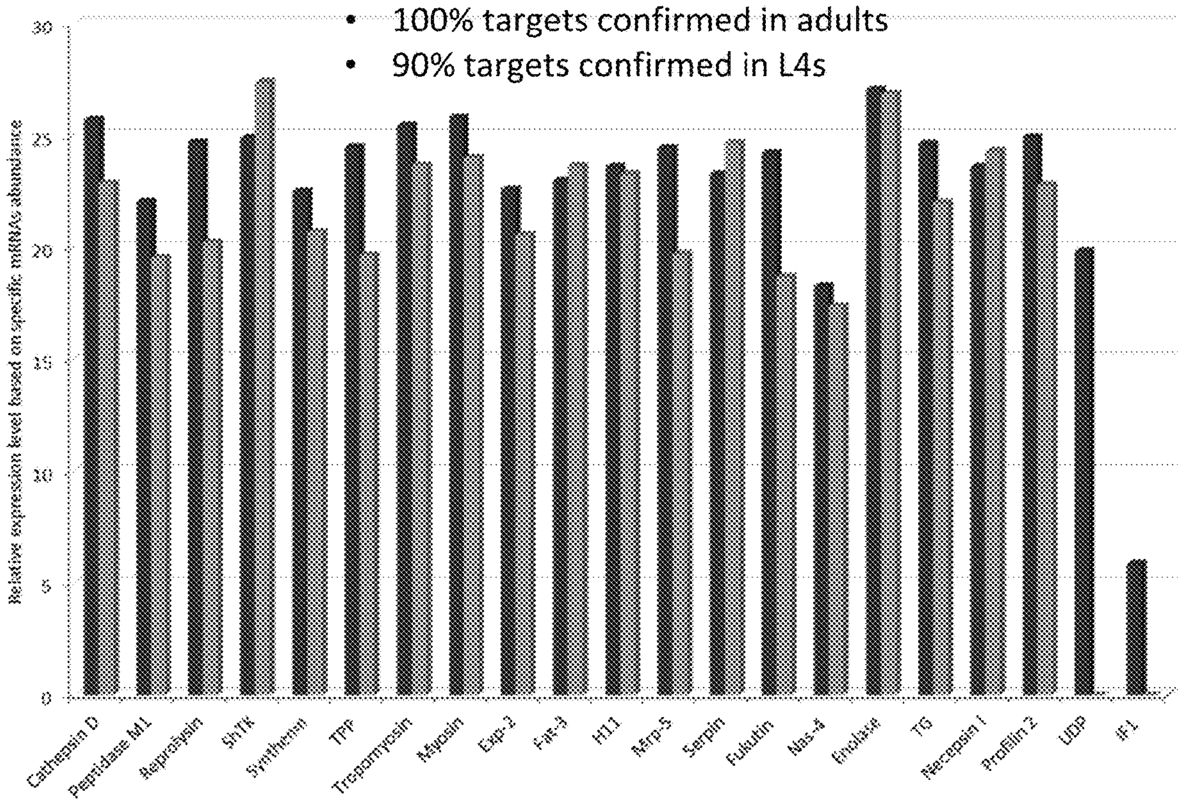
FIG. 3 is a graph showing target mRNA expression in adult and L4 stage.
Figure 4:
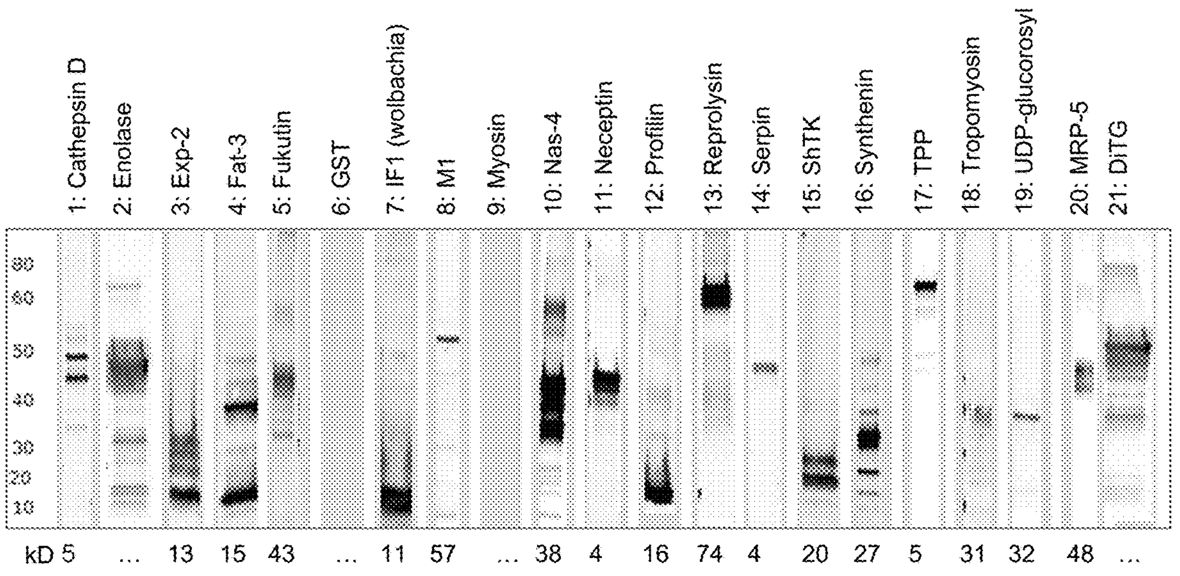
FIG. 4 is a blot showing expression of recombinantly expressed target genes.
Figure 5:
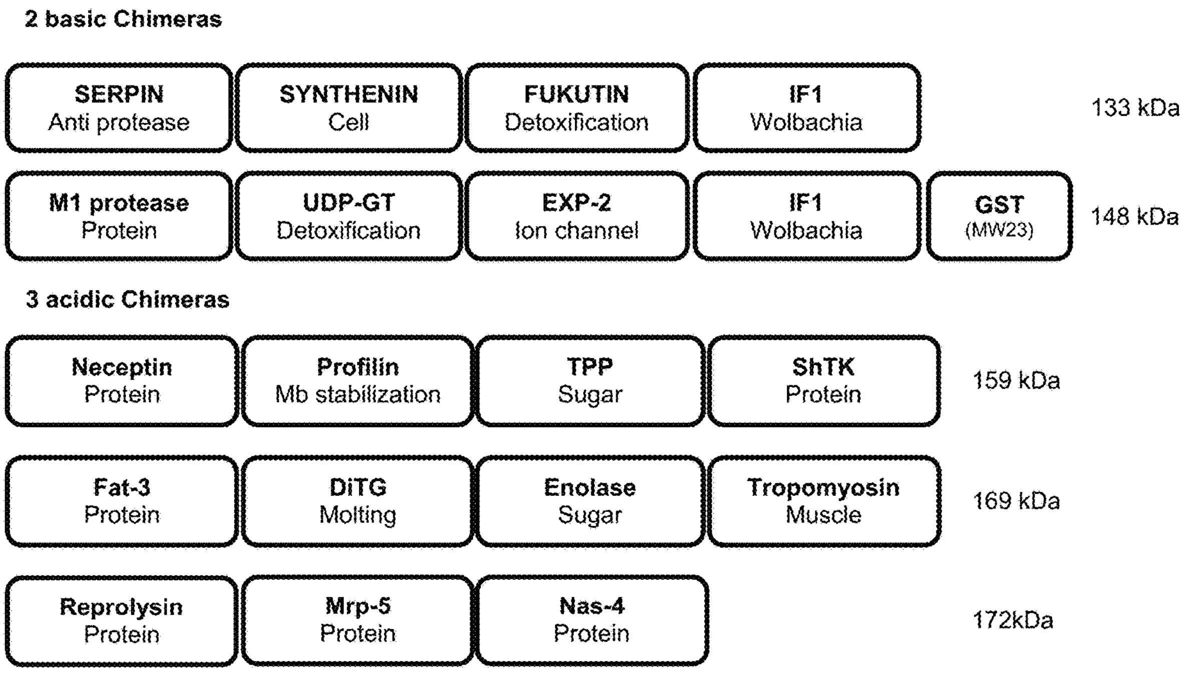
FIG. 5 is a schematic showing the structure of 2 basic and 3 acidic chimeric antigens.

Accordingly, the antigen targets of the present invention include targets critical to the survival of the larvae, such as digestive enzymes, structural proteins and reproductive organs (*Wolbachia*). Evidence of larval ingestion of plasma is shown in FIGS. 1A through 1H. *D. immitis* larvae at stage L4 were incubated with plasma containing antibodies labeled with a green fluorescent dye. FIGS. 1A through 1H show the larval ingestion of the fluorescent labeled antibodies over time.

In one aspect, the vaccine composition of the present invention includes an antigen engineered and manufactured using the genetic code (i.e., the amino acid or protein sequence) of the target *D. immitis* larvae sequence. After introduction of the vaccine composition containing the target antigen into the host (e.g., a canine), the host will generate antibodies as part of its robust immune response to the antigen. As the antibodies circulate through the host's plasma, *D. immitis* larvae in the L4 stage will consume the antibodies as they feed on the plasma. The antibodies will then act on internal targets of the worm recognized as antigens.

In another aspect, the vaccine composition of the present invention includes a chimeric antigen engineered and manufactured using the genetic code (i.e., the amino acid or protein sequence) of the target *D. immitis* larvae sequence. For example, the antigen could be a chimera of four different proteins to target four different antigen targets within *D. immitis*. This would afford the vaccine composition a broader spectrum of activity against the larvae, as the host's immune response would manufacture antibodies to four targets within *D. immitis* at once.

Antigen targets include, for example, the M1 peptidase protein, the cathepsin protein (involved in blood digestion), serpin protein (involved in larvae defense against host proteases), fukutin protein (involved in detoxification), UDP-glucorosyl protein (involved in detoxification), fat-3 protein (involved in fatty acid metabolism), exp-2 protein (involved in pharyngeal pumping), synthenin protein (involved in cell growth and differentiation), IF-1 protein (involved in translation initiation), reprolysin protein (involved in metalloprotease activity), ShTK protein (involved in protease activity), nas-4 protein (involved in metalloprotease activity), H11 protein (involved in aminopeptidase activity), tropomyosin and myosin protein (involved in muscle development) and TPP protein (involved in trehalose metabolism). Table 1 summarizes the protein targets, their currently understood function, their presence in larval stage L4, molecular weight, secondary structure and other parameters.

TABLE 1

| Protein/literature | Function | Presence L4 | Protein Data Bank | pI | Mw | aa | Glycosylation | Trans-membrane Helices | Secondary structure | Homology dog |
|---|---|---|---|---|---|---|---|---|---|---|
| M1 | peptidase | | 5AB2 | 9.6 | 56.1 | 472 | 3 | 0 | a | 27% |
| Cathepsin | Blood digestion | yes | 3PSG | 8.8 | 58.7 | 516 | 3 | 0 | a b | 48% |
| Serpin | Serine protease inhibitor. Avoid parasite digestion by host proteases | yes | 2ZV6 | 8.95* | 41.2* | 388 | 2/3 | 1 | a b | 30% |
| Fukutin | Detoxification | | non | 8.44* | 39.5* | 364 | mini 2 | 1 | α b | 29% |
| UDP-glucorosyl | Detoxification | | 2C1X | 7.7 | 21.2 | 183 | 0 | 0 | | 33% |
| UDP-glucorosyl | Detoxification | | non | 7 | 28.2 | 249 | 2 | 0 | a | 0% |
| fat-3 | fatty acid metabolism | | non | 6.8 | 52.6 | 452 | 1 | 4 | | 27% |
| exp-2 | pharyngeal pumping in C elegans | | 2R9R | 7.6 | 30.9 | 270 | 2 | 4 | | 37% |
| Synthenin | cell growth, development and differentiation | | 10BZ | 8.5 | 26.2 | 236 | 3 | 0 | a b | 32% |
| IF1 | translation initiation factor | NA | non | 10.1 | 9.9 | 87 | 0 | 0 | b | 0% |
| Reprolysin | metalloprotease | | 2ERO | 5.42* | 70.9* | 874 | 3 | 1 | a b | 38% |
| ShTK | Protease? | | non | 4.5 | 19.5 | 177 | 1? | 0 | a | 0% |
| nas-4 | metalloproteinase | yes | 1AST | 6.02 | 34.4 | 298 | 4 | 1 | a b | 41% |
| H11 | aminopeptidase | | 4FYQ | 4.8 | 100 | 866 | 6 | 1 | a b | 37% |
| Tropomyosin | body wall muscle protein | yes | 2W49 | 4.5 | 29.6 | 253 | 2? | 0 | a | 59% |
| Myosin | body wall muscle protein | yes | 1KK7 (1 à 849) | 5.55 | 226 | 1960 | 5? | 0 | a | 71% |
| TPP | trehalose metabolism | | 4OFZ | 5.42 | 57 | 511 | 2 | 0 | a b | 0% |

Any suitable expression system known in the art may be used to express the chimeric protein of the invention. The expression system will preferably be eukaryotic and capable of posttranslational modification of proteins (e.g., baculovirus, yeast or other eukaryotic cells). In vivo expression systems may be, for example, canarypox, DNA or adenovirus systems.

The vaccines may comprise pharmaceutically or veterinarily acceptable carriers or vehicles or adjuvants or excipients. For example, a pharmaceutically or veterinarily acceptable carrier or vehicle or adjuvant or excipient can be sterile water, a 0.9% NaCl (e.g., saline) solution or a phosphate buffer. Other pharmaceutically or veterinarily acceptable carrier or vehicle or adjuvant or excipients that can be used for methods of this invention include, but are not limited to, poly-(L-glutamate) or polyvinylpyrrolidone. The pharmaceutically or veterinarily acceptable carrier or vehicle or adjuvant or excipients may be any compound or combination of compounds facilitating the administration of the vector or chimeric protein; advantageously, the carrier, vehicle or adjuvant or excipient may facilitate transfection and/or improve preservation of the vector or chimeric protein. Doses and dose volumes are herein discussed in the general description and can also be determined by the skilled artisan from this disclosure, read in conjunction with the knowledge in the art, without undue experimentation.

In some embodiments, the immunological compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., 1996; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on page 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters. The oil is used in combination with emulsifiers to form an emulsion. The emulsifiers may be nonionic surfactants, such as: esters of on the one hand sorbitan, mannide (e.g., anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121.

Among the type (1) adjuvant polymers, preference is given to polymers of cross linked acrylic or methacrylic acid, especially cross linked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers cross linked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g., vinyls, allyls and other ethylenically unsaturated groups. The unsaturated radicals can also contain other substituents, such as methyl. Products sold under the name Carbopol (BF Goodrich, Ohio, USA) are especially suitable. They are cross linked by allyl saccharose or by allyl pentaerythritol. Among them, reference is made to Carbopol 974P, 934P and 971P.

As to the maleic anhydride-alkenyl derivative copolymers, preference is given to EMA (Monsanto), which are straight-chain or cross linked ethylene-maleic anhydride copolymers and they are, for example, cross linked by divinyl ether. The acrylic or methacrylic acid polymers and EMA are well known and are generally soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final immunological or vaccine composition can range between about 0.01 and about 1.5% w/v, about 0.05 to about 1% w/v or about 0.1 to about 0.4% w/v.

The cytokine or cytokines (5) can be in protein form in the immunological or vaccine composition, or can be co-expressed in the host with the immunogen or immunogens or epitope(s) thereof. The invention comprehends preparing such combination compositions; for instance by admixing the active components, advantageously together and with an adjuvant, carrier, cytokine, and/or diluent. Cytokines that may be used in the present invention include, but are not limited to, granulocyte colony stimulating factor (G-CSF), granulocyte/macrophage colony stimulating factor (GM-CSF), interferon α (IFNα), interferon β (IFNβ), interferon γ, (IFNγ), interleukin-1α (IL-1α), interleukin-1β (IL-1β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNFα), tumor necrosis factor β (TNFβ), and transforming growth factor β (TGFβ). It is understood that cytokines can be co-administered and/or sequentially administered with the immunological or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a feline cytokine for preparations to be administered to a feline).

When vaccines comprise plasmids, cationic lipids containing a quaternary ammonium salt may be added to increase vaccine efficacy. In particular embodiments, the vaccines may comprises DMRIE (N-(2-hydroxyethyl)-N,N-dimethyl-2,3-bis(tetradecyloxy)-1-propane ammonium; WO96/34109) and/or DOPE (dioleoyl-phosphatidyl-ethanol amine). Combinations are well known, especially including DMRIE-DOPE. The plasmid mixture with the adjuvant may be formed extemporaneously and/or contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g., between about 10 and about 60 minutes prior to administration, such as about 30 minutes prior to administration. When DOPE is present, the DMRIE:DOPE molar ratio may be about 95:about 5 to about 5:about 95, or about 1:about 1, e.g., 1:1. The DMRIE or DMRIE-DOPE adjuvant:plasmid weight ratio can be between about 50:about 1 and about 1:about 10, such as about 10:about 1 and about 1:about 5, and advantageously about 1:about 1 and about 1:about 2, e.g., 1:1 and 1:2.

In some embodiments, the pharmaceutically or veterinarily acceptable carrier, adjuvant, excipient, or vehicle may a water-in-oil emulsion. Examples of suitable water-in-oil emulsions include oil-based water-in-oil vaccinal emulsions which are stable and fluid at 4° C. containing: from about 6 to about 50 v/v % of an antigen-containing aqueous phase, particularly from about 12 to about 25 v/v %, from about 50 to about 94 v/v % of an oil phase containing in total or in part a non-metabolizable oil (e.g., mineral oil, such as paraffin oil) and/or metabolizable oil (e.g., vegetable oil, or fatty acid, polyol or alcohol esters), from about 0.2 to about 20 p/v % of surfactants, preferably from about 3 to about 8 p/v %, the latter being in total or in part, or in a mixture either polyglycerol esters, said polyglycerol esters being, in some embodiments, polyglycerol (poly)ricinoleates, or polyoxyethylene ricin oils or else hydrogenated polyoxyethylene ricin oils.

Examples of surfactants that may be used in a water-in-oil emulsion include ethoxylated sorbitan esters (e.g., polyoxyethylene (20) sorbitan monooleate (TWEEN 80®), available from AppliChem, Inc., Cheshire, Conn.) and sorbitan esters (e.g., sorbitan monooleate (SPAN 80®), available from Sigma Aldrich, St. Louis, Mo.). In addition, with respect to a water-in-oil emulsion, see also U.S. Pat. No. 6,919,084. In some embodiments, the antigen-containing aqueous phase comprises a saline solution comprising one or more buffering agents. An example of a suitable buffering solution is phosphate buffered saline. In one embodiment, the water-in-oil emulsion may be a water/oil/water (W/O/W) triple emulsion (see, e.g., U.S. Pat. No. 6,358,500). Examples of other suitable emulsions are described in U.S. Pat. Nos. 7,371,395 and 9,107,859, the disclosures of which are herein incorporated by reference in their entireties.

In an embodiment, the disclosure provides a composition for providing to an animal in need thereof protective immunity against *D. immitis*, or diseases caused by *D. immitis*, comprising at least one *D. immitis* or bacterial endosymbiont *Wolbachia* polypeptide having at least 80%, 85%, 90%, 91%, 92%, 93%, 94%, 95%, 96%, 97%, 98%, 99% or 99.5% identity to SEQ ID NO: 3-7, 13-18, 25-29, 35-38, 43-47, 53-55, combinations thereof, effective immunologically equivalent portions thereof, effective immunologically equivalent variants thereof or combinations of any of the foregoing.

As regards "percent identity," it is intended that a non-identical molecule possess a statistically similar biological function, as compared to the molecule having the reference sequence. For example, since TPP plays a role in trehalose metabolism, a polypeptide having a recited percent identity to the TPP sequence should play the same role in trehalose metabolism. Moreover, at a minimum, the non-identical polypeptide should elicit a statistically similar or better immunological response in the target animal, as compared with the reference polypeptide. Accordingly, it is intended that polypeptide variations having a specified percent identity to a reference polypeptide are encompassed by the invention.

By "immunologically equivalent portions," it is intended that the portion is capable of eliciting a statistically similar (or better) safe and effective immune response, relative to the larger polypeptide sequence from which the portion was taken or derived. As such, if a composition comprising a protein having a sequence as set forth in SEQ ID NO: 3-7, 13-18, 25-29, 35-38, 43-47 or 53-55 protects 80% of vaccinated animals from subsequent virulent challenge, and a given truncation of polypeptide selected protects 82% of vaccinated animals, then the truncation is an "immunologically equivalent portion" of the polypeptide originally selected from or derived from one of the sequences set forth in SEQ ID NO: 3-7, 13-18, 25-29, 35-38, 43-47 and 53-55.

By "immunologically equivalent variants," it is intended that the variant is capable of eliciting a statistically similar (or better) safe and effective immune response, relative to the larger polypeptide sequence from which the variant was taken or derived. As such, if a composition comprising a protein having a sequence as set forth in SEQ ID NO: 3-7, 13-18, 25-29, 35-38, 43-47 or 53-55 protects 80% of vaccinated animals from subsequent virulent challenge, and a given truncation of polypeptide selected protects 82% of vaccinated animals, then the truncation is an "immunologically equivalent variant" of the polypeptide originally selected from or derived from one of the sequences set forth in SEQ ID NO: 3-7, 13-18, 25-29, 35-38, 43-47 and 53-55. "Variants" are intended to encompass polypeptides having differences that have positive, neutral, or insignificant negative impact on immunological efficacy. For example, variants include polypeptides having conservative amino acid substitutions, relative to the sequences as set forth in SEQ ID NO: 3-7, 13-18, 25-29, 35-38, 43-47 and 53-55. In particular embodiments, the conservative amino acid substitutions only occur outside immunologically important epitopes. Applicants also envision that the invention may be practiced using combinations of "portions" and "variants." For example, an immunologically equivalent portion of the polypeptide could also have one or more conservative amino acid substitutions.

Moreover, it well within the ambit of the skilled person to take any of the disclosed sequences, for example, SEQ ID NO: 3 (i.e. the Serpin segment of SSFI chimera) and subject it to BLAST against the available sequence databases. Using this or other approaches, the skilled person can find other Serpin proteins that could serve as equivalents of the Serpin having the sequence set forth in SEQ ID NO: 3. As such, now that the invention has been disclosed, a skilled person using routine work may discover and/or evaluate useful equivalents of the polypeptides and chimeric polypeptides disclosed herein.

In another embodiment, the composition for providing protective immunity against *D. immitis* or diseases caused by *D. immitis*, comprises at least one *D. immitis* or *Wolbachia* polypeptide having at least 85% identity to SEQ ID NO: 3-7, 13-18, 25-29, 35-38, 43-47 or 53-55, combinations thereof or immunological equivalent portions thereof. In other embodiments, the *D. immitis* or *Wolbachia* polypeptide has at least 90%, 91%, 92%, 93%, 94%, 95%, 96%, 97%, 98%, 99% or 100% identity to SEQ ID NO: 3-6, 13-17, 25-28, 35-38, 43-46 or 53-54.

In yet another embodiment, the composition comprises a polypeptide encoded by a nucleic acid sequence having at least 80%, 85%, 90%, 91%, 92%, 93%, 94%, 95%, 96%, 97%, 98%, 99% or 100% identity to one of the sequences as set forth in any one of SEQ ID NOs: 8-12, 19-24, 30-34, 39-42, 48-52 or 56-58.

In another embodiment, the nucleic acid sequence has at least 98% identity to one of the sequences as set forth in any one of SEQ ID NOs: 8-12, 19-24, 30-34, 39-42, 48-52 or 56-58.

In another embodiment, the nucleic acid sequence has 100% identity to one of the sequences as set forth in any one of SEQ ID NOs: 8-12, 19-24, 30-34, 39-42, 48-52 or 56-58.

In another embodiment, the nucleic acid sequence is as set forth in any one of SEQ ID NOs: 8-12, 19-24, 30-34, 39-42, 48-52 or 56-58.

In another aspect, the disclosure provides a method for providing to an animal in need thereof protective immunity against one or more pathogenic or parasitic *D. immitis*, comprising administering to an animal a vaccine comprising an immunoprotective effective amount of a *D. immitis* or *Wolbachia* polypeptide selected from, or having at least 80% identity to, a polypeptide having the sequence set forth in SEQ ID NO: 3-6, 13-17, 25-28, 35-38, 43-46 or 53-54.

In an embodiment, the method of providing protective immunity comprises the steps of administering to an animal a vaccine comprising an immunoprotective effective amount of a polypeptide selected from, or having at least 80% identity to, a polypeptide having the sequence set forth in SEQ ID NO: 3-6, 13-17, 25-28, 35-38, 43-46 or 53-54.

In another aspect, the disclosure provides a vector capable of expressing a recombinant DNA, wherein the recombinant DNA is selected from any one of SEQ ID NOs: 8-12, 19-24, 30-34, 39-42, 48-52 or 56-58; or wherein the recombinant DNA is at least 75%, 80%, 85%, 90%, 95% or 98% identical to the sequences as set forth in any one of SEQ ID NOs: 8-12, 19-24, 30-34, 39-42, 48-52 or 56-58.

In yet another aspect, the disclosure provided a recombinant DNA vaccine comprising:

(a) a recombinant DNA wherein the recombinant DNA comprises one or more of the sequences as set forth in SEQ ID NOs: 8-12, 19-24, 30-34, 39-42, 48-52 or 56-58; and (b) a vector capable of expressing the recombinant DNA when the recombinant DNA is inserted into the vector, wherein the recombinant DNA is inserted into the vector such that a recombinant protein is expressed when the vector is provided in an appropriate host.

The disclosure also provides a method for producing a vaccine against a *D. immitis*-related disorder comprising the steps of:

(a) providing a recombinant DNA, wherein the recombinant DNA comprises any one or more of the sequences as set forth in SEQ ID NOs: 8-12, 19-24, 30-34, 39-42, 48-52 or 56-58;

(b) providing a vector capable of expressing the recombinant DNA when the recombinant DNA is inserted into the vector; and (c) inserting the recombinant DNA into the vector, wherein the recombinant DNA is inserted into the vector such that a recombinant protein is expressed when the vector is provided in an appropriate host, thereby producing the vaccine.

The disclosure further provides a method for producing an immunoprotective peptide for use in a vaccine against a *D. immitis*-related disorder comprising:

(a) providing a recombinant DNA, wherein the recombinant DNA is selected from:

(i) a recombinant DNA that encodes an immunogenic epitope or immunologically active fragment of any one or more of the nucleic acid sequences as set forth in SEQ ID NO: 8-12, 19-24, 30-34, 39-42, 48-52 or 56-58; or (ii) a recombinant DNA that encodes a protein fragment of at least 40%, 50%, 60% 70%, 80%, 90% or 95% of the length of the amino acid sequence as set forth in SEQ ID NO: 3-6, 13-17, 25-28, 35-38, 43-46 or 53-54;

(b) providing a vector capable of expressing the recombinant DNA when the recombinant DNA is inserted into the vector;

(c) inserting the recombinant DNA into the vector;

(d) providing a bacterial strain or insect cell line;

(e) transforming the vector into the bacterial strain or insect cell line such that a recombinant protein is expressed when the vector is transformed into the bacterial strain or insect cell line; and (f) harvesting the recombinant protein from the bacterial strain or insect cell line, thereby producing the immunoprotective protein.

In some embodiments of the method, the animal is protected against *D. immitis*, and diseases caused thereby, including heartworm disease. In some embodiments, the animal may be administered about 1 ml of vaccine. The vaccine may also be administered as two subcutaneous doses, for example, at 21-day intervals. In an example, the animal is a canine, and the vaccine may comprise additional antigens that provide immunity against additional canine pathogens. The additional antigens may be selected from *Leptospira* canine parvovirus (CPV), canine parainfluenza virus (CPi2), canine distemper virus (CDV), adenovirus, herpesvirus, rabies, canine coronavirus, and combinations thereof.

In some embodiments, the polypeptide is a chimeric polypeptide, comprising a murine IgK leader sequence and one of the following combinations of polypeptides: a) SEQ ID NOs: 3-6; b) SEQ ID NOs:13-17; c) SEQ ID NOs:25-28; d) SEQ ID NOs:35-38; e) SEQ ID NOs:43-46; or f) SEQ ID NOs:53-54.

The chimera may be linked together by one or more amino acids, which are not part of the *D. immitis* or *Wolbachia* polypeptide. For example, "GSSG" may be used as a spacer between polypeptides having the sequences as set forth in SEQ ID NO: 3, 4, 5 and 6. In such an embodiment, the chimeric polypeptide would have the following structure: SEQ3-GSSG-SEQ4-GSSG-SEQ5-GSSG-SEQ6. All other combinations and permutations of *D. immitis* and *Wolbachia* polypeptides are envisioned by the inventors, as are different lengths and types of amino acids for the spacers. In particular embodiments, chimeras may comprise either a plurality of acidic or basic *D. immitis* and/or *Wolbachia* polypeptides.

In an aspect, the invention provides an immunological or vaccine composition for alleviating, treating or preventing heartworm disease in an animal in need thereof, comprising internal antigen(s) of *D. immitis* or *D. repens* larvae and/or antigens of the endosymbiont *Wolbachia pipientis* (*W. pipientis*).

In some embodiments, the composition provides cross-protection against at least two different species of filarial worms.

In some embodiments, the composition comprises a chimeric antigen comprising at least two different internal antigens.

In some embodiments, the two different internal antigens are both *D. immitis* antigens.

In some embodiments, the chimeric antigen comprises:

a) at least two *D. immitis* and/or *Wolbachia* proteins selected from Cathepsin, Cathepsin D, Enolase, Exp-2, Fat-3, Fukutin, IF1, M1, Myosin, Nas-4, Neceptin, Profilin, Reprolysin, Serpin, ShTK, Synthenin, TPP, Tropomyosin, UDP-glucorosyl, MRP-5, DiTG and H11; and/or b) immunologically equivalent portions of at least two *D. immitis* proteins selected from Cathepsin, Cathepsin D, Enolase, Exp-2, Fat-3, Fukutin, IF1, M1, Myosin, Nas-4, Neceptin, Profilin, Reprolysin, Serpin, ShTK, Synthenin, TPP, Tropomyosin, UDP-glucorosyl, MRP-5, DiTG and H11; and/or c) immunologically equivalent variants of at least two *D. immitis* proteins selected from Cathepsin, Cathepsin D, Enolase, Exp-2, Fat-3, Fukutin, IF1, M1, Myosin, Nas-4, Neceptin, Profilin, Reprolysin, Serpin, ShTK, Synthenin, TPP, Tropomyosin, UDP-glucorosyl, MRP-5, DiTG and H11.

In some embodiments of the composition, the chimeric antigen comprises only acidic or basic *D. immitis* and/or *Wolbachia* proteins, in addition to optionally comprising amino acid linkers and/or immunological tag polypeptides.

In some embodiments of the composition, the chimeric antigen comprises or consists essentially of:

a) Serpin, Synthenin, Fukutin and IF1; or b) M1, UDP-glucorosyl, Exp-2, IF1 and optionally GST; or c) Neceptin, Profilin, TPP and ShTK; or d) Fat-3, DiTG, Enolase and Tropomyosin; or e) Reprolysin, Mrp-5 and Nas-4; or f) an acidic chimera comprising or consisting essentially of:

1) Neceptin and one or more selected from Profilin, TPP, ShTK, Fat-3, DiTG, Enolase, Tropomyosin, Reprolysin, Mrp-5 and Nas-4; or 2) Profilin and one or more selected from Neceptin, TPP, ShTK, Fat-3, DiTG, Enolase, Tropomyosin, Reprolysin, Mrp-5 and Nas-4; or 3) TPP and one or more selected from Neceptin, Profilin, ShTK, Fat-3, DiTG, Enolase, Tropomyosin, Reprolysin, Mrp-5 and Nas-4; or 4) ShTK and one or more selected from Neceptin, Profilin, TPP, Fat-3, DiTG, Enolase, Tropomyosin, Reprolysin, Mrp-5 and Nas-4; or 5) Fat-3 and one or more selected from Neceptin, Profilin, TPP, DiTG, Enolase, Tropomyosin, Reprolysin, Mrp-5 and Nas-4; or 6) DiTG and one or more selected from Neceptin, Profilin, TPP, ShTK, Fat-3, Enolase, Tropomyosin, Reprolysin, Mrp-5 and Nas-4; or 7) Enolase and one or more selected from Neceptin, Profilin, TPP, ShTK, Fat-3, DiTG, Tropomyosin, Reprolysin, Mrp-5 and Nas-4; or 8) Tropomyosin and one or more selected from Neceptin, Profilin, TPP, ShTK, Fat-3, DiTG, Enolase, Reprolysin, Mrp-5 and Nas-4; or
9) Reprolysin and one or more selected from Neceptin, Profilin, TPP, ShTK, Fat-3, DiTG, Enolase, Tropomyosin, Mrp-5 and Nas-4; or
10) Mrp-5 and one or more selected from Neceptin, Profilin, TPP, ShTK, Fat-3, DiTG, Enolase, Tropomyosin, Reprolysin, and Nas-4; or
11) Nas-4 and one or more selected from Neceptin, Profilin, TPP, ShTK, Fat-3, DiTG, Enolase, Tropomyosin, Reprolysin and Mrp-5; or g) a basic chimera comprising or consisting essentially of:
1) Serpin and one or more selected from Synthenin, Fukutin, IF1, M1, UDP-glucorosyl, Exp-2; or
2) Synthenin and one or more selected from Serpin, Fukutin, IF1, M1, UDP-glucorosyl, Exp-2; or
3) Fukutin and one or more selected from Serpin, Synthenin, IF1, M1, UDP-glucorosyl, Exp-2; or
4) IF1 and one or more selected from Serpin, Synthenin, Fukutin, M1, UDP-glucorosyl, Exp-2; or
5) M1 and one or more selected from Serpin, Synthenin, Fukutin, IF1, UDP-glucorosyl, Exp-2; or
6) UDP-glucorosyl and one or more selected from Serpin, Synthenin, Fukutin, IF1, M1, Exp-2; or
7), Exp-2 and one or more selected from Serpin, Synthenin, Fukutin, IF1, M1, UDP-glucorosyl.

In some embodiments, the composition comprises at least one *D. immitis* and/or *W. pipientis* polypeptide selected from:

a) a polypeptide having at least 80% identity to a polypeptide having the sequence set forth in SEQ ID NO: 3-7, 13-18, 25-29, 35-38, 43-47 or 53-55;
b) an immunologically effective equivalent portion(s) of the polypeptide of (a);
c) an immunologically effective variant(s) of the polypeptide of (a); and
d) combinations of any of the polypeptide of (a), (b), or (c).

In some embodiments of the composition the polypeptide has at least 90% identity to a polypeptide having the sequence set forth in SEQ ID NO: 3-7, 13-18, 25-29, 35-38, 43-47 or 53-55 or combinations thereof.

In some embodiments, the polypeptide is 100% identical to a polypeptide having the sequence set forth in SEQ ID NO: 3-7, 13-18, 25-29, 35-38, 43-47 or 53-55 In some embodiments, the polypeptide is encoded by a nucleic acid sequence having at least 80%, 85%, 90% or 98% identity to the sequence as set forth in SEQ ID NO: 8-12, 19-24, 30-34, 39-42, 48-52 or 56-58.

In some embodiments, the nucleic acid sequence is as set forth in any one of SEQ ID NOs: 8-12, 19-24, 30-34, 39-42, 48-52 or 56-58.

In another aspect, the invention provides a method for vaccinating an animal against heartworm disease or providing an animal in need thereof with protective immunity against *D. immitis*, or diseases caused by *D. immitis*, comprising the step of administering at least one dose of the immunological composition to an animal susceptible to heartworm disease.

In another aspect, the invention provides a recombinant viral or plasmid vector capable of expressing in vivo in an animal host a recombinant DNA, wherein the recombinant DNA comprises a nucleic acid having the sequence set forth in SEQ ID NO: 8-12, 19-24, 30-34, 39-42, 48-52, 56-58 or combinations thereof.

In some embodiments, the recombinant vaccine comprising the vector is disclosed herein.

In another aspect, the invention provides a method for producing an immunoprotective polypeptide for use in a vaccine against a *D. immitis*-related disorder comprising:

a) providing a recombinant DNA, wherein the recombinant DNA is selected from:
i) a recombinant DNA that encodes an immunogenic epitope or immunologically active fragment of any one or more of the nucleic acid sequences as set forth in SEQ ID NO: 8-12, 19-24, 30-34, 39-42, 48-52 or 56-58; or
ii) a recombinant DNA that encodes a protein fragment of at least 40%, 50%, 60% 70%, 80%, 90% or 95% of the length of the amino acid sequence as set forth in SEQ ID NO: 3-7, 13-18, 25-29, 35-38, 43-47 or 53-55;
b) providing a vector capable of expressing the recombinant DNA when the recombinant DNA is inserted into the vector;
c) inserting the recombinant DNA into the vector;
d) providing a bacterial strain or an insect cell line;
e) transforming the vector into the bacterial strain or insect cell line such that a recombinant protein is expressed when the vector is transformed into the bacterial strain or the insect cell line; and
f) harvesting the recombinant protein from the bacterial strain, thereby producing the immunoprotective polypeptide.

In some embodiments of the method, the animal is protected against *D. immitis*-related diseases.

In some embodiments, the animal is administered about 1 ml of vaccine, and/or the animal is administered 2 subcutaneous doses; and/or the 2 doses are administered at a 21-day interval.

In some embodiments, the vaccine comprises additional antigens that provide immunity against additional canine pathogens.

In some embodiments, the additional antigens are selected from canine parvovirus (CPV), canine parainfluenza virus (CPi2), canine distemper virus (CDV), adenovirus, herpesvirus, rabies, canine coronavirus, and combinations thereof.

Descriptions/Definitions

By "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a polypeptide, an epitope, a hapten, or any combination thereof. Alternately, the immunogen or antigen may comprise a toxin or antitoxin.

The terms "protein", "peptide", "polypeptide" and "polypeptide fragment" are used interchangeably herein to refer to polymers of amino acid residues of any length. The polymer can be linear or branched, it may comprise modified amino acids or amino acid analogs, and it may be interrupted by chemical moieties other than amino acids. The terms also encompass an amino acid polymer that has been modified naturally or by intervention; for example disulfide bond formation, glycosylation, lipidation, acetylation, phosphorylation, or any other manipulation or modification, such as conjugation with a labeling or bioactive component.

The term "immunogenic or antigenic polypeptide" as used herein includes polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., Epitope Mapping Protocols in Methods in Molecular Biology, Vol. 66 (Glenn E. Morris, Ed., 1996). For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

As discussed herein, the invention encompasses active fragments and variants of the antigenic polypeptide. Thus, the term "immunogenic or antigenic polypeptide" further contemplates deletions, additions and substitutions to the sequence, so long as the polypeptide functions to produce an immunological response as defined herein. The term "conservative variation" denotes the replacement of an amino acid residue by another biologically similar residue, or the replacement of a nucleotide in a nucleic acid sequence such that the encoded amino acid residue does not change or is another biologically similar residue. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine, threonine, tyrosine. Phenylalanine, tryptophan, and tyrosine are sometimes classified as aromatic amino acids. Examples of conservative variations include the substitution of one hydrophobic residue such as isoleucine, valine, leucine or methionine for another hydrophobic residue, or the substitution of one polar residue for another polar residue, such as the substitution of arginine for lysine, glutamic acid for aspartic acid, or glutamine for asparagine, and the like; or a similar conservative replacement of an amino acid with a structurally related amino acid that will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide. All of the polypeptides produced by these modifications are included herein. The term "conservative variation" also includes the use of a substituted amino acid in place of an unsubstituted parent amino acid provided that antibodies raised to the substituted polypeptide also immunoreact with the unsubstituted polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms and/or clinical disease signs normally displayed by an infected host, a quicker recovery time and/or a lowered viral titer in the infected host.

By "animal" is intended mammals, birds, and the like. Animal or host as used herein includes mammals and human. The animal may be selected from the group consisting of equine, canine, feline, ovine, bovine, porcine, avian, primate, ferrets, seals, and fish. The term "animal" also includes an individual animal in all stages of development, including newborn, embryonic and fetal stages.

Unless otherwise explained, all technical and scientific terms used herein have the same meaning as commonly understood by one of ordinary skill in the art to which this disclosure belongs. The singular terms "a", "an", and "the" include plural referents unless context clearly indicates otherwise. Similarly, the word "or" is intended to include "and" unless the context clearly indicate otherwise.

The invention will now be further described by way of the following non-limiting examples.

What is claimed is:

1. A recombinant viral or plasmid vector capable of expressing in vivo in an animal host a recombinant DNA, wherein the recombinant DNA comprises a nucleic acid having at least one of SEQ ID NO: 8-12, 19-24, 30-34, 39-42, 48-52, 56-58 or combinations thereof.

2. A vaccine comprising the recombinant vector of claim 1 and a pharmaceutically acceptable carrier, vehicle, adjuvant or excipient.

3. A method for producing an immunoprotective polypeptide for use in a vaccine against diseases caused by *D. immitis* comprising:
  - a) providing a recombinant DNA, wherein the recombinant DNA is
    - i) a recombinant DNA that encodes an immunogenic epitope or immunologically active fragment, wherein the recombinant DNA is selected from any one or more of the nucleic acid sequences as set forth in SEQ ID NO: 8-12, 19-24, 30-34, 39-42, 48-52 or 56-58; or
    - ii) a recombinant DNA that encodes a protein fragment, wherein the length of the protein fragment is at least 40% of the length of any one or more of the polypeptide sequences as set forth in SEQ ID NO: 3-7, 13-18, 25-29, 35-38, 43-47 or 53-55;
  - b) providing a vector capable of expressing the recombinant DNA when the recombinant DNA is inserted into the vector;
  - c) inserting the recombinant DNA into the vector;
  - d) providing a bacterial strain or an insect cell line;
  - e) transforming the vector into the bacterial strain or insect cell line such that a recombinant protein is expressed when the vector is transformed into the bacterial strain or the insect cell line; and
  - f) harvesting the recombinant protein from the bacterial strain, thereby producing the immunoprotective polypeptide.

4. A method of vaccinating an animal in need thereof against *D. immitis*-related diseases, comprising: administering the vaccine of claim 2 to the animal, wherein the animal is protected against *D. immitis*-related diseases.

5. The method of claim 4, wherein the animal is administered about 1 ml of the vaccine, and/or the animal is administered 2 subcutaneous doses of the vaccine; and/or the 2 doses of the vaccine are administered at a 21-day interval.

6. The method of claim 4, wherein the vaccine further comprises additional antigens that provide immunity against additional pathogens.

7. The method of claim 6, wherein the additional antigens are selected from canine parvovirus (CPV), canine parainfluenza virus (CPi2), canine distemper virus (CDV), adenovirus, herpesvirus, rabies, canine coronavirus, and combinations thereof.

* * * * *

SEQUENCE LISTING

```
<160> NUMBER OF SEQ ID NOS: 58

<210> SEQ ID NO 1
<211> LENGTH: 21
<212> TYPE: PRT
<213> ORGANISM: Artificial Sequence
<220> FEATURE:
<223> OTHER INFORMATION: Murine IgK chain leader

<400> SEQUENCE: 1
```

```
Met Glu Thr Asp Thr Leu Leu Leu Trp Val Leu Leu Leu Trp Val Pro
1               5                   10                  15

Gly Ser Thr Gly Asp
            20


<210> SEQ ID NO 2
<211> LENGTH: 10
<212> TYPE: PRT
<213> ORGANISM: Artificial Sequence
<220> FEATURE:
<223> OTHER INFORMATION: C-myc tag

<400> SEQUENCE: 2

Glu Gln Lys Leu Ile Ser Glu Glu Asp Leu
1               5                   10


<210> SEQ ID NO 3
<211> LENGTH: 361
<212> TYPE: PRT
<213> ORGANISM: Artificial Sequence
<220> FEATURE:
<223> OTHER INFORMATION: Serpin segment of SSFI chimera

<400> SEQUENCE: 3

Thr Asp His Ala Gln Phe Asn Phe Thr Val Ser Leu Leu Gln Lys Val
1               5                   10                  15

Ala Gln Lys Asp Lys Ser Ile Ile Leu Ser Pro Leu Ser Val Ser Thr
            20                  25                  30

Ser Leu Phe Met Ile Tyr Leu Ala Ala Asp Gly Lys Thr Lys Gln Gln
        35                  40                  45

Leu Glu Asp Val Leu Gly Gly Thr Ala Ser Thr Glu Glu Val Arg Leu
    50                  55                  60

His Phe Ala Lys Leu Leu Ala Thr Asn Glu Asn Val Glu Asn Glu Asn
65                  70                  75                  80

Tyr Thr Leu Arg Leu Ala Asn Arg Phe Tyr Val Arg Gln Glu Phe Arg
                85                  90                  95

Thr Lys Glu Ser Phe Thr Arg Thr Leu Gln Tyr Tyr Tyr Asn Glu Lys
            100                 105                 110

Leu Tyr Asn Phe Asn Tyr Gly Glu Lys Tyr Lys Phe Val Gln Glu Ile
        115                 120                 125

Asn Lys Trp Ile Ser Gly Lys Thr Asn Asn Lys Ile Thr Glu Leu Ile
    130                 135                 140

Thr Ala Asp Ser Val Ser Asp Asp Ile Lys Met Leu Leu Leu Asn Ala
145                 150                 155                 160

Ile His Phe Ser Gly Thr Trp Glu Thr Gln Phe Met Lys Asp Val Thr
                165                 170                 175

Lys Gln Lys Asp Phe Tyr Ile Ser Glu His Lys Thr Lys Lys Val Pro
            180                 185                 190

Met Met Met Thr Thr Tyr Ala Ile Pro Tyr Phe Glu Asp Asp Phe Val
        195                 200                 205

Gln Val Val Lys Met Pro Tyr Val Gly Asn Glu Ile Glu Met Val Phe
    210                 215                 220

Ile Leu Pro Lys Ile Arg Tyr Gly Leu Ser Asn Val Leu Gln Asn Leu
225                 230                 235                 240

Thr Gly Ser Asp Leu Val Arg Tyr Ile His Asn Ala Lys Pro Thr Leu
                245                 250                 255

Ser Ser Leu Lys Ile Pro Arg Phe Glu Leu Lys Gly Lys Leu Asn Leu
```

-continued

```
            260                 265                 270

Lys Lys Thr Leu Ala Asn Ile Gly Ile Thr Asp Ala Phe Ser Arg Ala
        275                 280                 285

Ala Asn Phe Lys Glu Leu Thr Asn Asp Glu Ile Ser Val Gly Ser Ile
    290                 295                 300

Ile His Ala Gly Phe Ile Ala Val Asp Glu Lys Gly Thr Glu Ser Ala
305                 310                 315                 320

Ala Ala Thr Lys Val Glu Leu Ile Asp Arg Ile Ser Ala Val Lys Tyr
                325                 330                 335

Phe His Ala Asp Gln Pro Phe Leu Phe Ala Ile Val Arg Gly Leu Lys
            340                 345                 350

Thr Ile Leu Phe Ala Gly Gln Phe Ala
        355                 360


<210> SEQ ID NO 4
<211> LENGTH: 235
<212> TYPE: PRT
<213> ORGANISM: Artificial Sequence
<220> FEATURE:
<223> OTHER INFORMATION: Syntenin segment of SSFI chimera

<400> SEQUENCE: 4

Pro Leu Tyr Pro Thr Phe Glu Asp Leu Leu Val Asp Gln Tyr His Tyr
1               5                   10                  15

Glu Gln Tyr Asp Asn Tyr Ser Ser His Asp Ser Pro Pro Val His Ser
            20                  25                  30

Tyr Ala Lys Pro Ser Ala Pro Leu Tyr Asp Ser Ser Ser Ser Thr Ile
        35                  40                  45

Ser Ala Gly Arg Ile Tyr Glu Ala Ile Asp Glu Asn Thr Val Ser Pro
    50                  55                  60

Val Leu Ser Lys Met Ser Gly Tyr Pro Ala Leu Pro Ser Tyr Tyr Glu
65                  70                  75                  80

Ser Ile Ser Gln Pro Gln His Ala Ser Thr Leu Lys Leu Ser Glu Gln
                85                  90                  95

Leu Pro Glu Val Arg Leu Pro Asn Leu His Leu Pro Gln Ser Ile Ala
            100                 105                 110

Val Gln Pro Tyr Met Ser Asn Arg Leu Val Ser Leu Glu Asn Asp Trp
        115                 120                 125

Ile Ile Ala Pro Ile Thr Leu Gln Cys Pro Gly Leu Ala Lys Thr Asn
    130                 135                 140

Leu Thr His Gly Val Arg Lys Val Ile Leu Asn Arg Thr Lys Asp Lys
145                 150                 155                 160

Lys Tyr Gly Leu Arg Met Arg Ala Val Asn Gln Gly Val Phe Val Gln
                165                 170                 175

Leu Val Ala Glu Gly Ser Pro Ala Ala Ala Ala Gly Ile Arg Phe Gly
            180                 185                 190

Asp Gln Leu Leu Asn Leu Asn Gly Thr Glu Val Leu Gly Met Thr Gly
        195                 200                 205

Gln Lys Ala Met Asp Ile Met Lys Lys Ser Lys Arg Glu Val Ile Leu
    210                 215                 220

Ile Leu Arg Asp Arg Pro Leu Ala Arg Thr Ile
225                 230                 235


<210> SEQ ID NO 5
<211> LENGTH: 333
<212> TYPE: PRT
```

-continued

```
<213> ORGANISM: Artificial Sequence
<220> FEATURE:
<223> OTHER INFORMATION: Fukutin segment of SSFI chimera

<400> SEQUENCE: 5

Asn His Thr Glu Glu Val Thr Lys Tyr Ile Ala Val Thr Asp Lys Phe
1               5                   10                  15

Ser Asn Ile Thr Tyr Ser Asn Phe His Leu Glu Lys Lys Glu Leu Leu
            20                  25                  30

Tyr Leu Lys Gln Phe Tyr His Leu Phe Trp Leu Pro Gly Ile Asn Pro
        35                  40                  45

Ser Lys Tyr Ile Phe Gly Thr Tyr Asp Asn Ser Lys Asn Leu Leu Ala
    50                  55                  60

Ile Gly Asn Ile Ile Ile Tyr Arg Met Val Asn Ser Ser Asn Glu Asp
65                  70                  75                  80

Tyr Val Arg Phe Val Tyr Asp Glu Asp His Arg Ala Ala Tyr Gly Leu
                85                  90                  95

His Ala Val Lys Lys His Ile Phe Glu Arg Glu Thr Trp Val Pro Val
            100                 105                 110

Asn Lys Glu Glu Phe Leu Arg Lys Trp Ser Ser Gly Arg Phe Leu Asp
        115                 120                 125

Cys Ile Arg Leu Asn Ile Ser Thr Ser Trp Thr Lys Ser Val Ile Pro
    130                 135                 140

His Ser Tyr Val Asn Asn Met Ala Thr Phe Arg Asp Phe Ile Glu Ser
145                 150                 155                 160

Phe Lys Ala Ile Pro Phe Leu Phe Gly Gly Thr Leu Leu Gly Trp Tyr
                165                 170                 175

Arg Glu Cys Ser Phe Ile Lys Asp Thr Thr Asp Val Asp Met Ala Met
            180                 185                 190

Lys Ile Thr Ser Leu Asp Leu Arg Met Leu Lys Asn Met Glu Lys Ser
        195                 200                 205

Asn Asp Phe Arg Leu Phe Trp Ile Leu Gly Lys Ile Asn Asp Ser Leu
    210                 215                 220

Glu Val Ser Val Tyr Ser Ala Asn Ile Lys Ile Asp Leu Phe Phe Leu
225                 230                 235                 240

Tyr Glu Asn Lys Asp Phe Ala Trp Val Gly Gly Met Ile Val Ser Lys
                245                 250                 255

Arg Lys Lys Phe Arg Trp Val Tyr Pro Pro Ile Ser Gln Ile Cys Thr
            260                 265                 270

Gly Asp Leu Leu Gly Arg Leu Phe His Val Pro Cys Asn Val Glu Glu
        275                 280                 285

Val Leu Lys Ala Asp Tyr Gly Asp Trp Arg Ile Pro Tyr Pro Thr Ala
    290                 295                 300

Asn Phe Thr Trp Tyr Lys Thr His Lys Asn Ile His Glu Ala Gly Tyr
305                 310                 315                 320

Trp Ser Glu Asn Glu Trp Asn Asp Thr Tyr Lys Ile Phe
                325                 330


<210> SEQ ID NO 6
<211> LENGTH: 88
<212> TYPE: PRT
<213> ORGANISM: Artificial Sequence
<220> FEATURE:
<223> OTHER INFORMATION: IF1 segment of SSFI chimera

<400> SEQUENCE: 6
```

-continued

```
Val Lys Asp Glu Lys Ser Lys Thr Leu Phe Glu Val Glu Gly Ala Val
1               5                   10                  15

Thr Ala Leu Leu Pro Ala Ala Glu Phe Arg Val Lys Leu Asp Asn Glu
            20                  25                  30

His Glu Ile Ile Cys His Val Ser Gly Lys Val Arg Arg Ser Lys Ile
        35                  40                  45

Arg Ile Ile Ile Gly Asp Arg Val Leu Val Glu Met Ser Ile Tyr Asp
    50                  55                  60

Arg Asn Ala Lys Lys Gly Arg Ile Ile Arg Arg Leu Lys Gly Thr Ser
65                  70                  75                  80

Asp Arg Thr Ile Ser Lys Glu Gln
                85


<210> SEQ ID NO 7
<211> LENGTH: 1058
<212> TYPE: PRT
<213> ORGANISM: Artificial Sequence
<220> FEATURE:
<223> OTHER INFORMATION: SSFI Chimera with 5' Murine IgK chain leader
      and 3' C-myc tag

<400> SEQUENCE: 7

Met Glu Thr Asp Thr Leu Leu Leu Trp Val Leu Leu Leu Trp Val Pro
1               5                   10                  15

Gly Ser Thr Gly Asp Thr Asp His Ala Gln Phe Asn Phe Thr Val Ser
            20                  25                  30

Leu Leu Gln Lys Val Ala Gln Lys Asp Lys Ser Ile Ile Leu Ser Pro
        35                  40                  45

Leu Ser Val Ser Thr Ser Leu Phe Met Ile Tyr Leu Ala Ala Asp Gly
    50                  55                  60

Lys Thr Lys Gln Gln Leu Glu Asp Val Leu Gly Gly Thr Ala Ser Thr
65                  70                  75                  80

Glu Glu Val Arg Leu His Phe Ala Lys Leu Leu Ala Thr Asn Glu Asn
                85                  90                  95

Val Glu Asn Glu Asn Tyr Thr Leu Arg Leu Ala Asn Arg Phe Tyr Val
            100                 105                 110

Arg Gln Glu Phe Arg Thr Lys Glu Ser Phe Thr Arg Thr Leu Gln Tyr
        115                 120                 125

Tyr Tyr Asn Glu Lys Leu Tyr Asn Phe Asn Tyr Gly Glu Lys Tyr Lys
    130                 135                 140

Phe Val Gln Glu Ile Asn Lys Trp Ile Ser Gly Lys Thr Asn Asn Lys
145                 150                 155                 160

Ile Thr Glu Leu Ile Thr Ala Asp Ser Val Ser Asp Asp Ile Lys Met
                165                 170                 175

Leu Leu Leu Asn Ala Ile His Phe Ser Gly Thr Trp Glu Thr Gln Phe
            180                 185                 190

Met Lys Asp Val Thr Lys Gln Lys Asp Phe Tyr Ile Ser Glu His Lys
        195                 200                 205

Thr Lys Lys Val Pro Met Met Met Thr Thr Tyr Ala Ile Pro Tyr Phe
    210                 215                 220

Glu Asp Asp Phe Val Gln Val Val Lys Met Pro Tyr Val Gly Asn Glu
225                 230                 235                 240

Ile Glu Met Val Phe Ile Leu Pro Lys Ile Arg Tyr Gly Leu Ser Asn
                245                 250                 255

Val Leu Gln Asn Leu Thr Gly Ser Asp Leu Val Arg Tyr Ile His Asn
            260                 265                 270
```

-continued

```
Ala Lys Pro Thr Leu Ser Ser Leu Lys Ile Pro Arg Phe Glu Leu Lys
        275                 280                 285

Gly Lys Leu Asn Leu Lys Lys Thr Leu Ala Asn Ile Gly Ile Thr Asp
    290                 295                 300

Ala Phe Ser Arg Ala Ala Asn Phe Lys Glu Leu Thr Asn Asp Glu Ile
305                 310                 315                 320

Ser Val Gly Ser Ile Ile His Ala Gly Phe Ile Ala Val Asp Glu Lys
                325                 330                 335

Gly Thr Glu Ser Ala Ala Ala Thr Lys Val Glu Leu Ile Asp Arg Ile
            340                 345                 350

Ser Ala Val Lys Tyr Phe His Ala Asp Gln Pro Phe Leu Phe Ala Ile
        355                 360                 365

Val Arg Gly Leu Lys Thr Ile Leu Phe Ala Gly Gln Phe Ala Gly Ser
    370                 375                 380

Ser Gly Pro Leu Tyr Pro Thr Phe Glu Asp Leu Leu Val Asp Gln Tyr
385                 390                 395                 400

His Tyr Glu Gln Tyr Asp Asn Tyr Ser Ser His Asp Ser Pro Pro Val
                405                 410                 415

His Ser Tyr Ala Lys Pro Ser Ala Pro Leu Tyr Asp Ser Ser Ser Ser
            420                 425                 430

Thr Ile Ser Ala Gly Arg Ile Tyr Glu Ala Ile Asp Glu Asn Thr Val
        435                 440                 445

Ser Pro Val Leu Ser Lys Met Ser Gly Tyr Pro Ala Leu Pro Ser Tyr
    450                 455                 460

Tyr Glu Ser Ile Ser Gln Pro Gln His Ala Ser Thr Leu Lys Leu Ser
465                 470                 475                 480

Glu Gln Leu Pro Glu Val Arg Leu Pro Asn Leu His Leu Pro Gln Ser
                485                 490                 495

Ile Ala Val Gln Pro Tyr Met Ser Asn Arg Leu Val Ser Leu Glu Asn
            500                 505                 510

Asp Trp Ile Ile Ala Pro Ile Thr Leu Gln Cys Pro Gly Leu Ala Lys
        515                 520                 525

Thr Asn Leu Thr His Gly Val Arg Lys Val Ile Leu Asn Arg Thr Lys
    530                 535                 540

Asp Lys Lys Tyr Gly Leu Arg Met Arg Ala Val Asn Gln Gly Val Phe
545                 550                 555                 560

Val Gln Leu Val Ala Glu Gly Ser Pro Ala Ala Ala Ala Gly Ile Arg
                565                 570                 575

Phe Gly Asp Gln Leu Leu Asn Leu Asn Gly Thr Glu Val Leu Gly Met
            580                 585                 590

Thr Gly Gln Lys Ala Met Asp Ile Met Lys Lys Ser Lys Arg Glu Val
        595                 600                 605

Ile Leu Ile Leu Arg Asp Arg Pro Leu Ala Arg Thr Ile Gly Ser Ser
    610                 615                 620

Gly Asn His Thr Glu Glu Val Thr Lys Tyr Ile Ala Val Thr Asp Lys
625                 630                 635                 640

Phe Ser Asn Ile Thr Tyr Ser Asn Phe His Leu Glu Lys Lys Glu Leu
                645                 650                 655

Leu Tyr Leu Lys Gln Phe Tyr His Leu Phe Trp Leu Pro Gly Ile Asn
            660                 665                 670

Pro Ser Lys Tyr Ile Phe Gly Thr Tyr Asp Asn Ser Lys Asn Leu Leu
        675                 680                 685
```

```
Ala Ile Gly Asn Ile Ile Ile Tyr Arg Met Val Asn Ser Ser Asn Glu
    690                 695                 700

Asp Tyr Val Arg Phe Val Tyr Asp Glu Asp His Arg Ala Ala Tyr Gly
705                 710                 715                 720

Leu His Ala Val Lys Lys His Ile Phe Glu Arg Glu Thr Trp Val Pro
                725                 730                 735

Val Asn Lys Glu Glu Phe Leu Arg Lys Trp Ser Ser Gly Arg Phe Leu
            740                 745                 750

Asp Cys Ile Arg Leu Asn Ile Ser Thr Ser Trp Thr Lys Ser Val Ile
        755                 760                 765

Pro His Ser Tyr Val Asn Asn Met Ala Thr Phe Arg Asp Phe Ile Glu
    770                 775                 780

Ser Phe Lys Ala Ile Pro Phe Leu Phe Gly Gly Thr Leu Leu Gly Trp
785                 790                 795                 800

Tyr Arg Glu Cys Ser Phe Ile Lys Asp Thr Thr Asp Val Asp Met Ala
                805                 810                 815

Met Lys Ile Thr Ser Leu Asp Leu Arg Met Leu Lys Asn Met Glu Lys
            820                 825                 830

Ser Asn Asp Phe Arg Leu Phe Trp Ile Leu Gly Lys Ile Asn Asp Ser
        835                 840                 845

Leu Glu Val Ser Val Tyr Ser Ala Asn Ile Lys Ile Asp Leu Phe Phe
    850                 855                 860

Leu Tyr Glu Asn Lys Asp Phe Ala Trp Val Gly Gly Met Ile Val Ser
865                 870                 875                 880

Lys Arg Lys Lys Phe Arg Trp Val Tyr Pro Pro Ile Ser Gln Ile Cys
                885                 890                 895

Thr Gly Asp Leu Leu Gly Arg Leu Phe His Val Pro Cys Asn Val Glu
            900                 905                 910

Glu Val Leu Lys Ala Asp Tyr Gly Asp Trp Arg Ile Pro Tyr Pro Thr
        915                 920                 925

Ala Asn Phe Thr Trp Tyr Lys Thr His Lys Asn Ile His Glu Ala Gly
    930                 935                 940

Tyr Trp Ser Glu Asn Glu Trp Asn Asp Thr Tyr Lys Ile Phe Gly Ser
945                 950                 955                 960

Ser Gly Val Lys Asp Glu Lys Ser Lys Thr Leu Phe Glu Val Glu Gly
                965                 970                 975

Ala Val Thr Ala Leu Leu Pro Ala Ala Glu Phe Arg Val Lys Leu Asp
            980                 985                 990

Asn Glu His Glu Ile Ile Cys His  Val Ser Gly Lys Val  Arg Arg Ser
        995                 1000                1005

Lys Ile  Arg Ile Ile Ile Gly  Asp Arg Val Leu Val  Glu Met Ser
    1010                1015                1020

Ile Tyr  Asp Arg Asn Ala Lys  Lys Gly Arg Ile Ile  Arg Arg Leu
    1025                1030                1035

Lys Gly  Thr Ser Asp Arg Thr  Ile Ser Lys Glu Gln  Lys Leu Ile
    1040                1045                1050

Ser Glu  Glu Asp Leu
    1055
```

<210> SEQ ID NO 8
<211> LENGTH: 1083
<212> TYPE: DNA
<213> ORGANISM: Artificial Sequence
<220> FEATURE:
<223> OTHER INFORMATION: Serpin segment of SSFI chimera

<400> SEQUENCE: 8
acggatcatg cacagttcaa cttcacggtg agcctcctcc agaaagtcgc acagaaggac 60
aagagtatca tactgtcccc actttctgtt agtacttcgc tgttcatgat ctacctagca 120
gctgacggca agactaagca gcaactggag gacgtattag gtggtactgc atctaccgag 180
gaggtccgct tgcacttcgc caaactgctc gccaccaatg agaacgttga aaacgagaac 240
tacacactca ggctcgctaa tcgattttat gtcagacagg agttccgtac caaggagtcc 300
tttactagaa ccttgcaata ctactacaac gagaaactct acaacttcaa ttatggcgag 360
aaatacaagt tcgtccagga aatcaacaag tggattagcg gtaaaactaa taacaagatt 420
acggaattga taaccgcgga ttccgtttca gacgacatca agatgctcct gctaaacgct 480
atccactttt ccggtacttg ggagactcaa tttatgaaag atgtcaccaa gcagaaagat 540
ttctacatct cggaacacaa gaccaagaag gtgcctatga tgatgacgac ctacgccata 600
ccatatttcg aggacgactt tgtgcaagtg gtgaagatgc catacgtggg aaacgagatc 660
gaaatggttt tcattttacc gaagatcaga tatggcttgt ccaacgtcct gcaaaactta 720
acgggatctg acctggtgcg ctacattcac aatgcgaagc ctaccctgtc gagcttgaag 780
atacctaggt tcgagctgaa gggcaagctg aatctcaaga aaaccttggc taatataggc 840
attactgacg ccttctctcg tgctgccaac ttcaaagagc ttacaaacga cgaaatttca 900
gtgggctcga tcattcatgc aggattcatc gctgtggatg agaagggtac cgagtcagcc 960
gcggcaacaa aagtcgagct catagacagg atcagcgccg taaagtactt ccacgcggat 1020
caaccattcc tattcgctat tgtccgagga ctaaagacaa tcttatttgc cggtcaattc 1080
gct 1083

<210> SEQ ID NO 9
<211> LENGTH: 705
<212> TYPE: DNA
<213> ORGANISM: Artificial Sequence
<220> FEATURE:
<223> OTHER INFORMATION: Syntenin segment of SSFI chimera

<400> SEQUENCE: 9
cctctttatc ccactttcga ggatctgctg gtcgaccagt atcactacga acagtacgac 60
aactacagca gccatgatag cccacccgtt cattcctatg caaaacccag tgccccactt 120
tacgactcaa gctcatctac catttccgct ggccgtattt acgaagcgat agatgagaac 180
accgtgagtc ctgtcctgag caaaatgagc ggttaccctg ctctcccgtc atactacgaa 240
tcaatctcac aacctcaaca tgcctctaca ctgaaattgt cggagcaact cccagaagtc 300
agattaccca atttgcattt gccacagtct attgcggtac agccgtatat gtcaaaccgt 360
cttgtcagct tggaaaacga ttggatcatc gctccgataa cactccagtg tcccggcctg 420
gccaagacaa atctcaccca cggtgttcgt aaggttatcc tcaatagaac caaagacaag 480
aagtatggac tgcgtatgag ggcggtaaac caaggcgtat tcgtacagct ggtcgcagaa 540
ggttctcccg cagctgcggc gggcatccgt ttcggtgacc agcttctgaa cttgaatggt 600
actgaagtac taggcatgac tggacagaaa gcaatggaca ttatgaagaa gagcaagcgc 660
gaggtgattc ttatcctgag ggatcgtcct ctagcccgca ctatt 705

<210> SEQ ID NO 10
<211> LENGTH: 999
<212> TYPE: DNA

-continued

<213> ORGANISM: Artificial Sequence
<220> FEATURE:
<223> OTHER INFORMATION: Fukutin segment of SSFI chimera

<400> SEQUENCE: 10

```
aatcacaccg aagaggtgac aaaatacatt gctgtgacgg ataagttcag caacatcact     60

tactccaact ttcacctgga gaagaaagag cttttgtatc tgaaacaatt ttaccatttg    120

ttctggctac ccggtataaa tccctctaaa tacattttcg gcacatacga caactccaag    180

aacttgctgg caataggaaa cataatcatc tatcgcatgg tgaattcctc caatgaggac    240

tacgtgcgat tcgtatacga cgaagatcac cgcgctgctt acggactcca cgccgttaag    300

aagcacatct ttgagagaga aacctgggta cctgtgaaca aggaagagtt cctaaggaag    360

tggtcatctg gaaggttcct ggattgcatt cgcctaaata tcagtacgag ctggaccaaa    420

agcgtcatcc cgcactccta cgtaaacaat atggctacat tcagagactt catcgaatcc    480

ttcaaggcta tccccttct tttcggtggt actctgctcg gatggtatcg tgagtgttcg    540

tttatcaagg acaccacaga cgtcgacatg gcgatgaaaa ttacctccct ggacctccgc    600

atgttgaaga acatggagaa gagtaacgac ttccgcctct tttggatctt gggcaagatt    660

aacgatagtt tggaagtgtc ggtttacagt gccaacatta agatcgatct tttcttcttg    720

tacgaaaaca aagacttcgc ctgggttggc ggaatgattg tgtctaaacg caagaaattc    780

agatgggtct atccaccaat ctctcagatt tgcacaggag atctgttagg tcgccttttc    840

cacgtcccgt gcaacgtaga ggaagtgttg aaggccgatt acggtgattg gcgtatccct    900

tatcctacag ccaacttcac gtggtacaaa acgcacaaga acatccatga ggctggatac    960

tggtcagaaa acgaatggaa cgatacatac aagatcttt                          999
```

<210> SEQ ID NO 11
<211> LENGTH: 258
<212> TYPE: DNA
<213> ORGANISM: Artificial Sequence
<220> FEATURE:
<223> OTHER INFORMATION: IF1 segment of SSFI chimera

<400> SEQUENCE: 11

```
gtgaaggacg aaaagtctaa gactctgttt gaggttgaag gagctgttac agcgttactg     60

cccgctgccg aattccgtgt caaactggac aatgagcacg agatcatctg ccatgtctcc    120

ggtaaagtta gacgctctaa gatacgcatc atcatcggcg acagggtact cgtggaaatg    180

tccatctatg atcgcaacgc taagaaaggc aggatcattc gtcgactgaa aggaactagt    240

gaccgcacta tctcaaag                                                  258
```

<210> SEQ ID NO 12
<211> LENGTH: 3174
<212> TYPE: DNA
<213> ORGANISM: Artificial Sequence
<220> FEATURE:
<223> OTHER INFORMATION: SSFI Chimera with 5' Murine IgK chain leader
      and 3' C-myc tag

<400> SEQUENCE: 12

```
atggaaaccg acacgttgct tttatgggtg ttactcttat gggtgcccgg aagtacgggt     60

gacacggatc atgcacagtt caacttcacg gtgagcctcc tccagaaagt cgcacagaag    120

gacaagagta tcatactgtc cccactttct gttagtactt cgctgttcat gatctaccta    180

gcagctgacg gcaagactaa gcagcaactg gaggacgtat taggtggtac tgcatctacc    240
```

-continued

```
gaggaggtcc gcttgcactt cgccaaactg ctcgccacca atgagaacgt tgaaaacgag    300
aactacacac tcaggctcgc taatcgattt tatgtcagac aggagttccg taccaaggag    360
tcctttacta gaaccttgca atactactac aacgagaaac tctacaactt caattatggc    420
gagaaataca agttcgtcca ggaaatcaac aagtggatta gcggtaaaac taataacaag    480
attacggaat tgataaccgc ggattccgtt tcagacgaca tcaagatgct cctgctaaac    540
gctatccact tttccggtac ttgggagact caatttatga aagatgtcac caagcagaaa    600
gatttctaca tctcggaaca caagaccaag aaggtgccta tgatgatgac gacctacgcc    660
ataccatatt tcgaggacga ctttgtgcaa gtggtgaaga tgccatacgt gggaaacgag    720
atcgaaatgg ttttcatttt accgaagatc agatatggct tgtccaacgt cctgcaaaac    780
ttaacgggat ctgacctggt gcgctacatt cacaatgcga agcctaccct gtcgagcttg    840
aagataccta ggttcgagct gaagggcaag ctgaatctca agaaaacctt ggctaatata    900
ggcattactg acgccttctc tcgtgctgcc aacttcaaag agcttacaaa cgacgaaatt    960
tcagtgggct cgatcattca tgcaggattc atcgctgtgg atgagaaggg taccgagtca   1020
gccgcggcaa caaaagtcga gctcatagac aggatcagcg ccgtaaagta cttccacgcg   1080
gatcaaccat tcctattcgc tattgtccga ggactaaaga caatcttatt tgccggtcaa   1140
ttcgctggtt cgagtggtcc tctttatccc actttcgagg atctgctggt cgaccagtat   1200
cactacgaac agtacgacaa ctacagcagc catgatagcc cacccgttca ttcctatgca   1260
aaacccagtg ccccacttta cgactcaagc tcatctacca tttccgctgg ccgtatttac   1320
gaagcgatag atgagaacac cgtgagtcct gtcctgagca aatgagcggg ttaccctgct   1380
ctcccgtcat actacgaatc aatctcacaa cctcaacatg cctctacact gaaattgtcg   1440
gagcaactcc cagaagtcag attacccaat ttgcatttgc cacagtctat tgcggtacag   1500
ccgtatatgt caaaccgtct tgtcagcttg gaaaacgatt ggatcatcgc tccgataaca   1560
ctccagtgtc ccggcctggc caagacaaat ctcacccacg gtgttcgtaa ggttatcctc   1620
aatagaacca aagacaagaa gtatggactg cgtatgaggg cggtaaacca aggcgtattc   1680
gtacagctgg tcgcagaagg ttctcccgca gctgcggcgg gcatccgttt cggtgaccag   1740
cttctgaact tgaatggtac tgaagtacta ggcatgactg gacagaaagc aatggacatt   1800
atgaagaaga gcaagcgcga ggtgattctt atcctgaggg atcgtcctct agcccgcact   1860
attggttcgt caggcaatca caccgaagag gtgacaaaat acattgctgt gacggataag   1920
ttcagcaaca tcacttactc caactttcac ctggagaaga aagagctttt gtatctgaaa   1980
caattttacc atttgttctg gctacccggt ataaatccct ctaaatacat tttcggcaca   2040
tacgacaact ccaagaactt gctggcaata ggaaacataa tcatctatcg catggtgaat   2100
tcctccaatg aggactacgt gcgattcgta tacgacgaag atcaccgcgc tgcttacgga   2160
ctccacgccg ttaagaagca catctttgag agagaaacct gggtacctgt gaacaaggaa   2220
gagttcctaa ggaagtggtc atctggaagg ttcctggatt gcattcgcct aaatatcagt   2280
acgagctgga ccaaaaagcgt catcccgcac tcctacgtaa acaatatggc tacattcaga   2340
gacttcatcg aatccttcaa ggctatcccc tttcttttcg gtggtactct gctcggatgg   2400
tatcgtgagt gttcgtttat caaggacacc acagacgtcg acatggcgat gaaaattacc   2460
tccctggacc tccgcatgtt gaagaacatg gagaagagta acgacttccg cctcttttgg   2520
atcttgggca agattaacga tagtttggaa gtgtcggttt acagtgccaa cattaagatc   2580
gatcttttct tcttgtacga aaacaaagac ttcgcctggg ttggcggaat gattgtgtct   2640
```

```
aaacgcaaga aattcagatg ggtctatcca ccaatctctc agatttgcac aggagatctg   2700

ttaggtcgcc ttttccacgt cccgtgcaac gtagaggaag tgttgaaggc cgattacggt   2760

gattggcgta tcccttatcc tacagccaac ttcacgtggt acaaaaacgca caagaacatc   2820

catgaggctg gatactggtc agaaaacgaa tggaacgata catacaagat ctttggttcc   2880

tcaggtgtga aggacgaaaa gtctaagact ctgtttgagg ttgaaggagc tgttacagcg   2940

ttactgcccg ctgccgaatt ccgtgtcaaa ctggacaatg agcacgagat catctgccat   3000

gtctccggta aagttagacg ctctaagata cgcatcatca tcggcgacag ggtactcgtg   3060

gaaatgtcca tctatgatcg caacgctaag aaaggcagga tcattcgtcg actgaaagga   3120

actagtgacc gcactatctc aaaggaacag aagctcatct cggaggaaga tctc         3174


<210> SEQ ID NO 13
<211> LENGTH: 471
<212> TYPE: PRT
<213> ORGANISM: Artificial Sequence
<220> FEATURE:
<223> OTHER INFORMATION: M1 segment of M1-UDP-Exp2-IF1-GST (MUEIG)
      chimera

<400> SEQUENCE: 13

Glu Asn Trp Gly Leu Val Ile Phe Gln Lys Glu Met Phe Leu Leu Asp
1               5                   10                  15

Ser Leu Leu Glu Ser Asn Ala Asn Met Thr Val Asp Leu Leu Ala Glu
            20                  25                  30

Gln Tyr Asp Ile Glu Lys Ile Ile Thr His Glu Leu Val His Gln Trp
        35                  40                  45

Phe Gly Asn Leu Val Thr Ile Asn Asp Trp Ser Glu Leu Trp Ile Ser
    50                  55                  60

Glu Gly Phe Ala Ser Tyr Tyr Ala Asn Asp Phe Leu Lys Lys Gln Arg
65                  70                  75                  80

Pro Ile Leu Ala Ile Asn Glu Tyr Phe Leu Arg Leu Ser Gln Leu Leu
                85                  90                  95

Ser Arg Gln Thr Ser Asn Glu Lys Met Pro Leu Val Lys Arg Phe Arg
            100                 105                 110

Thr Glu Ala Glu Val Glu Lys Ala Phe Asn Pro Tyr His Leu Tyr Thr
        115                 120                 125

Lys Gly Ala Ala Ile Val Lys Met Met Cys Asp Leu Val Gly Glu Asn
    130                 135                 140

Asn Phe Arg Glu Gly Val Arg Arg Phe Leu Lys Thr Asn Ala Tyr Lys
145                 150                 155                 160

Ser Val Gly Arg Ser Ala Leu Trp Lys Ala Met Pro Ile Tyr Thr Lys
                165                 170                 175

His Gly Leu Glu Asn Arg Lys Leu Glu Asn Val Ile Glu Pro Trp Leu
            180                 185                 190

Ile Asn Asp Gly Met Pro Glu Val Met Val Ser Arg Asn Tyr Asn Tyr
        195                 200                 205

Gly Thr Ile His Leu Ile Pro Arg Leu Ser Asp Gln Asn Arg Tyr Ile
    210                 215                 220

Ile Tyr Leu Arg Asp Val Ser Tyr Asp Val Lys Asn Ser Asn Glu Ser
225                 230                 235                 240

Ile Lys Lys Met Lys Arg Lys Lys Trp Met Asp Lys Ile Pro Ile Arg
                245                 250                 255

Ser Arg Met Lys Phe Arg Lys Thr Gly Arg Ser Lys Lys Thr Glu Val
```

```
            260                 265                 270

Ala Asn Asp Glu Glu Val Ser Ser Phe Phe Tyr Phe Asp Phe Ile Asn
        275                 280                 285

Asn Met Leu Pro Asn Ser Arg Lys Glu Val Lys Leu Lys Gln Thr Ile
    290                 295                 300

Gly Gly Gly Asn Pro Val Gly Arg Arg Lys Lys Glu Arg Arg His Arg
305                 310                 315                 320

Lys Ile Asn Glu Lys Trp Arg Ser Ser Gln Glu Gln Gln Phe Trp Ser
                325                 330                 335

Ile Pro Phe Thr Tyr Gln Leu Ser Ser Lys Thr Asn Phe Phe Gly Asp
            340                 345                 350

Thr Ile Arg Glu Leu Trp Leu His Asn Lys Thr Val Val Phe Met Asp
        355                 360                 365

Lys Lys Ala Gln Ala Ser Ala Thr Leu Leu Ala Asn Val Asn Trp Lys
    370                 375                 380

Tyr Pro Tyr Arg Val Asn Tyr Asp Ile Glu Asn Trp Lys Met Leu Ala
385                 390                 395                 400

Arg Leu Leu His Glu Asn His Leu Ser Ile Pro Leu Tyr Ser Arg Ile
                405                 410                 415

Gln Leu Ile Phe Asp Ser Glu Phe Tyr Leu Lys Gln Ser Asn Val Pro
            420                 425                 430

Glu Val Tyr Leu Tyr Ile Leu Ser Tyr Leu Thr Lys Glu Asn Asp Val
        435                 440                 445

Gly Leu Leu Leu Phe Gly Leu Asp Ala Leu Tyr Arg Phe Phe Asp Met
    450                 455                 460

Phe Arg Gly Ser Ser Ile Asn
465                 470


<210> SEQ ID NO 14
<211> LENGTH: 248
<212> TYPE: PRT
<213> ORGANISM: Artificial Sequence
<220> FEATURE:
<223> OTHER INFORMATION: UDP segment of MUEIG chimera

<400> SEQUENCE: 14

Leu Leu His Ala Ala Leu Leu Ser Met Leu Leu Glu Ser Ile Phe Ser
1               5                   10                  15

Tyr Lys Ile Leu Ile Phe Ser Pro Arg Leu Ala His Ser His Ile Asn
            20                  25                  30

Phe Met Gly Ile Leu Ala Asp Val Leu Val Glu Ala Gly His Asp Ile
        35                  40                  45

Thr Ile Phe Met Pro Asp Leu Asn Pro Asp Val Ser Asn Asn Gly Ser
    50                  55                  60

Lys Leu Ala Lys Ile Val Arg Lys Thr Phe Ser Asn Thr Asn Asn Gln
65                  70                  75                  80

Ile Leu Lys Lys Asn Ser Ala Arg Glu Lys Trp Lys Lys Lys Gly Asp
                85                  90                  95

Ser Ile Leu Gln Val Tyr Arg Leu Phe Gln Gln Leu Ala Asp Ser Gln
            100                 105                 110

Arg Leu Met Cys Leu Glu His Leu Glu Asp Asp Lys Leu Ile Ser Trp
        115                 120                 125

Leu Gln Thr Glu Gln Tyr Asp Leu Gly Ile Thr Glu Gln Ile Ser Phe
    130                 135                 140

Cys Gly Tyr Ala Ile Phe Asn Arg Ile Gly Leu Asn Asn Gln Val Thr
```

```
145                 150                 155                 160

Ala Gly Ala Ile Thr Leu Met Glu Val Leu Ser Asp Pro Phe Gly Val
                165                 170                 175

Ser Ser Asn Pro Ser Tyr Val Pro Gly Gly Phe Ser Ser Lys Ala Asp
            180                 185                 190

Lys Met Asn Tyr Leu Glu Arg Leu Ala Asn Ile Ile Ile Tyr Thr Thr
        195                 200                 205

Ser Tyr Ile Leu Thr Lys Phe Val Trp Glu Pro Ala Val Gln Ser Leu
    210                 215                 220

Gln His Asn Leu Pro Asn Asn Phe Asn Tyr Ile Glu Thr Leu Lys Asn
225                 230                 235                 240

Ser Ser Leu Tyr Phe Val Asn Thr
                245


<210> SEQ ID NO 15
<211> LENGTH: 78
<212> TYPE: PRT
<213> ORGANISM: Artificial Sequence
<220> FEATURE:
<223> OTHER INFORMATION: Exp2 segment of MUEIG chimera

<400> SEQUENCE: 15

Gly Leu Ser Phe Gly Thr Ile Pro Asp Phe Gln Val Val Gln Tyr Leu
1               5                   10                  15

Pro Thr Tyr Asn Glu Thr Val Leu Leu Pro Asn Gly Thr Ile Thr Val
            20                  25                  30

Val Glu Lys Ile Glu Glu Met Arg Ile Glu His Pro Ile Phe Val Leu
        35                  40                  45

Thr Glu Arg Ile Cys Ile Ala Phe Phe Thr Ile Glu Tyr Cys Leu Arg
    50                  55                  60

Leu Phe Ala Ala Pro Arg Lys Leu Arg Phe Met Leu Lys Pro
65                  70                  75


<210> SEQ ID NO 16
<211> LENGTH: 86
<212> TYPE: PRT
<213> ORGANISM: Artificial Sequence
<220> FEATURE:
<223> OTHER INFORMATION: IF1 segment of MUEIG chimera

<400> SEQUENCE: 16

Val Lys Asp Glu Lys Ser Lys Thr Leu Phe Glu Val Glu Gly Ala Val
1               5                   10                  15

Thr Ala Leu Leu Pro Ala Ala Glu Phe Arg Val Lys Leu Asp Asn Glu
            20                  25                  30

His Glu Ile Ile Cys His Val Ser Gly Lys Val Arg Arg Ser Lys Ile
        35                  40                  45

Arg Ile Ile Ile Gly Asp Arg Val Leu Val Glu Met Ser Ile Tyr Asp
    50                  55                  60

Arg Asn Ala Lys Lys Gly Arg Ile Ile Arg Arg Leu Lys Gly Thr Ser
65                  70                  75                  80

Asp Arg Thr Ile Ser Lys
                85


<210> SEQ ID NO 17
<211> LENGTH: 207
<212> TYPE: PRT
<213> ORGANISM: Artificial Sequence
<220> FEATURE:
```

<223> OTHER INFORMATION: GST segment of MUEIG chimera

<400> SEQUENCE: 17

Ser Tyr Lys Leu Thr Tyr Phe Pro Ile Arg Gly Leu Ala Glu Pro Ile
1 5 10 15

Arg Leu Leu Leu Val Asp Gln Gly Ile Lys Phe Thr Asp Glu His Ile
20 25 30

Pro Lys Asp Asp Phe Val Ser Ile Lys Ser Gln Phe Gln Phe Gly Gln
35 40 45

Leu Pro Cys Phe Tyr Asp Gly Asp Gln Gln Ile Val Gln Ser Gly Ala
50 55 60

Ile Leu Arg His Leu Ala Arg Lys Phe Asn Leu Asn Gly Glu Asn Asn
65 70 75 80

Ala Glu Thr Ser Tyr Val Asp Met Phe Tyr Glu Gly Ile Arg Asp Leu
85 90 95

His Ser Lys Tyr Thr Arg Met Ile Tyr Glu Ala Tyr Glu Thr Gln Lys
100 105 110

Asp Pro Phe Ile Lys Asn Ile Leu Pro Gln Glu Leu Ala Lys Leu Glu
115 120 125

Lys Leu Leu Ala Thr Arg Asp Asn Gly Lys Asn Phe Ile Leu Gly Asp
130 135 140

Lys Ile Ser Phe Ala Asp Tyr Val Leu Phe Glu Glu Leu Asp Val Gln
145 150 155 160

Gln Ile Leu Asp Pro His Cys Leu Glu Lys Phe Pro Leu Leu Lys Ala
165 170 175

Phe His Gln Arg Leu Gly Asp Lys Pro Lys Ile Lys Glu Tyr Cys Ala
180 185 190

Lys Arg Asn Ala Ser Lys Met Pro Val Asn Gly Asn Gly Lys Gln
195 200 205

<210> SEQ ID NO 18
<211> LENGTH: 1137
<212> TYPE: PRT
<213> ORGANISM: Artificial Sequence
<220> FEATURE:
<223> OTHER INFORMATION: MUEIG Chimera with 5' Murine IgK chain leader and 3' C-myc tag

<400> SEQUENCE: 18

Met Glu Thr Asp Thr Leu Leu Leu Trp Val Leu Leu Leu Trp Val Pro
1 5 10 15

Gly Ser Thr Gly Asp Glu Asn Trp Gly Leu Val Ile Phe Gln Lys Glu
20 25 30

Met Phe Leu Leu Asp Ser Leu Leu Glu Ser Asn Ala Asn Met Thr Val
35 40 45

Asp Leu Leu Ala Glu Gln Tyr Asp Ile Glu Lys Ile Ile Thr His Glu
50 55 60

Leu Val His Gln Trp Phe Gly Asn Leu Val Thr Ile Asn Asp Trp Ser
65 70 75 80

Glu Leu Trp Ile Ser Glu Gly Phe Ala Ser Tyr Tyr Ala Asn Asp Phe
85 90 95

Leu Lys Lys Gln Arg Pro Ile Leu Ala Ile Asn Glu Tyr Phe Leu Arg
100 105 110

Leu Ser Gln Leu Leu Ser Arg Gln Thr Ser Asn Glu Lys Met Pro Leu
115 120 125

Val Lys Arg Phe Arg Thr Glu Ala Glu Val Glu Lys Ala Phe Asn Pro

-continued

```
    130                 135                 140

Tyr His Leu Tyr Thr Lys Gly Ala Ala Ile Val Lys Met Met Cys Asp
145                 150                 155                 160

Leu Val Gly Glu Asn Asn Phe Arg Glu Gly Val Arg Arg Phe Leu Lys
                165                 170                 175

Thr Asn Ala Tyr Lys Ser Val Gly Arg Ser Ala Leu Trp Lys Ala Met
            180                 185                 190

Pro Ile Tyr Thr Lys His Gly Leu Glu Asn Arg Lys Leu Glu Asn Val
        195                 200                 205

Ile Glu Pro Trp Leu Ile Asn Asp Gly Met Pro Glu Val Met Val Ser
    210                 215                 220

Arg Asn Tyr Asn Tyr Gly Thr Ile His Leu Ile Pro Arg Leu Ser Asp
225                 230                 235                 240

Gln Asn Arg Tyr Ile Ile Tyr Leu Arg Asp Val Ser Tyr Asp Val Lys
                245                 250                 255

Asn Ser Asn Glu Ser Ile Lys Lys Met Lys Arg Lys Lys Trp Met Asp
            260                 265                 270

Lys Ile Pro Ile Arg Ser Arg Met Lys Phe Arg Lys Thr Gly Arg Ser
        275                 280                 285

Lys Lys Thr Glu Val Ala Asn Asp Glu Glu Val Ser Ser Phe Phe Tyr
    290                 295                 300

Phe Asp Phe Ile Asn Asn Met Leu Pro Asn Ser Arg Lys Glu Val Lys
305                 310                 315                 320

Leu Lys Gln Thr Ile Gly Gly Gly Asn Pro Val Gly Arg Arg Lys Lys
                325                 330                 335

Glu Arg Arg His Arg Lys Ile Asn Glu Lys Trp Arg Ser Ser Gln Glu
            340                 345                 350

Gln Gln Phe Trp Ser Ile Pro Phe Thr Tyr Gln Leu Ser Ser Lys Thr
        355                 360                 365

Asn Phe Phe Gly Asp Thr Ile Arg Glu Leu Trp Leu His Asn Lys Thr
    370                 375                 380

Val Val Phe Met Asp Lys Lys Ala Gln Ala Ser Ala Thr Leu Leu Ala
385                 390                 395                 400

Asn Val Asn Trp Lys Tyr Pro Tyr Arg Val Asn Tyr Asp Ile Glu Asn
                405                 410                 415

Trp Lys Met Leu Ala Arg Leu Leu His Glu Asn His Leu Ser Ile Pro
            420                 425                 430

Leu Tyr Ser Arg Ile Gln Leu Ile Phe Asp Ser Glu Phe Tyr Leu Lys
        435                 440                 445

Gln Ser Asn Val Pro Glu Val Tyr Leu Tyr Ile Leu Ser Tyr Leu Thr
    450                 455                 460

Lys Glu Asn Asp Val Gly Leu Leu Leu Phe Gly Leu Asp Ala Leu Tyr
465                 470                 475                 480

Arg Phe Phe Asp Met Phe Arg Gly Ser Ser Ile Asn Gly Ser Ser Gly
                485                 490                 495

Leu Leu His Ala Ala Leu Leu Ser Met Leu Leu Glu Ser Ile Phe Ser
            500                 505                 510

Tyr Lys Ile Leu Ile Phe Ser Pro Arg Leu Ala His Ser His Ile Asn
        515                 520                 525

Phe Met Gly Ile Leu Ala Asp Val Leu Val Glu Ala Gly His Asp Ile
    530                 535                 540

Thr Ile Phe Met Pro Asp Leu Asn Pro Asp Val Ser Asn Asn Gly Ser
545                 550                 555                 560
```

-continued

```
Lys Leu Ala Lys Ile Val Arg Lys Thr Phe Ser Asn Thr Asn Asn Gln
                565                 570                 575

Ile Leu Lys Lys Asn Ser Ala Arg Glu Lys Trp Lys Lys Lys Gly Asp
            580                 585                 590

Ser Ile Leu Gln Val Tyr Arg Leu Phe Gln Gln Leu Ala Asp Ser Gln
        595                 600                 605

Arg Leu Met Cys Leu Glu His Leu Glu Asp Asp Lys Leu Ile Ser Trp
    610                 615                 620

Leu Gln Thr Glu Gln Tyr Asp Leu Gly Ile Thr Glu Gln Ile Ser Phe
625                 630                 635                 640

Cys Gly Tyr Ala Ile Phe Asn Arg Ile Gly Leu Asn Asn Gln Val Thr
                645                 650                 655

Ala Gly Ala Ile Thr Leu Met Glu Val Leu Ser Asp Pro Phe Gly Val
            660                 665                 670

Ser Ser Asn Pro Ser Tyr Val Pro Gly Gly Phe Ser Ser Lys Ala Asp
        675                 680                 685

Lys Met Asn Tyr Leu Glu Arg Leu Ala Asn Ile Ile Tyr Thr Thr
    690                 695                 700

Ser Tyr Ile Leu Thr Lys Phe Val Trp Glu Pro Ala Val Gln Ser Leu
705                 710                 715                 720

Gln His Asn Leu Pro Asn Asn Phe Asn Tyr Ile Glu Thr Leu Lys Asn
                725                 730                 735

Ser Ser Leu Tyr Phe Val Asn Thr Gly Ser Ser Gly Gly Leu Ser Phe
            740                 745                 750

Gly Thr Ile Pro Asp Phe Gln Val Val Gln Tyr Leu Pro Thr Tyr Asn
        755                 760                 765

Glu Thr Val Leu Leu Pro Asn Gly Thr Ile Thr Val Val Glu Lys Ile
    770                 775                 780

Glu Glu Met Arg Ile Glu His Pro Ile Phe Val Leu Thr Glu Arg Ile
785                 790                 795                 800

Cys Ile Ala Phe Phe Thr Ile Glu Tyr Cys Leu Arg Leu Phe Ala Ala
                805                 810                 815

Pro Arg Lys Leu Arg Phe Met Leu Lys Pro Gly Ser Ser Gly Val Lys
            820                 825                 830

Asp Glu Lys Ser Lys Thr Leu Phe Glu Val Glu Gly Ala Val Thr Ala
        835                 840                 845

Leu Leu Pro Ala Ala Glu Phe Arg Val Lys Leu Asp Asn Glu His Glu
    850                 855                 860

Ile Ile Cys His Val Ser Gly Lys Val Arg Arg Ser Lys Ile Arg Ile
865                 870                 875                 880

Ile Ile Gly Asp Arg Val Leu Val Glu Met Ser Ile Tyr Asp Arg Asn
                885                 890                 895

Ala Lys Lys Gly Arg Ile Ile Arg Arg Leu Lys Gly Thr Ser Asp Arg
            900                 905                 910

Thr Ile Ser Lys Gly Ser Ser Gly Ser Tyr Lys Leu Thr Tyr Phe Pro
        915                 920                 925

Ile Arg Gly Leu Ala Glu Pro Ile Arg Leu Leu Leu Val Asp Gln Gly
    930                 935                 940

Ile Lys Phe Thr Asp Glu His Ile Pro Lys Asp Asp Phe Val Ser Ile
945                 950                 955                 960

Lys Ser Gln Phe Gln Phe Gly Gln Leu Pro Cys Phe Tyr Asp Gly Asp
                965                 970                 975
```

-continued

```
Gln Gln Ile Val Gln Ser Gly Ala Ile Leu Arg His Leu Ala Arg Lys
            980                 985                 990

Phe Asn Leu Asn Gly Glu Asn Asn  Ala Glu Thr Ser Tyr  Val Asp Met
        995                 1000                 1005

Phe Tyr  Glu Gly Ile Arg Asp  Leu His Ser Lys Tyr  Thr Arg Met
    1010                 1015                 1020

Ile Tyr  Glu Ala Tyr Glu Thr  Gln Lys Asp Pro Phe  Ile Lys Asn
    1025                 1030                 1035

Ile Leu  Pro Gln Glu Leu Ala  Lys Leu Glu Lys Leu  Leu Ala Thr
    1040                 1045                 1050

Arg Asp  Asn Gly Lys Asn Phe  Ile Leu Gly Asp Lys  Ile Ser Phe
    1055                 1060                 1065

Ala Asp  Tyr Val Leu Phe Glu  Glu Leu Asp Val Gln  Gln Ile Leu
    1070                 1075                 1080

Asp Pro  His Cys Leu Glu Lys  Phe Pro Leu Leu Lys  Ala Phe His
    1085                 1090                 1095

Gln Arg  Leu Gly Asp Lys Pro  Lys Ile Lys Glu Tyr  Cys Ala Lys
    1100                 1105                 1110

Arg Asn  Ala Ser Lys Met Pro  Val Asn Gly Asn Gly  Lys Gln Glu
    1115                 1120                 1125

Gln Lys  Leu Ile Ser Glu Glu  Asp Leu
    1130                 1135
```

<210> SEQ ID NO 19
<211> LENGTH: 1413
<212> TYPE: DNA
<213> ORGANISM: Artificial Sequence
<220> FEATURE:
<223> OTHER INFORMATION: M1 segment of MUEIG chimera

<400> SEQUENCE: 19

```
gagaactggg gcttggtgat tttccaaaag gagatgttcc tcctcgattc tctcctcgaa     60

agcaacgcca acatgaccgt ggatttgctt gcggagcaat acgacattga gaaaatcatc    120

acacacgaat tagtgcacca gtggttcgga aaccttgtta cgatcaatga ttggagcgaa    180

ctctggattt cagagggatt cgcgagttac tacgctaatg atttcctgaa gaagcagcgt    240

cccatcttag cgatcaacga gtatttcctt aggttgtctc aactgttgtc acgtcagaca    300

tccaacgaga agatgccgct cgtaaagcgc tttcgcactg aggcagaagt tgagaaggcc    360

tttaacccat accacctgta tacgaaaggc gcggccatag tcaagatgat gtgcgacctt    420

gtcggcgaaa acaactttcg tgagggagtc cgtcgtttcc ttaaaacaaa cgcctataag    480

tcggtaggta ggtctgctct ttggaaggcg atgccaatct acacaaagca cggtctggaa    540

aatcgaaagc tggaaaacgt gatcgagccc tggttgatta acgacggtat gcctgaggtt    600

atggtatccc gaaactacaa ttacggaact atccatttga tacccagact gtctgaccag    660

aataggtaca tcatctattt gcgcgatgtg agctatgacg tcaagaactc taacgaatcc    720

attaagaaga tgaagcgtaa gaaatggatg gacaaaatcc ccatccgcag caggatgaag    780

ttcagaaaga caggtcgcag caagaagacg gaggtagcta atgacgagga agtctctagt    840

ttcttttact tcgatttcat taacaacatg ctgcctaatt ctcgaaaaga ggttaagctc    900

aaacaaacga taggaggcgg caatccagtg ggtagacgta agaaagaaag aaggcatcgc    960

aagatcaacg agaagtggcg cagctcccaa gaacaacagt tctggtccat tcctttcacc   1020

tatcaattat caagtaaaac aaacttcttt ggtgacacga taagagagct gtggctccac   1080
```

aacaagaccg tcgtgttcat ggacaagaaa gctcaggcct ctgctacact cctggcgaac 1140
gttaactgga aatacccgta ccgagttaac tacgatattg agaactggaa gatgctcgct 1200
cgcctcctgc acgagaacca cttgtcaatc cctttgtata gtcgcatcca gctaatcttc 1260
gactcagaat tttacttgaa gcaaagcaac gtgcctgagg tctacttgta tatcctctcc 1320
tacctcacca aggagaatga cgtcggcctt cttcttttcg gtttggatgc actgtaccgc 1380
ttctttgaca tgttccgcgg ctcatcaatc aat 1413

<210> SEQ ID NO 20
<211> LENGTH: 744
<212> TYPE: DNA
<213> ORGANISM: Artificial Sequence
<220> FEATURE:
<223> OTHER INFORMATION: UDP segment of MUEIG chimera

<400> SEQUENCE: 20
ctactgcatg ctgctctgct aagtatgcta ctcgaatcca tcttctcgta caagatcttg 60
atcttctcgc cacgtctagc acattcgcac atcaatttca tgggaattct cgctgatgta 120
cttgtggagg caggccatga tatcaccatc ttcatgccgg acttaaatcc cgacgtaagt 180
aataacggtt caaagttagc aaagatcgtg cgcaaaacct tctcgaacac caacaaccag 240
atcctgaaaa aaaactccgc ccgtgaaaag tggaagaaga aaggtgattc aatcttacag 300
gtctacagac tgtttcagca actcgcagac tctcagagat taatgtgtct ggaacacttg 360
gaggatgaca agctgatttc gtggcttcag acagagcaat acgatctcgg catcactgag 420
caaatatcgt tttgtggcta tgccatcttt aacaggatcg gcttgaataa ccaggtaacc 480
gccggagcta taaccctgat ggaggtgctg tctgatccat tcggcgtgtc aagcaatcca 540
agctacgtac ccggaggttt ctccagcaaa gccgacaaaa tgaattacct ggagagactc 600
gccaatatta tcatctatac aacctcctac attttaacca agttcgtctg ggagccagct 660
gttcagagtc tgcagcacaa tctacccaac aacttcaact acattgaaac tctgaagaat 720
tcctccctgt actttgtcaa cact 744

<210> SEQ ID NO 21
<211> LENGTH: 234
<212> TYPE: DNA
<213> ORGANISM: Artificial Sequence
<220> FEATURE:
<223> OTHER INFORMATION: Exp2 segment of MUEIG chimera

<400> SEQUENCE: 21
ggtttatctt tcggaaccat tcccgatttc caagtggtgc agtacctacc cacatacaat 60
gaaactgtgc tcctcccgaa cggaactata actgtggtcg agaaaattga agaaatgcga 120
atcgaacacc caattttcgt tctgaccgag cgtatatgca ttgcgttctt tacgatagaa 180
tattgtctgc gcctgttcgc agcgcctaga aaattgcgtt tcatgcttaa accc 234

<210> SEQ ID NO 22
<211> LENGTH: 258
<212> TYPE: DNA
<213> ORGANISM: Artificial Sequence
<220> FEATURE:
<223> OTHER INFORMATION: IF1 segment of MUEIG chimera

<400> SEQUENCE: 22
gtcaaagacg aaaagtctaa gacgctattt gaagtagagg gtgcggtcac agcattgctg 60
cctgcagccg aattccgcgt taagctggac aacgaacacg aaatcatctg ccacgttagt 120

```
ggaaaggtgc gccgcagcaa gattcgcatt atcattggag acagagtgct ggtcgaaatg    180

tcaatctacg acagaaacgc taagaaaggt aggattattc gccgtctgaa aggaacttcc    240

gacaggacta tttccaag                                                  258
```

<210> SEQ ID NO 23
<211> LENGTH: 621
<212> TYPE: DNA
<213> ORGANISM: Artificial Sequence
<220> FEATURE:
<223> OTHER INFORMATION: GST segment of MUEIG chimera

<400> SEQUENCE: 23

```
agctacaagc taacctactt cccgataagg ggtttggctg agccgattag gttgctttta     60

gttgaccaag gcatcaaatt cacggacgaa catataccta aagatgactt cgtcagcatt    120

aagagtcagt tccaatttgg ccaattgcct tgcttctacg atggtgacca acagatcgtg    180

cagtcaggtg caatcctgag acacttggct cgtaagttca acttgaatgg cgagaacaac    240

gccgaaactt cctacgtaga tatgttttat gagggcataa gggacctaca ctccaagtat    300

actcgcatga tctatgaggc ctacgaaacc cagaaagatc cattcatcaa gaatatactc    360

ccacaggagc tcgctaagct agaaaagctg ctcgctaccc gtgacaacgg taagaacttc    420

atactgggtg acaaaatctc gttcgccgat tacgtgctgt ttgaggagtt ggacgtacag    480

caaatcttag accctcattg cctggagaaa ttccctctcc ttaaggcctt tcatcagagg    540

ctgggtgata aacccaagat caaagaatac tgtgctaagc gtaacgcttc aaagatgcct    600

gtcaacggta acggcaagca a                                              621
```

<210> SEQ ID NO 24
<211> LENGTH: 3411
<212> TYPE: DNA
<213> ORGANISM: Artificial Sequence
<220> FEATURE:
<223> OTHER INFORMATION: MUEIG Chimera with 5' Murine IgK chain leader
      and 3' C-myc tag

<400> SEQUENCE: 24

```
atggaaacag acacgttatt gctgtgggtg ctcctccttt gggttccagg atcgactggt     60

gacgagaact ggggcttggt gattttccaa aaggagatgt tcctcctcga ttctctcctc    120

gaaagcaacg ccaacatgac cgtggatttg cttgcggagc aatacgacat tgagaaaatc    180

atcacacacg aattagtgca ccagtggttc ggaaaccttg ttacgatcaa tgattggagc    240

gaactctgga tttcagaggg attcgcgagt tactacgcta atgatttcct gaagaagcag    300

cgtcccatct tagcgatcaa cgagtatttc cttaggttgt ctcaactgtt gtcacgtcag    360

acatccaacg agaagatgcc gctcgtaaag cgctttcgca ctgaggcaga agttgagaag    420

gcctttaacc cataccacct gtatacgaaa ggcgcggcca tagtcaagat gatgtgcgac    480

cttgtcggcg aaaacaactt tcgtgaggga gtccgtcgtt tccttaaaac aaacgcctat    540

aagtcggtag gtaggtctgc tctttggaag gcgatgccaa tctacacaaa gcacggtctg    600

gaaaatcgaa agctggaaaa cgtgatcgag ccctggttga ttaacgacgg tatgcctgag    660

gttatggtat cccgaaacta caattacgga actatccatt tgatacccag actgtctgac    720

cagaataggt acatcatcta tttgcgcgat gtgagctatg acgtcaagaa ctctaacgaa    780

tccattaaga agatgaagcg taagaaatgg atggacaaaa tccccatccg cagcaggatg    840

aagttcagaa agacaggtcg cagcaagaag acggaggtag ctaatgacga ggaagtctct    900
```

```
agtttctttt acttcgattt cattaacaac atgctgccta attctcgaaa agaggttaag    960
ctcaaacaaa cgataggagg cggcaatcca gtgggtagac gtaagaaaga aagaaggcat   1020
cgcaagatca acgagaagtg gcgcagctcc caagaacaac agttctggtc cattcctttc   1080
acctatcaat tatcaagtaa aacaaacttc tttggtgaca cgataagaga gctgtggctc   1140
cacaacaaga ccgtcgtgtt catggacaag aaagctcagg cctctgctac actcctggcg   1200
aacgttaact ggaaataccc gtaccgagtt aactacgata ttgagaactg gaagatgctc   1260
gctcgcctcc tgcacgagaa ccacttgtca atccctttgt atagtcgcat ccagctaatc   1320
ttcgactcag aattttactt gaagcaaagc aacgtgcctg aggtctactt gtatatcctc   1380
tcctacctca ccaaggagaa tgacgtcggc cttcttcttt tcggtttgga tgcactgtac   1440
cgcttctttg acatgttccg cggctcatca atcaatggtt ccagtggact actgcatgct   1500
gctctgctaa gtatgctact cgaatccatc ttctcgtaca agatcttgat cttctcgcca   1560
cgtctagcac attcgcacat caatttcatg ggaattctcg ctgatgtact tgtggaggca   1620
ggccatgata tcaccatctt catgccggac ttaaatcccg acgtaagtaa taacggttca   1680
aagttagcaa agatcgtgcg caaaaccttc tcgaacacca acaaccagat cctgaaaaaa   1740
aactccgccc gtgaaaagtg gaagaagaaa ggtgattcaa tcttacaggt ctacagactg   1800
tttcagcaac tcgcagactc tcagagatta atgtgtctgg aacacttgga ggatgacaag   1860
ctgatttcgt ggcttcagac agagcaatac gatctcggca tcactgagca aatatcgttt   1920
tgtggctatg ccatctttaa caggatcggc ttgaataacc aggtaaccgc cggagctata   1980
accctgatgg aggtgctgtc tgatccattc ggcgtgtcaa gcaatccaag ctacgtaccc   2040
ggaggtttct ccagcaaagc cgacaaaatg aattacctgg agagactcgc caatattatc   2100
atctatacaa cctcctacat tttaaccaag ttcgtctggg agccagctgt tcagagtctg   2160
cagcacaatc tacccaacaa cttcaactac attgaaactc tgaagaattc ctccctgtac   2220
tttgtcaaca ctggttcttc tggaggttta tctttcggaa ccattcccga tttccaagtg   2280
gtgcagtacc tacccacata caatgaaact gtgctcctcc cgaacggaac tataactgtg   2340
gtcgagaaaa ttgaagaaat gcgaatcgaa cacccaattt tcgttctgac cgagcgtata   2400
tgcattgcgt tctttacgat agaatattgt ctgcgcctgt tcgcagcgcc tagaaaattg   2460
cgtttcatgc ttaaacccgg aagcagtggc gtcaaagacg aaaagtctaa gacgctattt   2520
gaagtagagg gtgcggtcac agcattgctg cctgcagccg aattccgcgt taagctggac   2580
aacgaacacg aaatcatctg ccacgttagt ggaaaggtgc gccgcagcaa gattcgcatt   2640
atcattggag acagagtgct ggtcgaaatg tcaatctacg acagaaacgc taagaaaggt   2700
aggattattc gccgtctgaa aggaacttcc gacaggacta tttccaaggg ttcaagcggt   2760
agctacaagc taacctactt cccgataagg ggtttggctg agccgattag gttgctttta   2820
gttgaccaag gcatcaaatt cacggacgaa catataccta aagatgactt cgtcagcatt   2880
aagagtcagt tccaatttgg ccaattgcct tgcttctacg atggtgacca acagatcgtg   2940
cagtcaggtg caatcctgag acacttggct cgtaagttca acttgaatgg cgagaacaac   3000
gccgaaactt cctacgtaga tatgttttat gagggcataa gggacctaca ctccaagtat   3060
actcgcatga tctatgaggc ctacgaaacc cagaaagatc cattcatcaa gaatatactc   3120
ccacaggagc tcgctaagct agaaaagctg ctcgctaccc gtgacaacgg taagaacttc   3180
atactgggtg acaaaatctc gttcgccgat tacgtgctgt ttgaggagtt ggacgtacag   3240
```

-continued caaatcttag accctcattg cctggagaaa ttccctctcc ttaaggcctt tcatcagagg 3300
ctgggtgata aacccaagat caaagaatac tgtgctaagc gtaacgcttc aaagatgcct 3360
gtcaacggta acggcaagca agagcagaaa ttgatctcgg aggaagatct c 3411

<210> SEQ ID NO 25
<211> LENGTH: 369
<212> TYPE: PRT
<213> ORGANISM: Artificial Sequence
<220> FEATURE:
<223> OTHER INFORMATION: Necepsin segment of Necepsin-Prof2-TPP-ShTK (NPTS) chimera

<400> SEQUENCE: 25

```
Ser Lys Ile Gly Ser Val Arg Gln Gln Leu Leu Arg Ala Gly Lys Leu
1               5                   10                  15

Lys Gln Phe Asn Asn Leu Ile Gln Ser Leu Leu Lys Glu Asn Gly Ile
            20                  25                  30

Val Asp Phe Phe Glu Tyr Met Asp Asn Ile Tyr Val Ile Asn Val Thr
        35                  40                  45

Ile Gly Thr Pro Pro Gln His Phe Glu Ile Val Pro Asp Thr Gly Ser
    50                  55                  60

Ser Asp Leu Trp Val Ile Ser Ile Lys Cys Asn Ser Gln Ser Cys Lys
65                  70                  75                  80

Gly Asp Lys Leu His Pro Lys Asn Arg Phe Asp Pro Ser Lys Ser Ser
                85                  90                  95

Thr Tyr Ser Val Asp Gly Arg Lys Phe Thr Ile Thr Tyr Glu Leu Gly
            100                 105                 110

Tyr Ala Glu Gly Ile Leu Gly Ile Asp His Phe Ser Phe Ala Asp Leu
        115                 120                 125

Ala Val Glu Met Gln Thr Phe Gly Leu Ala Glu Gln Ile Ala His Val
    130                 135                 140

Phe Gly Asp Ile Pro Ile Asp Gly Ile Met Gly Leu Ala Trp Pro Ala
145                 150                 155                 160

Leu Ser Glu Phe Gln Val Thr Pro Pro Met Gln Asn Ile Leu Asp Glu
                165                 170                 175

Leu Asp Glu Pro Ile Met Thr Val Tyr Met Thr Arg Glu Ile Glu Pro
            180                 185                 190

Ile Met Glu Glu Val Tyr Gly Gly Glu Ile Thr Phe Gly Gly Phe Asp
        195                 200                 205

Glu Gln Asn Cys Glu Leu Pro Ile Arg Trp Val Glu Leu Thr Ser Gln
    210                 215                 220

Ser Phe Trp Gln Phe Thr Val Thr Gly Val Arg Val Gln Ser Tyr Lys
225                 230                 235                 240

Asn Thr Asn Trp Leu Gln Gly Ile Ser Asp Thr Gly Thr Ser Tyr Leu
                245                 250                 255

Ile Ile Pro Thr Phe Leu Met Lys Pro Ile Ile Lys Lys Ile Asn Ala
            260                 265                 270

Thr Phe Ser Phe Asp Tyr Asp Ala Tyr Val Leu Asp Cys Ser Met Arg
        275                 280                 285

Asn Thr Gly Pro Asn Ile Glu Ile Ala Ile Ser Gly Leu Tyr Tyr Ser
    290                 295                 300

Ile Pro Pro Glu Gln Tyr Ile Leu Gln Tyr Ile Asp Glu Ser Gly Ser
305                 310                 315                 320

Pro Val Cys Ile Phe Ala Ala Phe Glu Asn Phe Gly Val Gly Phe Ser
                325                 330                 335
```

Pro Ala Trp Ile Leu Gly Asp Val Phe Ile Arg Ser Tyr Cys Asn Val
340 345 350

His Asp Tyr Val Asn Asn Arg Ile Gly Phe Ala Lys Ser Tyr Phe Gln
355 360 365

Gln

<210> SEQ ID NO 26
<211> LENGTH: 129
<212> TYPE: PRT
<213> ORGANISM: Artificial Sequence
<220> FEATURE:
<223> OTHER INFORMATION: Prof2 segment of NPTS chimera

<400> SEQUENCE: 26

Ser Gly Trp Ala Ala Tyr Ile Lys Asn Leu Leu Asp Ser Ser Gln Gly
1 5 10 15

Ile Gln Arg Ala Ala Ile Val Gly Tyr Pro Asp Gly Ser Val Trp Ala
20 25 30

Arg Ser Glu Gly Asp Arg Glu Phe Arg Ala Thr Asp Glu Glu Leu Lys
35 40 45

Lys Phe Val Ser Leu Tyr Asp His Ile Glu Lys Val Pro Ala Thr Gly
50 55 60

Cys Asp Leu Glu Gly Val His Tyr Ile Val Pro Arg Thr Glu Gln Asn
65 70 75 80

Leu Ile Phe Gly Lys Arg Asp Lys Thr Gly Ile Phe Ala Ala Lys Thr
85 90 95

Lys Ser Ala Val Leu Ile Ala Cys Tyr Lys Gly Glu Asn Ala Ala Glu
100 105 110

Val Arg Val Ala Val Glu Lys Leu Ala Gln Tyr Leu Met Asp Ser Gly
115 120 125

Tyr

<210> SEQ ID NO 27
<211> LENGTH: 510
<212> TYPE: PRT
<213> ORGANISM: Artificial Sequence
<220> FEATURE:
<223> OTHER INFORMATION: TPP segment of NPTS chimera

<400> SEQUENCE: 27

Thr Glu Thr Ile Ala Asp Gln Glu Lys Gln Lys Asn Thr Lys Leu Glu
1 5 10 15

Lys His Glu Ala Ala Lys Asp Glu Pro Ala Glu Glu Lys Glu Arg Glu
20 25 30

Arg Glu Thr Pro Gly Ser Gly Thr Ala Lys Asn Thr Glu Gln Asn Leu
35 40 45

Ser Leu Ser Leu Glu Gln Thr Gly Ile Ile Lys Asn Asp Asn Val Gln
50 55 60

Thr Ile Asp Asp Phe Lys Asp Leu Met Tyr Lys Met Gln Glu Thr Arg
65 70 75 80

Arg Ala Ile Val Val Ala Leu Leu Asn Glu Lys Asp Leu Lys Asn Asp
85 90 95

Asp Ile Glu Ile Leu Arg Arg Ala Tyr Glu Lys Leu Thr Asp Asn Gln
100 105 110

Thr His Ser Phe Gln Arg Glu Met Cys Thr Leu Thr Thr Lys Leu Ser
115 120 125

```
Val Asn Ile Arg Asp Glu Thr Arg Gly Leu Glu Lys Asp Leu Lys Tyr
    130                 135                 140

Leu Glu Ile Leu Thr His Ile Arg Gly Glu Glu Pro Ser Leu Ser Trp
145                 150                 155                 160

Pro Val Val Met Ser Arg Leu Asp Leu Ile Ser Ile Leu Ser Asn Tyr
                165                 170                 175

His Pro Glu Gly Lys Glu Lys Phe Met Lys Glu Tyr Glu Asn Thr Val
            180                 185                 190

Arg Phe Leu His Thr Phe Ile Gly Ser Glu Ala Ile Thr Gly Lys Lys
        195                 200                 205

Pro Ile Phe Ile Thr Asp Trp Asp Gly Thr Met Lys Asp Tyr Cys Ser
    210                 215                 220

Gln Tyr Ala Thr Asn Leu Gln Pro Val Tyr Ser Ala Val Gly Met Ile
225                 230                 235                 240

Arg Phe Ala Asp Arg Phe Thr Arg Ile Ser Ala Val Leu Thr Ala Gly
                245                 250                 255

Pro Leu Arg Gly Pro Gly Ile Leu Asp Leu Thr Ala Met Pro Ile Asp
            260                 265                 270

Gly Pro Val Met Phe Ser Gly Ser Trp Gly Arg Glu Trp Trp Leu Ser
        275                 280                 285

Gly Lys Arg Val Val His Glu Asp Gly Ile Thr Asp Ala Gly Phe Asn
    290                 295                 300

Ala Leu Gln Arg Leu Asp Asp Glu Met Lys Asp Leu Leu His Ser Ser
305                 310                 315                 320

Asp Tyr Ala Pro Phe Ala Leu Val Gly Ser Gly Val Gln Arg Lys Val
                325                 330                 335

Asp Arg Leu Thr Leu Gly Val Gln Thr Val Cys His His Val Thr Ser
            340                 345                 350

Glu Leu Ser Asn Lys Tyr Gln Thr Ala Val Lys Glu Arg Met His Arg
        355                 360                 365

Val Asp Pro Asn Ser Gln Ile Leu Val Phe Asp Pro Ser Thr Glu Leu
    370                 375                 380

Glu Val Glu Val Val Val His Ser Ser Gly Thr Ile Trp Asn Lys Ala
385                 390                 395                 400

Asp Gly Val Asp Arg Leu Ile Lys Ser Leu Gly Asp Ser Leu Ser Thr
                405                 410                 415

Gln Gly Lys Ile Leu Ile Cys Gly Asp Thr Leu Ser Asp Ile Pro Met
            420                 425                 430

Val Arg Gln Ala Ala Lys Gln Asn Pro Glu Gly Val Met Ala Ile Phe
        435                 440                 445

Val Gly Thr Lys Val Ser Leu Arg Glu Glu Val Lys Gln Val Val Gly
    450                 455                 460

Asp Glu Ser Arg Cys Cys Phe Val Ser Cys Pro Asp Val Ile His Ala
465                 470                 475                 480

Ala Ile Ser Gln Ile Leu Asn Glu Gln Cys Ile Val Glu Arg Ser Thr
                485                 490                 495

Ser Gly Asn Ser Glu Lys Asn Asn Lys Met Thr Ser Glu Thr
            500                 505                 510
```

<210> SEQ ID NO 28
<211> LENGTH: 167
<212> TYPE: PRT
<213> ORGANISM: Artificial Sequence
<220> FEATURE:
<223> OTHER INFORMATION: ShTK segment of NPTS chimera

<400> SEQUENCE: 28

Lys Asp Glu Glu Cys Lys Asp Leu Tyr Tyr Gln Cys Asn Gly Met Asn
1 5 10 15

Cys Asn Asp Pro Ile Thr Glu Val Leu Cys Ala Lys Thr Cys Gly Ile
20 25 30

Cys Gly Thr Thr Pro Ser Ala Thr Thr Asp Pro Asp Cys Asn Asp Met
35 40 45

Phe Gly Gln Cys Ser Ile Lys Ile Cys Met Asp Pro Met Ala Glu Lys
50 55 60

Leu Cys Ala Lys Thr Cys Gly Phe Cys Ala Thr Thr Pro Ser Ser Thr
65 70 75 80

Ile Ala Pro Val Cys Lys Asp Leu Leu Asp Gln Cys Asp Asn Met Asn
85 90 95

Cys Ser Asn Leu Phe Ala Lys Glu Leu Cys Ala Lys Thr Cys Lys Phe
100 105 110

Cys Asp Asp Asp Leu Thr Pro Ser Pro Glu Glu Cys Asn Cys Leu Cys
115 120 125

Lys Ile Leu Gln Pro Leu Cys Lys Phe Val Glu Trp Ile Asp Gly Ser
130 135 140

Phe Pro Asp Gly Phe Cys Ser Arg Cys Gln Lys Cys Lys Glu Gln Lys
145 150 155 160

Leu Ile Ser Glu Glu Asp Leu
165

<210> SEQ ID NO 29
<211> LENGTH: 1208
<212> TYPE: PRT
<213> ORGANISM: Artificial Sequence
<220> FEATURE:
<223> OTHER INFORMATION: NPTS Chimera with 5' Murine IgK chain leader and 3' C-myc tag

<400> SEQUENCE: 29

Met Glu Thr Asp Thr Leu Leu Leu Trp Val Leu Leu Leu Trp Val Pro
1 5 10 15

Gly Ser Thr Gly Asp Ser Lys Ile Gly Ser Val Arg Gln Gln Leu Leu
20 25 30

Arg Ala Gly Lys Leu Lys Gln Phe Asn Asn Leu Ile Gln Ser Leu Leu
35 40 45

Lys Glu Asn Gly Ile Val Asp Phe Phe Glu Tyr Met Asp Asn Ile Tyr
50 55 60

Val Ile Asn Val Thr Ile Gly Thr Pro Pro Gln His Phe Glu Ile Val
65 70 75 80

Pro Asp Thr Gly Ser Ser Asp Leu Trp Val Ile Ser Ile Lys Cys Asn
85 90 95

Ser Gln Ser Cys Lys Gly Asp Lys Leu His Pro Lys Asn Arg Phe Asp
100 105 110

Pro Ser Lys Ser Ser Thr Tyr Ser Val Asp Gly Arg Lys Phe Thr Ile
115 120 125

Thr Tyr Glu Leu Gly Tyr Ala Glu Gly Ile Leu Gly Ile Asp His Phe
130 135 140

Ser Phe Ala Asp Leu Ala Val Glu Met Gln Thr Phe Gly Leu Ala Glu
145 150 155 160

Gln Ile Ala His Val Phe Gly Asp Ile Pro Ile Asp Gly Ile Met Gly
165 170 175

-continued

```
Leu Ala Trp Pro Ala Leu Ser Glu Phe Gln Val Thr Pro Pro Met Gln
            180                 185                 190

Asn Ile Leu Asp Glu Leu Asp Glu Pro Ile Met Thr Val Tyr Met Thr
        195                 200                 205

Arg Glu Ile Glu Pro Ile Met Glu Glu Val Tyr Gly Gly Glu Ile Thr
    210                 215                 220

Phe Gly Gly Phe Asp Glu Gln Asn Cys Glu Leu Pro Ile Arg Trp Val
225                 230                 235                 240

Glu Leu Thr Ser Gln Ser Phe Trp Gln Phe Thr Val Thr Gly Val Arg
                245                 250                 255

Val Gln Ser Tyr Lys Asn Thr Asn Trp Leu Gln Gly Ile Ser Asp Thr
            260                 265                 270

Gly Thr Ser Tyr Leu Ile Ile Pro Thr Phe Leu Met Lys Pro Ile Ile
        275                 280                 285

Lys Lys Ile Asn Ala Thr Phe Ser Phe Asp Tyr Asp Ala Tyr Val Leu
    290                 295                 300

Asp Cys Ser Met Arg Asn Thr Gly Pro Asn Ile Glu Ile Ala Ile Ser
305                 310                 315                 320

Gly Leu Tyr Tyr Ser Ile Pro Pro Glu Gln Tyr Ile Leu Gln Tyr Ile
                325                 330                 335

Asp Glu Ser Gly Ser Pro Val Cys Ile Phe Ala Ala Phe Glu Asn Phe
            340                 345                 350

Gly Val Gly Phe Ser Pro Ala Trp Ile Leu Gly Asp Val Phe Ile Arg
        355                 360                 365

Ser Tyr Cys Asn Val His Asp Tyr Val Asn Asn Arg Ile Gly Phe Ala
    370                 375                 380

Lys Ser Tyr Phe Gln Gln Gly Ser Ser Gly Ser Gly Trp Ala Ala Tyr
385                 390                 395                 400

Ile Lys Asn Leu Leu Asp Ser Ser Gln Gly Ile Gln Arg Ala Ala Ile
                405                 410                 415

Val Gly Tyr Pro Asp Gly Ser Val Trp Ala Arg Ser Glu Gly Asp Arg
            420                 425                 430

Glu Phe Arg Ala Thr Asp Glu Glu Leu Lys Lys Phe Val Ser Leu Tyr
        435                 440                 445

Asp His Ile Glu Lys Val Pro Ala Thr Gly Cys Asp Leu Glu Gly Val
    450                 455                 460

His Tyr Ile Val Pro Arg Thr Glu Gln Asn Leu Ile Phe Gly Lys Arg
465                 470                 475                 480

Asp Lys Thr Gly Ile Phe Ala Ala Lys Thr Lys Ser Ala Val Leu Ile
                485                 490                 495

Ala Cys Tyr Lys Gly Glu Asn Ala Ala Glu Val Arg Val Ala Val Glu
            500                 505                 510

Lys Leu Ala Gln Tyr Leu Met Asp Ser Gly Tyr Gly Ser Ser Gly Thr
        515                 520                 525

Glu Thr Ile Ala Asp Gln Glu Lys Gln Lys Asn Thr Lys Leu Glu Lys
    530                 535                 540

His Glu Ala Ala Lys Asp Glu Pro Ala Glu Glu Lys Glu Arg Glu Arg
545                 550                 555                 560

Glu Thr Pro Gly Ser Gly Thr Ala Lys Asn Thr Glu Gln Asn Leu Ser
                565                 570                 575

Leu Ser Leu Glu Gln Thr Gly Ile Ile Lys Asn Asp Asn Val Gln Thr
            580                 585                 590
```

-continued

```
Ile Asp Asp Phe Lys Asp Leu Met Tyr Lys Met Gln Glu Thr Arg Arg
        595                 600                 605

Ala Ile Val Val Ala Leu Leu Asn Glu Lys Asp Leu Lys Asn Asp Asp
    610                 615                 620

Ile Glu Ile Leu Arg Arg Ala Tyr Glu Lys Leu Thr Asp Asn Gln Thr
625                 630                 635                 640

His Ser Phe Gln Arg Glu Met Cys Thr Leu Thr Thr Lys Leu Ser Val
                645                 650                 655

Asn Ile Arg Asp Glu Thr Arg Gly Leu Glu Lys Asp Leu Lys Tyr Leu
            660                 665                 670

Glu Ile Leu Thr His Ile Arg Gly Glu Glu Pro Ser Leu Ser Trp Pro
        675                 680                 685

Val Val Met Ser Arg Leu Asp Leu Ile Ser Ile Leu Ser Asn Tyr His
    690                 695                 700

Pro Glu Gly Lys Glu Lys Phe Met Lys Glu Tyr Glu Asn Thr Val Arg
705                 710                 715                 720

Phe Leu His Thr Phe Ile Gly Ser Glu Ala Ile Thr Gly Lys Lys Pro
                725                 730                 735

Ile Phe Ile Thr Asp Trp Asp Gly Thr Met Lys Asp Tyr Cys Ser Gln
            740                 745                 750

Tyr Ala Thr Asn Leu Gln Pro Val Tyr Ser Ala Val Gly Met Ile Arg
        755                 760                 765

Phe Ala Asp Arg Phe Thr Arg Ile Ser Ala Val Leu Thr Ala Gly Pro
    770                 775                 780

Leu Arg Gly Pro Gly Ile Leu Asp Leu Thr Ala Met Pro Ile Asp Gly
785                 790                 795                 800

Pro Val Met Phe Ser Gly Ser Trp Gly Arg Glu Trp Trp Leu Ser Gly
                805                 810                 815

Lys Arg Val Val His Glu Asp Gly Ile Thr Asp Ala Gly Phe Asn Ala
            820                 825                 830

Leu Gln Arg Leu Asp Asp Glu Met Lys Asp Leu Leu His Ser Ser Asp
        835                 840                 845

Tyr Ala Pro Phe Ala Leu Val Gly Ser Gly Val Gln Arg Lys Val Asp
    850                 855                 860

Arg Leu Thr Leu Gly Val Gln Thr Val Cys His His Val Thr Ser Glu
865                 870                 875                 880

Leu Ser Asn Lys Tyr Gln Thr Ala Val Lys Glu Arg Met His Arg Val
                885                 890                 895

Asp Pro Asn Ser Gln Ile Leu Val Phe Asp Pro Ser Thr Glu Leu Glu
            900                 905                 910

Val Glu Val Val Val His Ser Ser Gly Thr Ile Trp Asn Lys Ala Asp
        915                 920                 925

Gly Val Asp Arg Leu Ile Lys Ser Leu Gly Asp Ser Leu Ser Thr Gln
    930                 935                 940

Gly Lys Ile Leu Ile Cys Gly Asp Thr Leu Ser Asp Ile Pro Met Val
945                 950                 955                 960

Arg Gln Ala Ala Lys Gln Asn Pro Glu Gly Val Met Ala Ile Phe Val
                965                 970                 975

Gly Thr Lys Val Ser Leu Arg Glu Glu Val Lys Gln Val Val Gly Asp
            980                 985                 990

Glu Ser Arg Cys Cys Phe Val Ser  Cys Pro Asp Val Ile  His Ala Ala
        995                 1000                1005

Ile Ser  Gln Ile Leu Asn Glu  Gln Cys Ile Val Glu  Arg Ser Thr
```

```
    1010                1015                1020

Ser Gly  Asn Ser Glu Lys Asn  Asn Lys Met Thr Ser  Glu Thr Gly
    1025                1030                1035

Ser Ser  Gly Lys Asp Glu Glu  Cys Lys Asp Leu Tyr  Tyr Gln Cys
    1040                1045                1050

Asn Gly  Met Asn Cys Asn Asp  Pro Ile Thr Glu Val  Leu Cys Ala
    1055                1060                1065

Lys Thr  Cys Gly Ile Cys Gly  Thr Thr Pro Ser Ala  Thr Thr Asp
    1070                1075                1080

Pro Asp  Cys Asn Asp Met Phe  Gly Gln Cys Ser Ile  Lys Ile Cys
    1085                1090                1095

Met Asp  Pro Met Ala Glu Lys  Leu Cys Ala Lys Thr  Cys Gly Phe
    1100                1105                1110

Cys Ala  Thr Thr Pro Ser Ser  Thr Ile Ala Pro Val  Cys Lys Asp
    1115                1120                1125

Leu Leu  Asp Gln Cys Asp Asn  Met Asn Cys Ser Asn  Leu Phe Ala
    1130                1135                1140

Lys Glu  Leu Cys Ala Lys Thr  Cys Lys Phe Cys Asp  Asp Asp Leu
    1145                1150                1155

Thr Pro  Ser Pro Glu Glu Cys  Asn Cys Leu Cys Lys  Ile Leu Gln
    1160                1165                1170

Pro Leu  Cys Lys Phe Val Glu  Trp Ile Asp Gly Ser  Phe Pro Asp
    1175                1180                1185

Gly Phe  Cys Ser Arg Cys Gln  Lys Cys Lys Glu Gln  Lys Leu Ile
    1190                1195                1200

Ser Glu  Glu Asp Leu
    1205
```

<210> SEQ ID NO 30
<211> LENGTH: 1107
<212> TYPE: DNA
<213> ORGANISM: Artificial Sequence
<220> FEATURE:
<223> OTHER INFORMATION: Necepsin segment of NPTS chimera

<400> SEQUENCE: 30

```
tccaaaatag gctcggtccg ccaacaactg ctgcgtgccg gtaaactcaa gcaattcaat     60
aacctcatac agtcgcttct taaagagaat ggtatcgtgg acttcttcga atacatggac    120
aacatctatg tgataaatgt gaccattggt acaccaccgc agcactttga gattgttccc    180
gacaccggct cctctgatct atgggtgatt tctatcaagt gcaactcgca aagctgtaag    240
ggcgacaagc tccaccccaa gaacaggttc gacccatcca aaagttccac atactcagtc    300
gacggtcgaa aattcacaat tacgtacgaa ctgggatacg ccgaaggcat cctgggtatc    360
gaccacttca gtttcgctga tctggcggtt gagatgcaga cttttggttt agccgaacaa    420
atcgcccacg tattcggcga tatcccgata gacggcatca tgggtctagc gtggccagcc    480
ctttccgagt ttcaggtgac tccgccaatg caaaacatac tggatgaact agatgaacct    540
atcatgaccg tttacatgac acgcgagata gagcccatca tggaggaggt ctatggaggt    600
gaaatcacct tcggtggctt cgacgagcag aactgcgaac tgcctatccg ctgggtggaa    660
ctcacttcac agtccttctg gcagttcacg gtgaccggcg tacgtgttca gtcatataag    720
aacactaatt ggctgcaagg aattagcgac acaggaactt cttacttgat catccccaca    780
ttcttgatga agcccattat aaagaaaatt aacgcaactt tcagctttga ctacgacgct    840
```

-continued

```
tatgtcctcg attgcagtat gcgcaacacg ggtccgaaca ttgagatcgc aatttcgggc    900

ttgtattaca gcattccacc tgagcagtac attctgcagt atatcgatga gtctggctca    960

ccagtgtgca tctttgcagc attcgagaac ttcggcgtcg gcttctcacc cgcatggata   1020

cttggtgatg tgttcatccg ctcgtactgc aatgtgcatg attacgtgaa caaccgcata   1080

ggtttcgcaa agtcctactt ccaacaa                                      1107
```

<210> SEQ ID NO 31
<211> LENGTH: 387
<212> TYPE: DNA
<213> ORGANISM: Artificial Sequence
<220> FEATURE:
<223> OTHER INFORMATION: Prof2 segment of NPTS chimera

<400> SEQUENCE: 31

```
tcgggttggg cggcctatat caagaacctt ctggattcca gccaaggaat acaacgtgca     60

gccatcgtag gatatcctga cggtagtgta tgggccagat ctgaaggcga ccgcgagttc    120

agagctaccg atgaggaact gaagaagttc gtgtctctgt acgatcacat cgagaaggtg    180

cctgcgacag gctgtgacct cgaaggagtt cactatatcg ttcctaggac tgaacaaaac    240

ttgatcttcg gaaagagaga caagacaggt attttcgctg ccaagacgaa gtcagccgtt    300

ttgatagcct gctacaaagg agagaatgct gcagaggtca gggtagctgt ggaaaagcta    360

gctcagtacc ttatggactc cggttac                                        387
```

<210> SEQ ID NO 32
<211> LENGTH: 1530
<212> TYPE: DNA
<213> ORGANISM: Artificial Sequence
<220> FEATURE:
<223> OTHER INFORMATION: TPP segment of NPTS chimera

<400> SEQUENCE: 32

```
accgaaacca ttgccgatca agaaaagcag aagaacacca aattggagaa gcatgaggcg     60

gctaaggacg aaccagcaga agagaaagag cgtgaaagag agactcccgg aagcggtacc    120

gcgaagaaca ccgaacagaa tctgagcctt tccctggagc aaacaggtat tatcaaaaac    180

gataacgtcc agaccattga tgactttaag gacttgatgt acaagatgca agagacaaga    240

agagccattg tagtagcgct gttgaatgaa aaggacttaa agaatgacga catcgagatt    300

ctgcgccgtg cctatgagaa gcttactgat aatcagaccc actcgtttca gcgcgagatg    360

tgtacgttaa caactaagtt gtctgtcaac attcgagatg agacaagggg cctcgaaaag    420

gacttgaaat atctggagat cctcacccat attcgtggtg aggaaccatc actctcctgg    480

ccagtggtta tgtctcgctt ggacctaatc tctattctgt ctaactacca tccggaggga    540

aaggagaaat tcatgaagga atacgaaaac acggtccgct tcttgcacac cttcatcggc    600

tcagaggcta tcaccggtaa gaagccgatc ttcatcactg attgggacgg caccatgaaa    660

gactactgct cacagtacgc gactaacttg cagcctgtct actccgctgt tggtatgatt    720

cgcttcgctg accgatttac tcgcatcagt gctgtgttga ccgcaggacc tctcagggga    780

cccggaatct tagacctgac ggcgatgcct atagacggtc cagtcatgtt ctcaggtagc    840

tggggaaggg agtggtggct ctctggcaaa agagtagtgc atgaggacgg tatcactgac    900

gcgggattca acgctttgca acgtttagac gatgagatga aagacttgct tcatagcagt    960

gattacgcac catttgctct ggtgggttcc ggagttcagc gcaaggttga caggctgacc   1020

ttaggagtac agactgtatg ccaccacgtt acttcagaac taagcaacaa ataccaaact   1080
```

gcggtcaagg aacgtatgca ccgtgtagac cccaatagtc agatccttgt gtttgaccca 1140
tctacggagt tggaagtcga ggtggtggtc catagctcgg gtactatctg gaataaggct 1200
gacggtgtcg atcgattgat caagtctctt ggagattcgt tatcaaccca aggcaaaata 1260
ctcatttgcg gagacacact gagcgacata cctatggtca ggcaagctgc caagcagaac 1320
cctgaaggtg ttatggccat cttcgtcgga acgaaggttt cgctgcgtga agaagtgaaa 1380
caagtcgtcg gtgacgagag cagatgctgc ttcgttagct gcccggatgt gattcacgcc 1440
gccatcagcc agatcctgaa tgaacagtgt atcgtcgaga ggtctacaag tggtaactcc 1500
gagaagaaca acaaaatgac ctccgagaca 1530

<210> SEQ ID NO 33
<211> LENGTH: 471
<212> TYPE: DNA
<213> ORGANISM: Artificial Sequence
<220> FEATURE:
<223> OTHER INFORMATION: ShTK segment of NPTS chimera

<400> SEQUENCE: 33
aaggatgaag agtgcaaaga tctgtactac cagtgtaacg gaatgaattg caacgatcca 60
atcaccgaag tactctgtgc taagacgtgc ggtatctgcg gaactacacc ttccgctaca 120
acagatccgg actgcaatga tatgtttggt cagtgttcta ttaagatctg catggacccc 180
atggcagaga agctgtgtgc taaaacctgt ggcttttgcg ctactacccc atcatccacg 240
attgcccctg tgtgtaaaga cctcctcgat cagtgcgata atatgaactg ctccaacctc 300
ttcgctaagg aactatgtgc taaaacgtgt aaattctgcg atgacgacct gacgcccagt 360
cccgaagagt gcaactgtct atgtaaaatc cttcaacccc tctgcaagtt tgtggaatgg 420
atcgacggta gtttccctga cggtttctgt tcacgttgtc agaaatgcaa g 471

<210> SEQ ID NO 34
<211> LENGTH: 3624
<212> TYPE: DNA
<213> ORGANISM: Artificial Sequence
<220> FEATURE:
<223> OTHER INFORMATION: NPTS Chimera with 5' Murine IgK chain leader and 3' C-myc tag

<400> SEQUENCE: 34
atggaaacgg ataccctgct cctctgggta ttattactct gggtccccgg aagtactggc 60
gactccaaaa taggctcggt ccgccaacaa ctgctgcgtg ccggtaaact caagcaattc 120
aataacctca tacagtcgct tcttaaagag aatggtatcg tggacttctt cgaatacatg 180
gacaacatct atgtgataaa tgtgaccatt ggtacaccac cgcagcactt tgagattgtt 240
cccgacaccg gctcctctga tctatgggtg atttctatca agtgcaactc gcaaagctgt 300
aagggcgaca agctccaccc caagaacagg ttcgacccat ccaaaagttc cacatactca 360
gtcgacggtc gaaaattcac aattacgtac gaactgggat acgccgaagg catcctgggt 420
atcgaccact tcagtttcgc tgatctggcg gttgagatgc agacttttgg tttagccgaa 480
caaatcgccc acgtattcgg cgatatcccg atagacggca tcatgggtct agcgtggcca 540
gccctttccg agtttcaggt gactccgcca atgcaaaaca tactggatga actagatgaa 600
cctatcatga ccgtttacat gacacgcgag atagagccca tcatggagga ggtctatgga 660
ggtgaaatca ccttcggtgg cttcgacgag cagaactgcg aactgcctat ccgctgggtg 720
gaactcactt cacagtcctt ctggcagttc acggtgaccg gcgtacgtgt tcagtcatat 780

-continued

```
aagaacacta attggctgca aggaattagc gacacaggaa cttcttactt gatcatcccc    840
acattcttga tgaagcccat tataaagaaa attaacgcaa ctttcagctt tgactacgac    900
gcttatgtcc tcgattgcag tatgcgcaac acgggtccga acattgagat cgcaatttcg    960
ggcttgtatt acagcattcc acctgagcag tacattctgc agtatatcga tgagtctggc   1020
tcaccagtgt gcatctttgc agcattcgag aacttcggcg tcggcttctc acccgcatgg   1080
atacttggtg atgtgttcat ccgctcgtac tgcaatgtgc atgattacgt gaacaaccgc   1140
ataggtttcg caaagtccta cttccaacaa ggctcctcag gttcgggttg ggcggcctat   1200
atcaagaacc ttctggattc cagccaagga atacaacgtg cagccatcgt aggatatcct   1260
gacggtagtg tatgggccag atctgaaggc gaccgcgagt tcagagctac cgatgaggaa   1320
ctgaagaagt tcgtgtctct gtacgatcac atcgagaagg tgcctgcgac aggctgtgac   1380
ctcgaaggag ttcactatat cgttcctagg actgaacaaa acttgatctt cggaaagaga   1440
gacaagacag gtattttcgc tgccaagacg aagtcagccg ttttgatagc ctgctacaaa   1500
ggagagaatg ctgcagaggt cagggtagct gtggaaaagc tagctcagta ccttatggac   1560
tccggttacg gctcgtcagg caccgaaacc attgccgatc aagaaaagca gaagaacacc   1620
aaattggaga agcatgaggc ggctaaggac gaaccagcag aagagaaaga gcgtgaaaga   1680
gagactcccg gaagcggtac cgcgaagaac accgaacaga atctgagcct ttccctggag   1740
caaacaggta ttatcaaaaa cgataacgtc cagaccattg atgactttaa ggacttgatg   1800
tacaagatgc aagagacaag aagagccatt gtagtagcgc tgttgaatga aaaggactta   1860
aagaatgacg acatcgagat tctgcgccgt gcctatgaga agcttactga taatcagacc   1920
cactcgtttc agcgcgagat gtgtacgtta acaactaagt tgtctgtcaa cattcgagat   1980
gagacaaggg gcctcgaaaa ggacttgaaa tatctggaga tcctcaccca tattcgtggt   2040
gaggaaccat cactctcctg gccagtggtt atgtctcgct tggacctaat ctctattctg   2100
tctaactacc atccggaggg aaaggagaaa ttcatgaagg aatacgaaaa cacggtccgc   2160
ttcttgcaca ccttcatcgg ctcagaggct atcaccggta agaagccgat cttcatcact   2220
gattgggacg gcaccatgaa agactactgc tcacagtacg cgactaactt gcagcctgtc   2280
tactccgctg ttggtatgat tcgcttcgct gaccgattta ctcgcatcag tgctgtgttg   2340
accgcaggac ctctcagggg acccggaatc ttagacctga cggcgatgcc tatagacggt   2400
ccagtcatgt tctcaggtag ctggggaagg gagtggtggc tctctggcaa aagagtagtg   2460
catgaggacg gtatcactga cgcgggattc aacgctttgc aacgtttaga cgatgagatg   2520
aaagacttgc ttcatagcag tgattacgca ccatttgctc tggtgggttc cggagttcag   2580
cgcaaggttg acaggctgac cttaggagta cagactgtat gccaccacgt tacttcagaa   2640
ctaagcaaca aataccaaac tgcggtcaag gaacgtatgc accgtgtaga ccccaatagt   2700
cagatccttg tgtttgaccc atctacggag ttggaagtcg aggtggtggt ccatagctcg   2760
ggtactatct ggaataaggc tgacggtgtc gatcgattga tcaagtctct tggagattcg   2820
ttatcaaccc aaggcaaaat actcatttgc ggagacacac tgagcgacat acctatggtc   2880
aggcaagctg ccaagcagaa ccctgaaggt gttatggcca tcttcgtcgg aacgaaggtt   2940
tcgctgcgtg aagaagtgaa acaagtcgtc ggtgacgaga gcagatgctg cttcgttagc   3000
tgcccggatg tgattcacgc cgccatcagc cagatcctga atgaacagtg tatcgtcgag   3060
aggtctacaa gtggtaactc cgagaagaac aacaaaatga cctccgagac aggcagtagc   3120
```

```
ggcaaggatg aagagtgcaa agatctgtac taccagtgta acggaatgaa ttgcaacgat   3180

ccaatcaccg aagtactctg tgctaagacg tgcggtatct gcggaactac accttccgct   3240

acaacagatc cggactgcaa tgatatgttt ggtcagtgtt ctattaagat ctgcatggac   3300

cccatggcag agaagctgtg tgctaaaacc tgtggctttt gcgctactac cccatcatcc   3360

acgattgccc ctgtgtgtaa agacctcctc gatcagtgcg ataatatgaa ctgctccaac   3420

ctcttcgcta aggaactatg tgctaaaacg tgtaaattct gcgatgacga cctgacgccc   3480

agtcccgaag agtgcaactg tctatgtaaa atccttcaac ccctctgcaa gtttgtggaa   3540

tggatcgacg gtagtttccc tgacggtttc tgttcacgtt gtcagaaatg caaggaacag   3600

aagttgatct ctgaagagga cctg                                          3624
```

<210> SEQ ID NO 35
<211> LENGTH: 644
<212> TYPE: PRT
<213> ORGANISM: Artificial Sequence
<220> FEATURE:
<223> OTHER INFORMATION: Reprolysine segment of Reprolysin-Mrp5-Nas4 (RMN) chimera

<400> SEQUENCE: 35

```
His His Asp Ile Tyr Cys Pro Leu His Ile Tyr Phe Gly Glu His Glu
1               5                   10                  15

Leu Asp Ala Asn Gln Leu Ile Ser Ile Ser Gln Thr Ile Gln Pro Lys
            20                  25                  30

Phe Glu Leu Thr Leu Gln Asn Asp Phe Gly Glu Ser Arg Asp Phe Ile
        35                  40                  45

Phe Gln Ser Asn Arg Glu Leu Ser Lys Thr Ser Ser Lys Ile Asp Met
    50                  55                  60

Leu Cys His Phe Glu Gly Ile Ser Asn Thr Gly Glu His Ser Ala Met
65                  70                  75                  80

Ser Thr Cys Ser Met Ser Leu Leu Gly Gly Leu Phe Thr Ile Asn Gly
                85                  90                  95

Arg Arg Phe Val Leu Glu Val Gly Leu Asn Ala Leu Phe His Phe Val
            100                 105                 110

Pro Leu Ser Asp His Ser Cys Asp Trp Gly Leu Arg Ser Lys Arg Ser
        115                 120                 125

Ile Ala Gly Ser His Val Ala Glu Tyr Tyr Ala Gln Phe Leu Asp Gly
    130                 135                 140

Arg Trp Arg Tyr Val Glu Leu Ala Leu Ile Ala Asp Lys Leu Val Phe
145                 150                 155                 160

Glu Lys Tyr His Lys Asn Val Thr Glu Val Met Gln Arg Leu Asn Ala
                165                 170                 175

Ile Thr Asn Tyr Ile Asn Ser Leu Tyr Leu Pro Ile Asn Ile Arg Val
            180                 185                 190

Val Leu Val Trp Ala Asp Val Trp Thr Asn Asp Asn Pro Val Asp Ile
        195                 200                 205

Thr Ser Asn Ser Asp Thr Thr Leu Trp Asn Phe Leu Asn Trp Arg Lys
    210                 215                 220

Gly Leu Leu Lys Asp His Pro His Asp Asn Ala His Leu Leu Thr Gly
225                 230                 235                 240

Val Ile Phe Glu Asn Asn Val Val Gly Lys Ala Phe Lys Gly Thr Met
                245                 250                 255

Cys Ser Tyr Asp Phe Ser Gly Gly Val Asp Ile Glu His Ser Asp Gln
            260                 265                 270
```

```
Ala Ala Tyr Val Ala Ala Thr Ile Ala His Glu Met Gly His Asn Phe
        275                 280                 285

Gly Met Glu His Asp Ile Asp Glu Ile Glu Cys Arg Cys Pro Ala Lys
    290                 295                 300

Ser Cys Ile Met Ser Pro Ala Thr Gly Ile Thr His Pro Thr Phe Trp
305                 310                 315                 320

Ser Glu Cys Ser Met Arg Ala Leu Gln His Ser Phe Ser Arg Gly Val
                325                 330                 335

Asp Tyr Cys Leu Arg Asn Ser Pro Thr Ser Val Phe Gly Gly Ala Arg
            340                 345                 350

Cys Gly Asn Gly Ile Val Glu Ala Gly Glu Glu Cys Asp Cys Gly Thr
        355                 360                 365

Pro Ser Ser Cys Ile Asn Lys Cys Cys Asn Pro Ala Thr Cys Arg Leu
    370                 375                 380

Ser Glu Thr Ala Val Cys Ala Thr Gly Glu Cys Cys Asp Leu Asn Thr
385                 390                 395                 400

Cys Gln Leu Leu Ser Ala Thr Thr Val Cys Arg Gln Ala Thr Asn Glu
                405                 410                 415

Cys Asp Leu Pro Glu Tyr Cys Asp Gly Leu Met Glu His Cys Pro Ala
            420                 425                 430

Asp Phe Phe Val Gln Asp Gly His Glu Cys Pro Asn His Val Asp Asp
        435                 440                 445

Tyr Cys Tyr Asn Gly Tyr Cys Gly Ser Arg Asp Ala Gln Cys Gln His
    450                 455                 460

Ile Trp Gly Ser Thr Gly Arg Asn Ala Ala Pro Ala Cys Tyr Asp Leu
465                 470                 475                 480

Asn Leu Ser Gly Ser Ser Gly Gly Asn Cys Gly Phe Leu His Glu Thr
                485                 490                 495

Asn Arg Phe Val Pro Cys Asn Lys Asn Asp Ile Lys Cys Gly Arg Leu
            500                 505                 510

His Cys Ile His Glu Asn Glu Lys Leu Val Phe Gly Asp Pro Ser Thr
        515                 520                 525

Val Tyr Thr Ala Tyr Thr Gly Leu Arg Leu Arg Asn Gly Glu Asp Val
    530                 535                 540

Ala Cys Arg Val Ile Trp Thr Lys Tyr Ile Ser Gly Gln Lys Glu Pro
545                 550                 555                 560

Asp Pro Gly Met Val Pro Asn Gly Ala Val Cys Gly Gln Asp Glu Met
                565                 570                 575

Cys Val Asp Ala Lys Cys Gln Asn Arg Thr Ala Lys Val Leu Met Ala
            580                 585                 590

Pro Lys Cys Glu Pro Val Ser Cys Asn Asn Ala Gly Ile Cys Asn Asn
        595                 600                 605

Met Gly Asn Cys His Cys Asp Pro Gly Tyr Gly Gly Ser Ser Cys Ala
    610                 615                 620

Ile Pro Gly Pro Gly Gly Ser Val Asn Ser Gly Pro Ala Ile Glu Gly
625                 630                 635                 640

Gly Val Ile His
```

<210> SEQ ID NO 36
<211> LENGTH: 397
<212> TYPE: PRT
<213> ORGANISM: Artificial Sequence
<220> FEATURE:
<223> OTHER INFORMATION: Mrp5 segment of Reprolysin-Mrp5-Nas4 (RMN)

chimera

<400> SEQUENCE: 36

```
Thr Gly Ser Ile Ala Pro Ala Asp Ala Gly Met Ala Leu Val Phe Ala
1               5                   10                  15

Leu Gln Met Ser Gly Ile Phe Gln Phe Ala Val Arg Thr Gln Thr Glu
            20                  25                  30

Leu Glu Ala Lys Met Thr Cys Val Glu Arg Val Thr Tyr Tyr Ser Asp
        35                  40                  45

His Ile Lys Ser Glu Asp Gly Trp Asn Asn Gly Ile Gly Asp Ser Ser
    50                  55                  60

Arg Asn Asp Ser Phe Pro Asn Gly Cys Ile Val Phe Arg Gly Val Ser
65                  70                  75                  80

Leu Arg Tyr Arg Pro Asp Leu Pro Leu Ala Leu Asp Asp Val Asn Phe
                85                  90                  95

Arg Ile Glu Pro Lys Glu Lys Ile Gly Ile Ile Gly Arg Thr Gly Ser
            100                 105                 110

Gly Lys Thr Ser Leu Cys Asn Ala Leu Tyr Arg Leu Tyr Pro Leu Thr
        115                 120                 125

Ser Gly Ser Ile Glu Ile Asp Gly Ile Asn Ile Ala Cys Ile Gly Leu
    130                 135                 140

Tyr Arg Leu Arg Arg Ala Met Ala Val Ile Pro Gln Asp Pro Thr Leu
145                 150                 155                 160

Phe Val Gly Thr Ile Arg Phe Asn Ile Asp Pro Asn Asn Glu Phe Thr
                165                 170                 175

Asp Asp Gln Ile Trp Met Ser Leu Glu Lys Thr Tyr Leu Lys Asp Met
            180                 185                 190

Val Ser Ser Leu Asp Arg Lys Leu Asp Ser Pro Val Thr Glu Gly Gly
        195                 200                 205

Arg Asn Leu Ser Val Gly Glu Arg Gln Leu Phe Cys Met Ala Arg Ala
    210                 215                 220

Leu Leu Arg Gln Val Arg Ile Val Val Leu Asp Glu Ala Thr Gly Ser
225                 230                 235                 240

Leu Asp Asn Ala Thr Asp Arg His Ile Gln Lys Cys Leu Arg Glu Ala
                245                 250                 255

Phe Val Gly Cys Thr Val Met Ile Ile Ala His Arg Leu Glu Asn Val
            260                 265                 270

Leu Gly Leu Asp Lys Ile Leu His Met Lys Gln Gly Lys Ile Val Lys
        275                 280                 285

Tyr Asp Thr Ile Gln Asn Leu Ile Arg Asp Gln Asn His Pro Leu Arg
    290                 295                 300

Arg Leu Leu Asp Asn Gln Lys Leu Arg Arg Val Ile Arg Thr Gln Lys
305                 310                 315                 320

Glu Gln Ser Thr Lys Lys Asn Leu Glu Gln Ser Ser Lys Ile Ser Pro
                325                 330                 335

Asn Glu Ser Ser Gly Ser Ser Pro Glu Arg Ile His Ser Thr Phe Leu
            340                 345                 350

Ala Ser Asp Lys Thr Ser Pro Glu Thr Ser Glu Phe Glu Lys Ile Ser
        355                 360                 365

Asp Ser Ile Asp Lys Glu Ile Thr Thr Met Ser Asn Asp Asn Ser Asp
    370                 375                 380

Leu Glu Val Ile Asn Lys Ser Asp Ala Glu Ser Asn Cys
385                 390                 395
```

<210> SEQ ID NO 37
<211> LENGTH: 298
<212> TYPE: PRT
<213> ORGANISM: Artificial Sequence
<220> FEATURE:
<223> OTHER INFORMATION: Nas4 segment of Reprolysin-Mrp5-Nas4 (RMN) chimera

<400> SEQUENCE: 37

```
Ser Lys Leu Asp Ile Lys Leu Glu Asp Ile Ile Asn Glu Lys Ala Val
1               5                   10                  15

Glu Glu Glu Thr Thr Leu Thr Ala Glu Asp Phe Glu Lys Thr Ile Asp
            20                  25                  30

Glu Glu Phe Asn Leu Thr Leu Leu Gly Ile Gln Met Lys Pro Asp Pro
        35                  40                  45

Thr Met Gly Asn Met Thr Glu Gly Asp Ile Val Leu Pro Asn Phe Lys
    50                  55                  60

Ala Phe Ala Asp Tyr Arg Asn Asn Arg Thr Glu Arg Ser Ala Ala Arg
65                  70                  75                  80

His Ile Tyr Arg Arg Trp Pro Asn Ala Glu Ile Pro Tyr Ala Leu Ser
                85                  90                  95

Ser Arg Tyr Gly Ala Tyr Ser Arg Ser Val Ile Ala Lys Ala Met Lys
            100                 105                 110

Lys Phe His Asp Ile Ser Cys Val Arg Phe Val Pro Arg Val Tyr Asn
        115                 120                 125

Gln His Asp Asp Tyr Ile Tyr Ile Phe Pro His Asp Gly Cys Tyr Ser
    130                 135                 140

Phe Val Gly Arg Ser Gly Gly Arg Gln Pro Val Ser Leu Glu Ala Asn
145                 150                 155                 160

Cys Ile Gln Ser Gly Thr Ile Ile His Glu Leu Met His Val Val Gly
                165                 170                 175

Phe Phe His Glu Gln Ser Arg Pro Asp Arg Asp Glu Tyr Ile Glu Ile
            180                 185                 190

Met Trp Gln Asn Val Ile Arg Gly Ser Glu Asn Gln Phe Asp Lys Gln
        195                 200                 205

Ser Leu Arg Tyr Leu Asp Pro Leu Asn Glu Ser Tyr Asp Tyr Ser Ser
    210                 215                 220

Ile Met His Tyr Gly Pro Tyr Ala Phe Ser Gly Asn Gly Arg Arg Thr
225                 230                 235                 240

Ile Ile Ala Leu Lys Pro Gly Ala Gly Lys Met Gly Gln Arg Glu Ser
                245                 250                 255

Leu Thr Glu Ile Asp Ile Arg Lys Ile Asn Lys Leu Tyr His Cys Gln
            260                 265                 270

Gln Lys Ser Thr Gln Glu Asn Ser Ile Glu Asp Asn Val Glu Ile Thr
        275                 280                 285

Lys Ser Ile Val Pro Leu Lys Pro Ile Asn
    290                 295
```

<210> SEQ ID NO 38
<211> LENGTH: 1378
<212> TYPE: PRT
<213> ORGANISM: Artificial Sequence
<220> FEATURE:
<223> OTHER INFORMATION: RMN Chimera with 5' Murine IgK chain leader and 3' C-myc tag

<400> SEQUENCE: 38

-continued

```
Met Glu Thr Asp Thr Leu Leu Leu Trp Val Leu Leu Leu Trp Val Pro
1               5                   10                  15

Gly Ser Thr Gly Asp His His Asp Ile Tyr Cys Pro Leu His Ile Tyr
            20                  25                  30

Phe Gly Glu His Glu Leu Asp Ala Asn Gln Leu Ile Ser Ile Ser Gln
        35                  40                  45

Thr Ile Gln Pro Lys Phe Glu Leu Thr Leu Gln Asn Asp Phe Gly Glu
    50                  55                  60

Ser Arg Asp Phe Ile Phe Gln Ser Asn Arg Glu Leu Ser Lys Thr Ser
65                  70                  75                  80

Ser Lys Ile Asp Met Leu Cys His Phe Glu Gly Ile Ser Asn Thr Gly
                85                  90                  95

Glu His Ser Ala Met Ser Thr Cys Ser Met Ser Leu Leu Gly Gly Leu
            100                 105                 110

Phe Thr Ile Asn Gly Arg Arg Phe Val Leu Glu Val Gly Leu Asn Ala
        115                 120                 125

Leu Phe His Phe Val Pro Leu Ser Asp His Ser Cys Asp Trp Gly Leu
    130                 135                 140

Arg Ser Lys Arg Ser Ile Ala Gly Ser His Val Ala Glu Tyr Tyr Ala
145                 150                 155                 160

Gln Phe Leu Asp Gly Arg Trp Arg Tyr Val Glu Leu Ala Leu Ile Ala
                165                 170                 175

Asp Lys Leu Val Phe Glu Lys Tyr His Lys Asn Val Thr Glu Val Met
            180                 185                 190

Gln Arg Leu Asn Ala Ile Thr Asn Tyr Ile Asn Ser Leu Tyr Leu Pro
        195                 200                 205

Ile Asn Ile Arg Val Val Leu Val Trp Ala Asp Val Trp Thr Asn Asp
    210                 215                 220

Asn Pro Val Asp Ile Thr Ser Asn Ser Asp Thr Thr Leu Trp Asn Phe
225                 230                 235                 240

Leu Asn Trp Arg Lys Gly Leu Leu Lys Asp His Pro His Asp Asn Ala
                245                 250                 255

His Leu Leu Thr Gly Val Ile Phe Glu Asn Asn Val Val Gly Lys Ala
            260                 265                 270

Phe Lys Gly Thr Met Cys Ser Tyr Asp Phe Ser Gly Gly Val Asp Ile
        275                 280                 285

Glu His Ser Asp Gln Ala Ala Tyr Val Ala Ala Thr Ile Ala His Glu
    290                 295                 300

Met Gly His Asn Phe Gly Met Glu His Asp Ile Asp Glu Ile Glu Cys
305                 310                 315                 320

Arg Cys Pro Ala Lys Ser Cys Ile Met Ser Pro Ala Thr Gly Ile Thr
                325                 330                 335

His Pro Thr Phe Trp Ser Glu Cys Ser Met Arg Ala Leu Gln His Ser
            340                 345                 350

Phe Ser Arg Gly Val Asp Tyr Cys Leu Arg Asn Ser Pro Thr Ser Val
        355                 360                 365

Phe Gly Gly Ala Arg Cys Gly Asn Gly Ile Val Glu Ala Gly Glu Glu
    370                 375                 380

Cys Asp Cys Gly Thr Pro Ser Ser Cys Ile Asn Lys Cys Cys Asn Pro
385                 390                 395                 400

Ala Thr Cys Arg Leu Ser Glu Thr Ala Val Cys Ala Thr Gly Glu Cys
                405                 410                 415

Cys Asp Leu Asn Thr Cys Gln Leu Leu Ser Ala Thr Thr Val Cys Arg
```

-continued

```
            420                 425                 430

Gln Ala Thr Asn Glu Cys Asp Leu Pro Glu Tyr Cys Asp Gly Leu Met
        435                 440                 445

Glu His Cys Pro Ala Asp Phe Phe Val Gln Asp Gly His Glu Cys Pro
    450                 455                 460

Asn His Val Asp Asp Tyr Cys Tyr Asn Gly Tyr Cys Gly Ser Arg Asp
465                 470                 475                 480

Ala Gln Cys Gln His Ile Trp Gly Ser Thr Gly Arg Asn Ala Ala Pro
                485                 490                 495

Ala Cys Tyr Asp Leu Asn Leu Ser Gly Ser Ser Gly Gly Asn Cys Gly
            500                 505                 510

Phe Leu His Glu Thr Asn Arg Phe Val Pro Cys Asn Lys Asn Asp Ile
        515                 520                 525

Lys Cys Gly Arg Leu His Cys Ile His Glu Asn Glu Lys Leu Val Phe
    530                 535                 540

Gly Asp Pro Ser Thr Val Tyr Thr Ala Tyr Thr Gly Leu Arg Leu Arg
545                 550                 555                 560

Asn Gly Glu Asp Val Ala Cys Arg Val Ile Trp Thr Lys Tyr Ile Ser
                565                 570                 575

Gly Gln Lys Glu Pro Asp Pro Gly Met Val Pro Asn Gly Ala Val Cys
            580                 585                 590

Gly Gln Asp Glu Met Cys Val Asp Ala Lys Cys Gln Asn Arg Thr Ala
        595                 600                 605

Lys Val Leu Met Ala Pro Lys Cys Glu Pro Val Ser Cys Asn Asn Ala
    610                 615                 620

Gly Ile Cys Asn Asn Met Gly Asn Cys His Cys Asp Pro Gly Tyr Gly
625                 630                 635                 640

Gly Ser Ser Cys Ala Ile Pro Gly Pro Gly Gly Ser Val Asn Ser Gly
                645                 650                 655

Pro Ala Ile Glu Gly Gly Val Ile His Gly Ser Ser Gly Thr Gly Ser
            660                 665                 670

Ile Ala Pro Ala Asp Ala Gly Met Ala Leu Val Phe Ala Leu Gln Met
        675                 680                 685

Ser Gly Ile Phe Gln Phe Ala Val Arg Thr Gln Thr Glu Leu Glu Ala
    690                 695                 700

Lys Met Thr Cys Val Glu Arg Val Thr Tyr Tyr Ser Asp His Ile Lys
705                 710                 715                 720

Ser Glu Asp Gly Trp Asn Asn Gly Ile Gly Asp Ser Ser Arg Asn Asp
                725                 730                 735

Ser Phe Pro Asn Gly Cys Ile Val Phe Arg Gly Val Ser Leu Arg Tyr
            740                 745                 750

Arg Pro Asp Leu Pro Leu Ala Leu Asp Asp Val Asn Phe Arg Ile Glu
        755                 760                 765

Pro Lys Glu Lys Ile Gly Ile Ile Gly Arg Thr Gly Ser Gly Lys Thr
    770                 775                 780

Ser Leu Cys Asn Ala Leu Tyr Arg Leu Tyr Pro Leu Thr Ser Gly Ser
785                 790                 795                 800

Ile Glu Ile Asp Gly Ile Asn Ile Ala Cys Ile Gly Leu Tyr Arg Leu
                805                 810                 815

Arg Arg Ala Met Ala Val Ile Pro Gln Asp Pro Thr Leu Phe Val Gly
            820                 825                 830

Thr Ile Arg Phe Asn Ile Asp Pro Asn Asn Glu Phe Thr Asp Asp Gln
        835                 840                 845
```

```
Ile Trp Met Ser Leu Glu Lys Thr Tyr Leu Lys Asp Met Val Ser Ser
    850                 855                 860

Leu Asp Arg Lys Leu Asp Ser Pro Val Thr Glu Gly Gly Arg Asn Leu
865                 870                 875                 880

Ser Val Gly Glu Arg Gln Leu Phe Cys Met Ala Arg Ala Leu Leu Arg
                885                 890                 895

Gln Val Arg Ile Val Val Leu Asp Glu Ala Thr Gly Ser Leu Asp Asn
            900                 905                 910

Ala Thr Asp Arg His Ile Gln Lys Cys Leu Arg Glu Ala Phe Val Gly
        915                 920                 925

Cys Thr Val Met Ile Ile Ala His Arg Leu Glu Asn Val Leu Gly Leu
    930                 935                 940

Asp Lys Ile Leu His Met Lys Gln Gly Lys Ile Val Lys Tyr Asp Thr
945                 950                 955                 960

Ile Gln Asn Leu Ile Arg Asp Gln Asn His Pro Leu Arg Arg Leu Leu
                965                 970                 975

Asp Asn Gln Lys Leu Arg Arg Val Ile Arg Thr Gln Lys Glu Gln Ser
            980                 985                 990

Thr Lys Lys Asn Leu Glu Gln Ser  Ser Lys Ile Ser Pro  Asn Glu Ser
        995                 1000                1005

Ser Gly  Ser Ser Pro Glu Arg  Ile His Ser Thr Phe  Leu Ala Ser
    1010                1015                1020

Asp Lys  Thr Ser Pro Glu Thr  Ser Glu Phe Glu Lys  Ile Ser Asp
    1025                1030                1035

Ser Ile  Asp Lys Glu Ile Thr  Thr Met Ser Asn Asp  Asn Ser Asp
    1040                1045                1050

Leu Glu  Val Ile Asn Lys Ser  Asp Ala Glu Ser Asn  Cys Gly Ser
    1055                1060                1065

Ser Gly  Ser Lys Leu Asp Ile  Lys Leu Glu Asp Ile  Ile Asn Glu
    1070                1075                1080

Lys Ala  Val Glu Glu Glu Thr  Thr Leu Thr Ala Glu  Asp Phe Glu
    1085                1090                1095

Lys Thr  Ile Asp Glu Glu Phe  Asn Leu Thr Leu Leu  Gly Ile Gln
    1100                1105                1110

Met Lys  Pro Asp Pro Thr Met  Gly Asn Met Thr Glu  Gly Asp Ile
    1115                1120                1125

Val Leu  Pro Asn Phe Lys Ala  Phe Ala Asp Tyr Arg  Asn Asn Arg
    1130                1135                1140

Thr Glu  Arg Ser Ala Ala Arg  His Ile Tyr Arg Arg  Trp Pro Asn
    1145                1150                1155

Ala Glu  Ile Pro Tyr Ala Leu  Ser Ser Arg Tyr Gly  Ala Tyr Ser
    1160                1165                1170

Arg Ser  Val Ile Ala Lys Ala  Met Lys Lys Phe His  Asp Ile Ser
    1175                1180                1185

Cys Val  Arg Phe Val Pro Arg  Val Tyr Asn Gln His  Asp Asp Tyr
    1190                1195                1200

Ile Tyr  Ile Phe Pro His Asp  Gly Cys Tyr Ser Phe  Val Gly Arg
    1205                1210                1215

Ser Gly  Gly Arg Gln Pro Val  Ser Leu Glu Ala Asn  Cys Ile Gln
    1220                1225                1230

Ser Gly  Thr Ile Ile His Glu  Leu Met His Val Val  Gly Phe Phe
    1235                1240                1245
```

His Glu Gln Ser Arg Pro Asp Arg Asp Glu Tyr Ile Glu Ile Met
1250 1255 1260

Trp Gln Asn Val Ile Arg Gly Ser Glu Asn Gln Phe Asp Lys Gln
1265 1270 1275

Ser Leu Arg Tyr Leu Asp Pro Leu Asn Glu Ser Tyr Asp Tyr Ser
1280 1285 1290

Ser Ile Met His Tyr Gly Pro Tyr Ala Phe Ser Gly Asn Gly Arg
1295 1300 1305

Arg Thr Ile Ile Ala Leu Lys Pro Gly Ala Gly Lys Met Gly Gln
1310 1315 1320

Arg Glu Ser Leu Thr Glu Ile Asp Ile Arg Lys Ile Asn Lys Leu
1325 1330 1335

Tyr His Cys Gln Gln Lys Ser Thr Gln Glu Asn Ser Ile Glu Asp
1340 1345 1350

Asn Val Glu Ile Thr Lys Ser Ile Val Pro Leu Lys Pro Ile Asn
1355 1360 1365

Glu Gln Lys Leu Ile Ser Glu Glu Asp Leu
1370 1375

<210> SEQ ID NO 39
<211> LENGTH: 1932
<212> TYPE: DNA
<213> ORGANISM: Artificial Sequence
<220> FEATURE:
<223> OTHER INFORMATION: Reprolysine segment of RMN chimera

<400> SEQUENCE: 39
catcatgata tctattgccc tttacacatt tactttggtg agcatgaatt ggacgccaat 60
cagctaatca gcatttctca aactattcaa cccaaattcg aactgacact ccagaacgac 120
ttcggcgaga gtagggactt cattttccaa tccaatcgtg aactcagcaa gacatcctcg 180
aagatcgaca tgttgtgcca tttcgaaggt atctcaaaca cgggagaaca cagtgccatg 240
tcaacttgca gtatgtcatt attgggcggc ttgtttacta tcaacggccg tcgattcgtc 300
ttggaagtgg gcctgaatgc cctgtttcac ttcgtccctt tgtctgatca ttcctgtgat 360
tggggattac gtagtaaacg ttccatcgcc ggtagccatg ttgccgagta ctatgcccaa 420
ttcttggatg gtcgatggag gtacgtagag ctggctctga ttgcggataa gctcgtcttt 480
gaaaagtacc acaagaacgt aactgaggtc atgcagcgct tgaatgccat tacaaactac 540
ataaactctc tgtatctccc catcaacatc cgtgttgtgc tcgtctgggc tgacgtctgg 600
accaacgata accctgtcga tattacgtcc aatagcgata ccaccctttg gaacttctta 660
aattggcgta agggcctgct aaaggaccac cctcacgata acgcccatct gctgacagga 720
gtgatcttcg agaataacgt ggtgggaaag gcatttaagg gtaccatgtg ctcttacgac 780
ttcagcggcg gcgttgatat cgagcattcc gatcaagccg cgtatgtggc agcaacgatt 840
gctcacgaaa tgggccacaa cttcggcatg gaacatgaca tcgacgagat tgagtgtcgt 900
tgccctgcga agtcttgcat tatgtcccca gcaacgggta taacacaccc gaccttctgg 960
agcgagtgta gtatgagagc tttgcaacac tctttctctc gcggcgttga ctactgcctg 1020
cgcaacagcc cgacttccgt gttcggagga gctcgctgcg gtaatggtat cgttgaggct 1080
ggagaggaat gcgattgtgg cacaccttcc tcctgcatca acaaatgctg taacccagct 1140
acttgccgtc tgtccgaaac agccgtttgt gctacaggag aatgctgtga cctgaacacc 1200
tgtcagctgc tatcggccac taccgtgtgc aggcaagcta ctaatgagtg cgaccttccc 1260

-continued gagtattgtg acggtctgat ggaacattgc cctgcggact tcttcgtaca agacggtcac 1320
gaatgcccta atcacgttga cgactactgc tacaacggtt attgcggttc cagagatgcg 1380
cagtgtcagc atatctgggg ttcaaccggt cgtaatgctg caccagcctg ttacgacctt 1440
aacttgtctg gaagcagcgg aggaaactgc ggatttctgc acgagactaa tcgcttcgtt 1500
ccatgcaaca agaacgacat caagtgtggt aggctacact gcattcatga gaacgagaaa 1560
ctggttttcg gagatccctc aacggtttac accgcttaca ctggcttgag actgcgtaac 1620
ggtgaggacg tcgcgtgtag ggtcatatgg acaaaatata tctcaggtca gaaggaacct 1680
gaccccggta tggtcccgaa cggtgcggta tgcggccaag acgagatgtg cgtagatgcc 1740
aagtgccaga atagaaccgc taaagtcttg atggctccaa agtgcgaacc ggtatcctgc 1800
aacaacgcag gcatctgtaa caatatgggt aactgtcatt gcgaccccgg ttacggcgga 1860
tcatcatgtg ccattccggg ccctggtggt tccgtaaaca gcggtcccgc tattgaggga 1920
ggagtgatcc ac 1932

<210> SEQ ID NO 40
<211> LENGTH: 1191
<212> TYPE: DNA
<213> ORGANISM: Artificial Sequence
<220> FEATURE:
<223> OTHER INFORMATION: Mrp5 segment of Reprolysin-Mrp5-Nas4 (RMN) chimera

<400> SEQUENCE: 40
acgggaagta tcgctcccgc tgacgccggc atggccctcg tgtttgctct ccaaatgtct 60
ggaattttcc agttcgcggt ccgcacacag accgaactgg aggctaagat gacatgcgtg 120
gagagggtta cgtactactc agatcacatt aagtcggagg acggctggaa caacggtatt 180
ggtgattctt caaggaatga ctccttcccc aacggttgca tcgtgttcag gggagtgtct 240
ctgcgatacc gcccagactt gcccttagct ttggacgacg tcaacttccg tatagaaccg 300
aaagaaaaaa ttggtatcat aggacgtacg ggtagcggca aaacctcatt gtgtaacgct 360
ctgtatcgcc tctacccttt aacctcggga agcatcgaga tagacggtat taacatagct 420
tgtataggac tgtatcgcct tcgcagagca atggcggtta ttccgcagga ccctacgctc 480
tttgtaggaa ctatccgctt caacatcgac ccaaataatg aattcaccga tgaccaaatc 540
tggatgagct tggaaaagac atacctcaaa gacatggtgt caagtcttga cagaaaactg 600
gatagtcccg tgaccgaggg cggccgtaat ctaagcgtag gcgagagaca gttgttctgt 660
atggcgagag cactcttgcg acaagtcagg atcgtcgtgc tggatgaggc gacgggctcc 720
ttggataatg caactgatcg tcacatccag aagtgtctca gagaagcatt tgtgggttgc 780
acagtgatga ttatcgctca cagacttgag aatgttctag gcctggacaa aatcttgcac 840
atgaaacagg gtaaaatcgt caaatacgat acaatccaga accttatcag ggaccagaat 900
catccactgc gaagattgct cgacaaccag aagcttaggc gtgtgattcg cacgcaaaag 960
gaacagtcga caaagaagaa cctcgaacaa agctctaaga tcagcccaaa tgaatcctcc 1020
ggctctagtc cagagcgcat acattcgact tttcttgctt cggacaagac gagtccagag 1080
acaagcgagt tcgaaaagat atcagactcc atcgataagg agatcaccac tatgtcgaac 1140
gacaactcag atctggaggt gatcaataag agtgacgccg agtccaactg c 1191

<210> SEQ ID NO 41
<211> LENGTH: 894
<212> TYPE: DNA

<213> ORGANISM: Artificial Sequence
<220> FEATURE:
<223> OTHER INFORMATION: Nas4 segment of Reprolysin-Mrp5-Nas4 (RMN) chimera

<400> SEQUENCE: 41

```
tcaaagcttg acataaaact tgaggacatt attaacgaaa aggctgtgga ggaagaaacc     60

actctgactg ccgaggattt tgagaaaact attgacgaag agttcaacct cactctcctc    120

ggtatacaaa tgaagccaga cccaaccatg ggtaatatga ctgaaggtga tatcgttctc    180

cccaacttca aggcattcgc agactatcgc aacaacagga ccgagcgtag tgccgcccga    240

cacatttaca ggagatggcc caacgcagag atcccgtacg ccctatcgag tcgctacgga    300

gcttactcta ggtccgtgat agcgaaagcc atgaagaagt tccacgacat ctcatgtgta    360

agatttgtcc caagggtata caaccaacac gatgactata tctacatttt ccctcacgat    420

ggttgctact ctttcgtggg tagatcaggt ggccgccaac ctgtaagcct cgaagctaac    480

tgtatccagt cgggtacaat cattcacgaa ctgatgcacg tcgtcggttt ctttcacgag    540

caatcacgcc cagatcgcga cgaatacatc gaaatcatgt ggcagaatgt tatccgcggt    600

tcggaaaatc agttcgataa gcagtcgctg cgctacctcg atcccctgaa cgaatcttat    660

gattactcct ccattatgca ctacggccct tatgcattct cgggtaacgg acgccgtacc    720

attatcgcgc tcaagcctgg cgctggcaaa atgggtcagc gtgaatcact caccgagatc    780

gacatccgca aaatcaacaa actgtaccac tgccaacaga agtctaccca ggaaaacagc    840

atagaggata acgtggagat cactaaaagc atagtgcccc taaagcccat caac          894
```

<210> SEQ ID NO 42
<211> LENGTH: 4134
<212> TYPE: DNA
<213> ORGANISM: Artificial Sequence
<220> FEATURE:
<223> OTHER INFORMATION: RMN Chimera with 5' Murine IgK chain leader and 3' C-myc tag

<400> SEQUENCE: 42

```
atggaaaccg acacgctatt actttgggtc ttactgttat gggtcccggg aagtaccgga     60

gatcatcatg atatctattg ccctttacac atttactttg gtgagcatga attggacgcc    120

aatcagctaa tcagcatttc tcaaactatt caacccaaat tcgaactgac actccagaac    180

gacttcggcg agagtaggga cttcattttc caatccaatc gtgaactcag caagacatcc    240

tcgaagatcg acatgttgtg ccatttcgaa ggtatctcaa acacgggaga acacagtgcc    300

atgtcaactt gcagtatgtc attattgggc ggcttgttta ctatcaacgg ccgtcgattc    360

gtcttggaag tgggcctgaa tgccctgttt cacttcgtcc ctttgtctga tcattcctgt    420

gattggggat tacgtagtaa acgttccatc gccggtagcc atgttgccga gtactatgcc    480

caattcttgg atggtcgatg gaggtacgta gagctggctc tgattgcgga taagctcgtc    540

tttgaaaagt accacaagaa cgtaactgag gtcatgcagc gcttgaatgc cattacaaac    600

tacataaact ctctgtatct ccccatcaac atccgtgttg tgctcgtctg ggctgacgtc    660

tggaccaacg ataaccctgt cgatattacg tccaatagcg ataccaccct ttggaacttc    720

ttaaattggc gtaagggcct gctaaaggac caccctcacg ataacgccca tctgctgaca    780

ggagtgatct tcgagaataa cgtggtggga aaggcattta agggtaccat gtgctcttac    840

gacttcagcg gcggcgttga tatcgagcat tccgatcaag ccgcgtatgt ggcagcaacg    900

attgctcacg aaatgggcca caacttcggc atggaacatg acatcgacga gattgagtgt    960
```

-continued

```
cgttgccctg cgaagtcttg cattatgtcc ccagcaacgg gtataacaca cccgaccttc   1020
tggagcgagt gtagtatgag agctttgcaa cactctttct ctcgcggcgt tgactactgc   1080
ctgcgcaaca gcccgacttc cgtgttcgga ggagctcgct gcggtaatgg tatcgttgag   1140
gctggagagg aatgcgattg tggcacacct tcctcctgca tcaacaaatg ctgtaaccca   1200
gctacttgcc gtctgtccga aacagccgtt tgtgctacag gagaatgctg tgacctgaac   1260
acctgtcagc tgctatcggc cactaccgtg tgcaggcaag ctactaatga gtgcgacctt   1320
cccgagtatt gtgacggtct gatggaacat tgccctgcgg acttcttcgt acaagacggt   1380
cacgaatgcc ctaatcacgt tgacgactac tgctacaacg gttattgcgg ttccagagat   1440
gcgcagtgtc agcatatctg ggttcaacc ggtcgtaatg ctgcaccagc ctgttacgac   1500
cttaacttgt ctggaagcag cggaggaaac tgcggatttc tgcacgagac taatcgcttc   1560
gttccatgca acaagaacga catcaagtgt ggtaggctac actgcattca tgagaacgag   1620
aaactggttt tcggagatcc ctcaacggtt tacaccgctt acactggctt gagactgcgt   1680
aacggtgagg acgtcgcgtg tagggtcata tggacaaaat atatctcagg tcagaaggaa   1740
cctgaccccg gtatggtccc gaacggtgcg gtatgcggcc aagacgagat gtgcgtagat   1800
gccaagtgcc agaatagaac cgctaaagtc ttgatggctc caaagtgcga accggtatcc   1860
tgcaacaacg caggcatctg taacaatatg ggtaactgtc attgcgaccc cggttacggc   1920
ggatcatcat gtgccattcc gggccctggt ggttccgtaa acagcggtcc cgctattgag   1980
ggaggagtga tccacggcag ttctggaacg ggaagtatcg ctcccgctga cgccggcatg   2040
gccctcgtgt ttgctctcca aatgtctgga attttccagt tcgcggtccg cacacagacc   2100
gaactggagg ctaagatgac atgcgtggag agggttacgt actactcaga tcacattaag   2160
tcggaggacg gctggaacaa cggtattggt gattcttcaa ggaatgactc cttccccaac   2220
ggttgcatcg tgttcagggg agtgtctctg cgataccgcc cagacttgcc cttagctttg   2280
gacgacgtca acttccgtat agaaccgaaa gaaaaaattg gtatcatagg acgtacgggt   2340
agcggcaaaa cctcattgtg taacgctctg tatcgcctct accctttaac ctcgggaagc   2400
atcgagatag acggtattaa catagcttgt ataggactgt atcgccttcg cagagcaatg   2460
gcggttattc cgcaggaccc tacgctcttt gtaggaacta tccgcttcaa catcgaccca   2520
aataatgaat tcaccgatga ccaaatctgg atgagcttgg aaaagacata cctcaaagac   2580
atggtgtcaa gtcttgacag aaaactggat agtcccgtga ccgagggcgg ccgtaatcta   2640
agcgtaggcg agagacagtt gttctgtatg gcgagagcac tcttgcgaca agtcaggatc   2700
gtcgtgctgg atgaggcgac gggctccttg gataatgcaa ctgatcgtca catccagaag   2760
tgtctcagag aagcatttgt gggttgcaca gtgatgatta tcgctcacag acttgagaat   2820
gttctaggcc tggacaaaat cttgcacatg aaacagggta aaatcgtcaa atacgataca   2880
atccagaacc ttatcaggga ccagaatcat ccactgcgaa gattgctcga caaccagaag   2940
cttaggcgtg tgattcgcac gcaaaaggaa cagtcgacaa agaagaacct cgaacaaagc   3000
tctaagatca gcccaaatga atcctccggc tctagtccag agcgcataca ttcgactttt   3060
cttgcttcgg acaagacgag tccagagaca agcgagttcg aaaagatatc agactccatc   3120
gataaggaga tcaccactat gtcgaacgac aactcagatc tggaggtgat caataagagt   3180
gacgccgagt ccaactgcgg ctcgtctgga tcaaagcttg acataaaact tgaggacatt   3240
attaacgaaa aggctgtgga ggaagaaacc actctgactg ccgaggattt tgagaaaact   3300
```

```
attgacgaag agttcaacct cactctcctc ggtatacaaa tgaagccaga cccaaccatg   3360

ggtaatatga ctgaaggtga tatcgttctc cccaacttca aggcattcgc agactatcgc   3420

aacaacagga ccgagcgtag tgccgcccga cacatttaca ggagatggcc caacgcagag   3480

atcccgtacg ccctatcgag tcgctacgga gcttactcta ggtccgtgat agcgaaagcc   3540

atgaagaagt tccacgacat ctcatgtgta agatttgtcc caagggtata caaccaacac   3600

gatgactata tctacatttt ccctcacgat ggttgctact ctttcgtggg tagatcaggt   3660

ggccgccaac ctgtaagcct cgaagctaac tgtatccagt cgggtacaat cattcacgaa   3720

ctgatgcacg tcgtcggttt ctttcacgag caatcacgcc cagatcgcga cgaatacatc   3780

gaaatcatgt ggcagaatgt tatccgcggt tcggaaaatc agttcgataa gcagtcgctg   3840

cgctacctcg atcccctgaa cgaatcttat gattactcct ccattatgca ctacggccct   3900

tatgcattct cgggtaacgg acgccgtacc attatcgcgc tcaagcctgg cgctggcaaa   3960

atgggtcagc gtgaatcact caccgagatc gacatccgca aaatcaacaa actgtaccac   4020

tgccaacaga agtctaccca ggaaaacagc atagaggata acgtggagat cactaaaagc   4080

atagtgcccc taaagcccat caacgagcag aagcttatct ctgaggagga ctta         4134


<210> SEQ ID NO 43
<211> LENGTH: 95
<212> TYPE: PRT
<213> ORGANISM: Artificial Sequence
<220> FEATURE:
<223> OTHER INFORMATION: Fat3 segment of Fat3-Enolase-DiTG-Tropomyosin
      (FEDT) chimera

<400> SEQUENCE: 43

Cys Trp Gln Gln Phe Gly Trp Leu Thr His Asp Phe Cys His Gln Gln
1               5                   10                  15

Pro Ser Lys Asn Arg Glu Lys Asn Asp Phe Tyr Ser Leu Ile Phe Gly
            20                  25                  30

Asn Ile Val Gln Gly Phe Ser Arg Asp Trp Trp Lys Glu Lys His Asn
        35                  40                  45

Thr His His Ala Ala Thr Asn Ile Val Gly Gln Asp Gly Asp Ile Asp
    50                  55                  60

Leu Ala Pro Leu Leu Ala Phe Val Pro Asp Asp Leu Lys Lys Tyr Lys
65                  70                  75                  80

Ala Leu Phe Glu Gln Phe Ile Ser Lys Ile Ile Pro Tyr Gln His
                85                  90                  95


<210> SEQ ID NO 44
<211> LENGTH: 435
<212> TYPE: PRT
<213> ORGANISM: Artificial Sequence
<220> FEATURE:
<223> OTHER INFORMATION: Enolase segment of Fat3 FEDT chimera

<400> SEQUENCE: 44

Pro Ile Thr Arg Val His Ala Arg Pro Ile Tyr Asp Ser Arg Gly Asn
1               5                   10                  15

Pro Thr Val Glu Val Asp Leu Thr Thr Glu Lys Gly Ile Phe Arg Ala
            20                  25                  30

Ala Val Pro Ser Gly Ala Ser Thr Gly Val His Glu Ala Leu Glu Leu
        35                  40                  45

Arg Asp Asn Asp Lys Ala Val Asn His Gly Lys Gly Val Leu Gln Ala
    50                  55                  60
```

```
Val Arg Asn Val Asn Glu His Ile Gly Pro Ala Leu Val Ala Lys Asn
65                  70                  75                  80

Phe Cys Pro Thr Gln Gln Arg Glu Ile Asp His Phe Met Leu Glu Leu
                85                  90                  95

Asp Gly Thr Glu Asn Lys Ala Lys Leu Gly Ala Asn Ala Ile Leu Gly
            100                 105                 110

Val Ser Leu Ala Val Cys Lys Ala Gly Ala Val His Lys Gly Val Pro
        115                 120                 125

Leu Tyr Lys Tyr Ile Ala Glu Leu Ala Gly Thr Gly Gln Val Val Leu
    130                 135                 140

Pro Val Pro Ala Met Asn Val Ile Asn Gly Gly Ser His Ala Gly Asn
145                 150                 155                 160

Lys Leu Ala Met Gln Glu Phe Met Ile Met Pro Ile Gly Ala Ser Ser
                165                 170                 175

Phe Ser Glu Ala Met Arg Met Gly Ser Glu Ile Tyr His Tyr Leu Lys
            180                 185                 190

Ala Glu Ile Lys Lys Arg Tyr Gly Leu Asp Ala Thr Ala Val Gly Asp
        195                 200                 205

Glu Gly Gly Phe Ala Pro Asn Ile Gln Asp Asn Arg Glu Gly Leu Asp
    210                 215                 220

Leu Leu Asn Thr Ala Ile Ala Thr Ala Gly Tyr Thr Gly Lys Val Ala
225                 230                 235                 240

Ile Ala Met Asp Cys Ala Ala Ser Glu Tyr Tyr Lys Glu Ser Asp Lys
                245                 250                 255

Leu Tyr Asp Leu Asp Phe Lys Asn Pro Asn Ser Asp Lys Thr Gln Trp
            260                 265                 270

Lys Thr Gly Asp Gln Met Met Glu Ile Tyr Gln Ser Phe Ile Lys Glu
        275                 280                 285

Tyr Pro Val Val Ser Ile Glu Asp Trp Phe Asp Gln Asp Asp Trp Asp
    290                 295                 300

Asn Trp Thr Lys Ala Leu Ala Asn Thr His Ile Gln Ile Val Gly Asp
305                 310                 315                 320

Asp Leu Thr Val Thr Asn Pro Lys Arg Ile Ala Leu Ala Ala Glu Lys
                325                 330                 335

Lys Ala Cys Asn Cys Leu Leu Leu Lys Val Asn Gln Ile Gly Ser Val
            340                 345                 350

Thr Glu Ser Ile Asp Ala Ala Asn Leu Ala Arg Lys Asn Gly Trp Gly
        355                 360                 365

Val Met Val Ser His Arg Ser Gly Glu Thr Glu Asp Thr Phe Ile Ala
    370                 375                 380

Asp Leu Val Val Gly Leu Ala Thr Gly Gln Ile Lys Thr Gly Ala Pro
385                 390                 395                 400

Cys Arg Ser Glu Arg Leu Ala Lys Tyr Asn Gln Ile Leu Arg Ile Glu
                405                 410                 415

Glu Glu Leu Gly Ser Ala Ala Ile Tyr Ala Gly Gln Lys Phe Arg Asn
            420                 425                 430

Pro Gln Ala
        435
```

<210> SEQ ID NO 45
<211> LENGTH: 467
<212> TYPE: PRT
<213> ORGANISM: Artificial Sequence
<220> FEATURE:
<223> OTHER INFORMATION: DiTG segment of FEDT chimera

<400> SEQUENCE: 45

Lys Phe Thr Asp Ala Asp Phe Lys Glu Gly Ile Lys Pro Tyr Asp Val
1               5                   10                  15

Leu Leu Val Lys Phe Tyr Ala Pro Trp Cys Gly His Cys Lys Lys Ile
            20                  25                  30

Ala Pro Glu Phe Glu Lys Ala Ala Thr Lys Leu Leu Gln Asn Asp Pro
        35                  40                  45

Pro Ile His Leu Ala Glu Val Asp Cys Thr Glu Glu Lys Lys Thr Cys
    50                  55                  60

Asp Glu Tyr Gly Val Ser Gly Phe Pro Thr Leu Lys Ile Phe Arg Lys
65                  70                  75                  80

Gly Glu Leu Ala Gln Asp Tyr Asp Gly Pro Arg Val Ala Glu Gly Ile
                85                  90                  95

Val Lys Tyr Met Arg Gly Gln Ala Gly Pro Ser Ala Thr Glu Ile Asn
            100                 105                 110

Thr Gln Gln Glu Phe Glu Lys Met Leu Gln Ala Asp Asp Val Thr Ile
        115                 120                 125

Cys Gly Phe Phe Glu Glu Asn Ser Lys Leu Lys Asp Ser Phe Leu Lys
    130                 135                 140

Val Ala Asp Thr Glu Arg Asp Arg Phe Lys Phe Val Trp Thr Ser Asn
145                 150                 155                 160

Lys Gln Ile Leu Glu Ser Arg Gly Tyr Asn Asp Asp Ile Val Ala Tyr
                165                 170                 175

Gln Pro Lys Lys Phe His Asn Lys Phe Glu Pro Asn Glu Phe Lys Tyr
            180                 185                 190

Asp Gly Asn Tyr Asp Thr Asp Lys Ile Lys Glu Phe Leu Leu His Glu
        195                 200                 205

Thr Asn Gly Leu Val Gly Ile Arg Thr Ala Glu Asn Arg Tyr Gln Tyr
    210                 215                 220

Asp Leu Leu Pro Met Phe Val Val Tyr Gly Lys Val Asp Tyr Glu Leu
225                 230                 235                 240

Asp Pro Lys Gly Ser Asn Tyr Trp Arg Asn Arg Val Leu Met Val Ala
                245                 250                 255

Lys Asp Tyr Lys Arg Lys Ala Asn Phe Ala Met Ser Asn Lys Glu Asp
            260                 265                 270

Phe Ser Phe Asp Leu Asp Glu Phe Gly Leu Ala Asn Arg Lys Asp Thr
        275                 280                 285

Lys Pro Leu Val Ala Ala Arg Ser Lys Lys Gly Lys Phe Phe Met Lys
    290                 295                 300

Glu Glu Phe Ser Phe Ser Val Glu Asn Leu Lys Lys Phe Val Glu Asp
305                 310                 315                 320

Val Ile Gly Asp Arg Leu Glu Pro Tyr Met Lys Ser Glu Glu Ala Pro
                325                 330                 335

Glu Asp Gln Gly Asp Val Lys Val Val Val Ala Lys Thr Phe Gln Glu
            340                 345                 350

Met Ile Met Asn Val Glu Lys Asp Val Leu Ile Glu Phe Tyr Ala Pro
        355                 360                 365

Trp Cys Gly His Cys Lys Ala Leu Ala Pro Lys Tyr Asp Glu Leu Gly
    370                 375                 380

Gln Lys Leu Ser Gly Glu Pro Gly Val Val Ile Ala Lys Met Asp Ala
385                 390                 395                 400

Thr Ala Asn Asp Val Pro Pro Pro Phe Gln Val Gln Gly Phe Pro Thr

```
                405                 410                 415

Leu Tyr Trp Val Pro Lys Asn Lys Lys Asp Lys Pro Glu Pro Tyr Ser
            420                 425                 430

Gly Gly Arg Glu Val Asp Asp Phe Ile Lys Tyr Ile Ala Lys His Ala
        435                 440                 445

Thr Glu Glu Leu Lys Gly Tyr Lys Arg Asp Gly Lys Pro Lys Lys Lys
    450                 455                 460

Glu Glu Leu
465


<210> SEQ ID NO 46
<211> LENGTH: 253
<212> TYPE: PRT
<213> ORGANISM: Artificial Sequence
<220> FEATURE:
<223> OTHER INFORMATION: Tropomyosin segment of FEDT chimera

<400> SEQUENCE: 46

Thr Asp Lys Leu Glu Arg Ile Glu Glu Glu Leu Arg Asp Thr Gln Lys
1               5                   10                  15

Lys Met Met Gln Thr Glu Asn Asp Leu Asp Lys Ala Gln Glu Asp Leu
            20                  25                  30

Ala Val Ala Asn Thr Asn Leu Glu Glu Lys Glu Lys Lys Val Gln Glu
        35                  40                  45

Ala Glu Ala Glu Val Ala Ala Leu Asn Arg Arg Met Thr Leu Leu Glu
    50                  55                  60

Glu Glu Leu Glu Arg Ala Glu Glu Arg Leu Lys Ile Ala Thr Asp Lys
65                  70                  75                  80

Leu Glu Glu Ala Thr His Thr Ala Asp Glu Ser Glu Arg Val Arg Lys
                85                  90                  95

Val Met Glu Asn Arg Ser Phe Gln Asp Glu Glu Arg Ala Asn Thr Val
            100                 105                 110

Glu Ser Gln Leu Lys Glu Ala Gln Leu Leu Ala Glu Glu Ala Asp Arg
        115                 120                 125

Lys Tyr Asp Glu Val Ala Arg Lys Leu Ala Met Val Glu Ala Asp Leu
    130                 135                 140

Glu Arg Ala Glu Glu Arg Ala Glu Ala Gly Glu Asn Lys Ile Val Glu
145                 150                 155                 160

Leu Glu Glu Glu Leu Arg Val Val Gly Asn Asn Leu Lys Ser Leu Glu
                165                 170                 175

Val Ser Glu Glu Lys Ala Leu Gln Arg Glu Asp Ser Tyr Glu Glu Gln
            180                 185                 190

Ile Arg Thr Val Ser Ala Arg Leu Lys Glu Ala Glu Thr Arg Ala Glu
        195                 200                 205

Phe Ala Glu Arg Ser Val Gln Lys Leu Gln Lys Glu Val Asp Arg Leu
    210                 215                 220

Glu Asp Glu Leu Val His Glu Lys Glu Arg Tyr Lys Asn Ile Ser Glu
225                 230                 235                 240

Glu Leu Asp Gln Thr Phe Gln Glu Leu Ser Gly Tyr Glu
                245                 250


<210> SEQ ID NO 47
<211> LENGTH: 1292
<212> TYPE: PRT
<213> ORGANISM: Artificial Sequence
<220> FEATURE:
<223> OTHER INFORMATION: FEDT Chimera with 5' Murine IgK chain leader
```

and 3' C-myc tag

<400> SEQUENCE: 47

```
Met Glu Thr Asp Thr Leu Leu Leu Trp Val Leu Leu Leu Trp Val Pro
1               5                   10                  15

Gly Ser Thr Gly Asp Cys Trp Gln Gln Phe Gly Trp Leu Thr His Asp
            20                  25                  30

Phe Cys His Gln Gln Pro Ser Lys Asn Arg Glu Lys Asn Asp Phe Tyr
        35                  40                  45

Ser Leu Ile Phe Gly Asn Ile Val Gln Gly Phe Ser Arg Asp Trp Trp
    50                  55                  60

Lys Glu Lys His Asn Thr His His Ala Ala Thr Asn Ile Val Gly Gln
65                  70                  75                  80

Asp Gly Asp Ile Asp Leu Ala Pro Leu Leu Ala Phe Val Pro Asp Asp
                85                  90                  95

Leu Lys Lys Tyr Lys Ala Leu Phe Glu Gln Phe Ile Ser Lys Ile Ile
            100                 105                 110

Pro Tyr Gln His Gly Ser Ser Gly Pro Ile Thr Arg Val His Ala Arg
        115                 120                 125

Pro Ile Tyr Asp Ser Arg Gly Asn Pro Thr Val Glu Val Asp Leu Thr
    130                 135                 140

Thr Glu Lys Gly Ile Phe Arg Ala Ala Val Pro Ser Gly Ala Ser Thr
145                 150                 155                 160

Gly Val His Glu Ala Leu Glu Leu Arg Asp Asn Asp Lys Ala Val Asn
                165                 170                 175

His Gly Lys Gly Val Leu Gln Ala Val Arg Asn Val Asn Glu His Ile
            180                 185                 190

Gly Pro Ala Leu Val Ala Lys Asn Phe Cys Pro Thr Gln Gln Arg Glu
        195                 200                 205

Ile Asp His Phe Met Leu Glu Leu Asp Gly Thr Glu Asn Lys Ala Lys
    210                 215                 220

Leu Gly Ala Asn Ala Ile Leu Gly Val Ser Leu Ala Val Cys Lys Ala
225                 230                 235                 240

Gly Ala Val His Lys Gly Val Pro Leu Tyr Lys Tyr Ile Ala Glu Leu
                245                 250                 255

Ala Gly Thr Gly Gln Val Val Leu Pro Val Pro Ala Met Asn Val Ile
            260                 265                 270

Asn Gly Gly Ser His Ala Gly Asn Lys Leu Ala Met Gln Glu Phe Met
        275                 280                 285

Ile Met Pro Ile Gly Ala Ser Ser Phe Ser Glu Ala Met Arg Met Gly
    290                 295                 300

Ser Glu Ile Tyr His Tyr Leu Lys Ala Glu Ile Lys Lys Arg Tyr Gly
305                 310                 315                 320

Leu Asp Ala Thr Ala Val Gly Asp Glu Gly Gly Phe Ala Pro Asn Ile
                325                 330                 335

Gln Asp Asn Arg Glu Gly Leu Asp Leu Leu Asn Thr Ala Ile Ala Thr
            340                 345                 350

Ala Gly Tyr Thr Gly Lys Val Ala Ile Ala Met Asp Cys Ala Ala Ser
        355                 360                 365

Glu Tyr Tyr Lys Glu Ser Asp Lys Leu Tyr Asp Leu Asp Phe Lys Asn
    370                 375                 380

Pro Asn Ser Asp Lys Thr Gln Trp Lys Thr Gly Asp Gln Met Met Glu
385                 390                 395                 400
```

-continued

```
Ile Tyr Gln Ser Phe Ile Lys Glu Tyr Pro Val Val Ser Ile Glu Asp
                405                 410                 415

Trp Phe Asp Gln Asp Asp Trp Asp Asn Trp Thr Lys Ala Leu Ala Asn
            420                 425                 430

Thr His Ile Gln Ile Val Gly Asp Asp Leu Thr Val Thr Asn Pro Lys
        435                 440                 445

Arg Ile Ala Leu Ala Ala Glu Lys Lys Ala Cys Asn Cys Leu Leu Leu
    450                 455                 460

Lys Val Asn Gln Ile Gly Ser Val Thr Glu Ser Ile Asp Ala Ala Asn
465                 470                 475                 480

Leu Ala Arg Lys Asn Gly Trp Gly Val Met Val Ser His Arg Ser Gly
                485                 490                 495

Glu Thr Glu Asp Thr Phe Ile Ala Asp Leu Val Val Gly Leu Ala Thr
            500                 505                 510

Gly Gln Ile Lys Thr Gly Ala Pro Cys Arg Ser Glu Arg Leu Ala Lys
        515                 520                 525

Tyr Asn Gln Ile Leu Arg Ile Glu Glu Glu Leu Gly Ser Ala Ala Ile
    530                 535                 540

Tyr Ala Gly Gln Lys Phe Arg Asn Pro Gln Ala Gly Ser Ser Gly Lys
545                 550                 555                 560

Phe Thr Asp Ala Asp Phe Lys Glu Gly Ile Lys Pro Tyr Asp Val Leu
                565                 570                 575

Leu Val Lys Phe Tyr Ala Pro Trp Cys Gly His Cys Lys Lys Ile Ala
            580                 585                 590

Pro Glu Phe Glu Lys Ala Ala Thr Lys Leu Leu Gln Asn Asp Pro Pro
        595                 600                 605

Ile His Leu Ala Glu Val Asp Cys Thr Glu Glu Lys Lys Thr Cys Asp
    610                 615                 620

Glu Tyr Gly Val Ser Gly Phe Pro Thr Leu Lys Ile Phe Arg Lys Gly
625                 630                 635                 640

Glu Leu Ala Gln Asp Tyr Asp Gly Pro Arg Val Ala Glu Gly Ile Val
                645                 650                 655

Lys Tyr Met Arg Gly Gln Ala Gly Pro Ser Ala Thr Glu Ile Asn Thr
            660                 665                 670

Gln Gln Glu Phe Glu Lys Met Leu Gln Ala Asp Asp Val Thr Ile Cys
        675                 680                 685

Gly Phe Phe Glu Glu Asn Ser Lys Leu Lys Asp Ser Phe Leu Lys Val
    690                 695                 700

Ala Asp Thr Glu Arg Asp Arg Phe Lys Phe Val Trp Thr Ser Asn Lys
705                 710                 715                 720

Gln Ile Leu Glu Ser Arg Gly Tyr Asn Asp Asp Ile Val Ala Tyr Gln
                725                 730                 735

Pro Lys Lys Phe His Asn Lys Phe Glu Pro Asn Glu Phe Lys Tyr Asp
            740                 745                 750

Gly Asn Tyr Asp Thr Asp Lys Ile Lys Glu Phe Leu Leu His Glu Thr
        755                 760                 765

Asn Gly Leu Val Gly Ile Arg Thr Ala Glu Asn Arg Tyr Gln Tyr Asp
    770                 775                 780

Leu Leu Pro Met Phe Val Val Tyr Gly Lys Val Asp Tyr Glu Leu Asp
785                 790                 795                 800

Pro Lys Gly Ser Asn Tyr Trp Arg Asn Arg Val Leu Met Val Ala Lys
                805                 810                 815

Asp Tyr Lys Arg Lys Ala Asn Phe Ala Met Ser Asn Lys Glu Asp Phe
```

-continued

```
            820                 825                 830

Ser Phe Asp Leu Asp Glu Phe Gly Leu Ala Asn Arg Lys Asp Thr Lys
        835                 840                 845

Pro Leu Val Ala Ala Arg Ser Lys Lys Gly Lys Phe Phe Met Lys Glu
    850                 855                 860

Glu Phe Ser Phe Ser Val Glu Asn Leu Lys Lys Phe Val Glu Asp Val
865                 870                 875                 880

Ile Gly Asp Arg Leu Glu Pro Tyr Met Lys Ser Glu Glu Ala Pro Glu
                885                 890                 895

Asp Gln Gly Asp Val Lys Val Val Val Ala Lys Thr Phe Gln Glu Met
            900                 905                 910

Ile Met Asn Val Glu Lys Asp Val Leu Ile Glu Phe Tyr Ala Pro Trp
        915                 920                 925

Cys Gly His Cys Lys Ala Leu Ala Pro Lys Tyr Asp Glu Leu Gly Gln
    930                 935                 940

Lys Leu Ser Gly Glu Pro Gly Val Val Ile Ala Lys Met Asp Ala Thr
945                 950                 955                 960

Ala Asn Asp Val Pro Pro Pro Phe Gln Val Gln Gly Phe Pro Thr Leu
                965                 970                 975

Tyr Trp Val Pro Lys Asn Lys Lys Asp Lys Pro Glu Pro Tyr Ser Gly
            980                 985                 990

Gly Arg Glu Val Asp Asp Phe Ile  Lys Tyr Ile Ala Lys  His Ala Thr
        995                 1000                1005

Glu Glu  Leu Lys Gly Tyr Lys  Arg Asp Gly Lys Pro  Lys Lys Lys
    1010                1015                1020

Glu Glu  Leu Gly Ser Ser Gly  Thr Asp Lys Leu Glu  Arg Ile Glu
    1025                1030                1035

Glu Glu  Leu Arg Asp Thr Gln  Lys Lys Met Met Gln  Thr Glu Asn
    1040                1045                1050

Asp Leu  Asp Lys Ala Gln Glu  Asp Leu Ala Val Ala  Asn Thr Asn
    1055                1060                1065

Leu Glu  Glu Lys Glu Lys Lys  Val Gln Glu Ala Glu  Ala Glu Val
    1070                1075                1080

Ala Ala  Leu Asn Arg Arg Met  Thr Leu Leu Glu Glu  Glu Leu Glu
    1085                1090                1095

Arg Ala  Glu Glu Arg Leu Lys  Ile Ala Thr Asp Lys  Leu Glu Glu
    1100                1105                1110

Ala Thr  His Thr Ala Asp Glu  Ser Glu Arg Val Arg  Lys Val Met
    1115                1120                1125

Glu Asn  Arg Ser Phe Gln Asp  Glu Glu Arg Ala Asn  Thr Val Glu
    1130                1135                1140

Ser Gln  Leu Lys Glu Ala Gln  Leu Leu Ala Glu Glu  Ala Asp Arg
    1145                1150                1155

Lys Tyr  Asp Glu Val Ala Arg  Lys Leu Ala Met Val  Glu Ala Asp
    1160                1165                1170

Leu Glu  Arg Ala Glu Glu Arg  Ala Glu Ala Gly Glu  Asn Lys Ile
    1175                1180                1185

Val Glu  Leu Glu Glu Glu Leu  Arg Val Val Gly Asn  Asn Leu Lys
    1190                1195                1200

Ser Leu  Glu Val Ser Glu Glu  Lys Ala Leu Gln Arg  Glu Asp Ser
    1205                1210                1215

Tyr Glu  Glu Gln Ile Arg Thr  Val Ser Ala Arg Leu  Lys Glu Ala
    1220                1225                1230
```

Glu Thr Arg Ala Glu Phe Ala Glu Arg Ser Val Gln Lys Leu Gln
1235 1240 1245

Lys Glu Val Asp Arg Leu Glu Asp Glu Leu Val His Glu Lys Glu
1250 1255 1260

Arg Tyr Lys Asn Ile Ser Glu Glu Leu Asp Gln Thr Phe Gln Glu
1265 1270 1275

Leu Ser Gly Tyr Glu Gln Lys Leu Ile Ser Glu Glu Asp Leu
1280 1285 1290

<210> SEQ ID NO 48
<211> LENGTH: 285
<212> TYPE: DNA
<213> ORGANISM: Artificial Sequence
<220> FEATURE:
<223> OTHER INFORMATION: Fat3 segment of Fat3-Enolase-DiTG-Tropomyosin (FEDT) chimera

<400> SEQUENCE: 48
tgctggcaac aatttggatg gttaactcat gacttctgcc atcagcaacc ctcaaagaat 60
cgtgagaaga atgatttcta ctctctaatc tttggcaata ttgtgcaggg cttcagtcga 120
gattggtgga aggagaaaca caacacgcac catgccgcta cgaacattgt aggccaagac 180
ggtgatattg atttggctcc attgctggca ttcgttcctg acgatctcaa gaagtacaaa 240
gcccttttcg aacagttcat ctccaagata atcccctacc agcac 285

<210> SEQ ID NO 49
<211> LENGTH: 1305
<212> TYPE: DNA
<213> ORGANISM: Artificial Sequence
<220> FEATURE:
<223> OTHER INFORMATION: Enolase segment of Fat3 FEDT chimera

<400> SEQUENCE: 49
ccaattacgc gtgttcatgc tcgtcccatt tacgactcca ggggtaatcc taccgtcgag 60
gtcgacttga cgacggagaa gggaatcttc agagccgccg tgccctcggg agcttcgact 120
ggtgtacacg aagctcttga gctcagggac aacgataagg cggtaaatca cggaaaaggt 180
gtgctgcagg cagtcagaaa cgtgaacgag cacatcggac ccgctttggt ggccaagaac 240
ttctgcccta cccaacagcg cgaaatcgac cactttatgc tggaactgga cggtacagaa 300
aacaaggcca agttaggagc caatgccatt ttgggcgtgt cgctggcggt ctgtaaggcc 360
ggcgctgttc acaaaggcgt gcctctgtac aagtacatcg ccgaattagc gggtactggc 420
caagtcgtac tgcccgttcc ggctatgaac gtcatcaacg gaggtagcca tgcgggaaac 480
aaattggcga tgcaggagtt catgatcatg ccgatcggtg cctcgtcctt cagcgaagcc 540
atgcgtatgg gtagcgagat ctaccactac ttgaaggccg aaattaagaa gcgttatgga 600
ctcgacgcta ccgccgtggg tgacgaaggt ggttttgcac cgaacatcca ggacaacaga 660
gaaggtctgg acttgttgaa cactgccata gccactgcgg gatacactgg caaggtagct 720
atagccatgg actgcgcagc atcagagtat tacaaggagt ctgataaact gtacgacctt 780
gacttcaaga atcccaattc cgataagaca cagtggaaaa caggtgatca gatgatggag 840
atttaccagt catttatcaa ggaatacccc gtcgtcagca tagaggattg gttcgaccaa 900
gatgactggg acaattggac aaaagcactg gctaacactc atatccagat cgtgggtgat 960
gacctcactg ttacgaaccc aaagaggatt gctctagcgg cagaaaagaa ggcatgcaac 1020
tgcttgttgc taaaagtgaa ccaaatcgga tcagtcaccg agagcattga tgctgccaat 1080

-continued ctggctcgca agaatggctg gggcgtcatg gtgtctcatc gctctggtga gacagaggac 1140
acattcatcg ctgatctagt tgtgggtttg gctactggac agatcaaaac aggagctcct 1200
tgccgttccg agcgcctagc gaaatacaat cagatcctgc gaattgagga agaattaggt 1260
tcagcagcga tttatgctgg tcaaaagttt cgcaacccgc aagct 1305

<210> SEQ ID NO 50
<211> LENGTH: 1401
<212> TYPE: DNA
<213> ORGANISM: Artificial Sequence
<220> FEATURE:
<223> OTHER INFORMATION: DiTG segment of FEDT chimera

<400> SEQUENCE: 50
aaatttactg acgctgactt caaagagggc ataaagccgt atgacgtgct gttggtaaag 60
ttttatgcgc catggtgtgg tcactgcaaa aagatcgcgc ctgagttcga gaaggccgcg 120
acaaaactct tacagaatga ccctccaatc cacttggctg aggtcgactg taccgaagag 180
aagaagacgt gcgatgaata cggtgtctct ggctttccca cgttgaagat tttccgtaag 240
ggcgaactcg cgcaggacta tgacggccca agggtagctg aaggcattgt gaagtatatg 300
cgcggccaag ccggaccgag tgcaaccgaa atcaatacac agcaagaatt cgaaaagatg 360
ctgcaggccg acgacgtgac tatatgtggt ttcttcgagg agaatagtaa gctcaaagac 420
tcctttctta aggtggcgga caccgagagg gacaggttca aattcgtgtg gacctcaaac 480
aaacagatac tcgagtcccg tggatataac gacgacatcg ttgcatacca accgaagaag 540
ttccataaca agttcgaacc taacgaattc aagtacgacg gtaactacga taccgacaag 600
atcaaagagt tcctgttgca cgaaaccaat ggactcgttg gaatccgtac cgccgaaaat 660
agataccagt acgacctact gccgatgttc gtggtatacg gaaaagtcga ctatgagctc 720
gatcctaagg gatctaacta ttggagaaac cgagtactta tggttgccaa ggattacaaa 780
cgcaaagcta acttcgctat gagcaacaaa gaggacttct cgtttgactt agacgaattc 840
ggtctagcga accgcaaaga caccaagcca ttagtcgctg cacgaagcaa gaaaggcaag 900
ttcttcatga aggaggagtt ctccttcagt gttgagaatc tcaagaaatt cgtcgaggac 960
gttatcggag atagactgga gccttacatg aaatccgagg aagccccaga agatcagggc 1020
gatgtcaaag tcgtagtagc aaagacattt caggagatga ttatgaacgt tgagaaggat 1080
gttcttatcg aattctacgc tccctggtgt ggccactgta aggctctggc ccctaaatac 1140
gacgagctcg gtcagaagtt gagtggtgag cctggagtgg tgatagctaa gatggacgca 1200
accgccaacg acgtgcctcc accattccag gtgcaaggtt ttccaacgct atactgggtc 1260
ccaaagaaca agaaagataa gcccgagcca tattcaggtg gaagggaggt cgacgacttc 1320
atcaaataca tcgcgaaaca cgctaccgaa gagctgaagg gttataaaag agatggcaaa 1380
cccaagaaga aagaggagct g 1401

<210> SEQ ID NO 51
<211> LENGTH: 756
<212> TYPE: DNA
<213> ORGANISM: Artificial Sequence
<220> FEATURE:
<223> OTHER INFORMATION: Tropomyosin segment of FEDT chimera

<400> SEQUENCE: 51
actgacaaac ttgaacgcat cgaggaagaa cttcgcgaca cacagaagaa gatgatgcaa 60

-continued

```
actgagaacg atctcgataa ggcccaagag gatctcgctg tcgctaacac aaacttggaa    120

gaaaaggaga agaaggtgca agaggctgaa gctgaagtgg ctgcactcaa cagacgcatg    180

acgttactcg aggaagagct ggagagggct gaggagcgcc taaagatagc caccgataaa    240

ctcgaggagg caacccatac tgctgatgaa agcgaaagag tccgcaaagt catggagaat    300

cgttccttcc aagatgaaga acgcgcaaac accgtggaaa gccaactgaa agaagcacag    360

ttgctggcag aggaagccga taggaaatat gatgaagttg cgagaaagct ggccatggtt    420

gaggctgatt tagaacgcgc ggaagaacgc gccgaagccg gtgaaaacaa aattgtcgag    480

ctcgaagagg agctgagagt cgtgggcaac aacttgaagt ctctggaggt atcggaggag    540

aaggccctgc agagggaaga ttcctacgag gaacaaattc gtaccgtttc agcacgactt    600

aaggaggcgg aaacacgcgc tgaattcgct gaaaggagtg tgcaaaagct ccagaaagag    660

gtagaccgtc tggaggacga actggtgcac gaaaaggagc gttacaagaa catctcggag    720

gaattagacc aaacctttca ggagctctca ggctac                              756
```

<210> SEQ ID NO 52
<211> LENGTH: 3876
<212> TYPE: DNA
<213> ORGANISM: Artificial Sequence
<220> FEATURE:
<223> OTHER INFORMATION: FEDT Chimera with 5' Murine IgK chain leader
      and 3' C-myc tag

<400> SEQUENCE: 52

```
atggagactg acactctttt gctgtgggta cttctcctct gggttcccgg cagcacaggt     60

gattgctggc aacaatttgg atggttaact catgacttct gccatcagca accctcaaag    120

aatcgtgaga agaatgattt ctactctcta atctttggca atattgtgca gggcttcagt    180

cgagattggt ggaaggagaa acacaacacg caccatgccg ctacgaacat tgtaggccaa    240

gacggtgata ttgatttggc tccattgctg gcattcgttc ctgacgatct caagaagtac    300

aaagcccttt tcgaacagtt catctccaag ataatcccct accagcacgg ttcctctggc    360

ccaattacgc gtgttcatgc tcgtcccatt tacgactcca ggggtaatcc taccgtcgag    420

gtcgacttga cgacggagaa gggaatcttc agagccgccg tgccctcggg agcttcgact    480

ggtgtacacg aagctcttga gctcagggac aacgataagg cggtaaatca cggaaaaggt    540

gtgctgcagg cagtcagaaa cgtgaacgag cacatcggac ccgctttggt ggccaagaac    600

ttctgcccta cccaacagcg cgaaatcgac cactttatgc tggaactgga cggtacagaa    660

aacaaggcca agttaggagc caatgccatt ttgggcgtgt cgctggcggt ctgtaaggcc    720

ggcgctgttc acaaaggcgt gcctctgtac aagtacatcg ccgaattagc gggtactggc    780

caagtcgtac tgcccgttcc ggctatgaac gtcatcaacg gaggtagcca tgcgggaaac    840

aaattggcga tgcaggagtt catgatcatg ccgatcggtg cctcgtcctt cagcgaagcc    900

atgcgtatgg gtagcgagat ctaccactac ttgaaggccg aaattaagaa gcgttatgga    960

ctcgacgcta ccgccgtggg tgacgaaggt ggttttgcac cgaacatcca ggacaacaga   1020

gaaggtctgg acttgttgaa cactgccata gccactgcgg gatacactgg caaggtagct   1080

atagccatgg actgcgcagc atcagagtat tacaaggagt ctgataaact gtacgacctt   1140

gacttcaaga atcccaattc cgataagaca cagtggaaaa caggtgatca gatgatggag   1200

atttaccagt catttatcaa ggaataccccc gtcgtcagca tagaggattg gttcgaccaa   1260

gatgactggg acaattggac aaaagcactg gctaacactc atatccagat cgtgggtgat   1320
```

-continued

```
gacctcactg ttacgaaccc aaagaggatt gctctagcgg cagaaaagaa ggcatgcaac   1380
tgcttgttgc taaaagtgaa ccaaatcgga tcagtcaccg agagcattga tgctgccaat   1440
ctggctcgca agaatggctg gggcgtcatg gtgtctcatc gctctggtga gacagaggac   1500
acattcatcg ctgatctagt tgtgggtttg gctactggac agatcaaaac aggagctcct   1560
tgccgttccg agcgcctagc gaaatacaat cagatcctgc gaattgagga agaattaggt   1620
tcagcagcga tttatgctgg tcaaaagttt cgcaacccgc aagctggctc ttcaggaaaa   1680
tttactgacg ctgacttcaa agagggcata aagccgtatg acgtgctgtt ggtaaagttt   1740
tatgcgccat ggtgtggtca ctgcaaaaag atcgcgcctg agttcgagaa ggccgcgaca   1800
aaactcttac agaatgaccc tccaatccac ttggctgagg tcgactgtac cgaagagaag   1860
aagacgtgcg atgaatacgg tgtctctggc tttcccacgt tgaagatttt ccgtaagggc   1920
gaactcgcgc aggactatga cggcccaagg gtagctgaag gcattgtgaa gtatatgcgc   1980
ggccaagccg gaccgagtgc aaccgaaatc aatacacagc aagaattcga aaagatgctg   2040
caggccgacg acgtgactat atgtggtttc ttcgaggaga atagtaagct caaagactcc   2100
tttcttaagg tggcggacac cgagagggac aggttcaaat tcgtgtggac ctcaaacaaa   2160
cagatactcg agtcccgtgg atataacgac gacatcgttg cataccaacc gaagaagttc   2220
cataacaagt tcgaacctaa cgaattcaag tacgacggta actacgatac cgacaagatc   2280
aaagagttcc tgttgcacga aaccaatgga ctcgttggaa tccgtaccgc cgaaaataga   2340
taccagtacg acctactgcc gatgttcgtg gtatacggaa aagtcgacta tgagctcgat   2400
cctaagggat ctaactattg gagaaaccga gtacttatgg ttgccaagga ttacaaacgc   2460
aaagctaact tcgctatgag caacaaagag gacttctcgt ttgacttaga cgaattcggt   2520
ctagcgaacc gcaaagacac caagccatta gtcgctgcac gaagcaagaa aggcaagttc   2580
ttcatgaagg aggagttctc cttcagtgtt gagaatctca agaaattcgt cgaggacgtt   2640
atcggagata gactggagcc ttacatgaaa tccgaggaag ccccagaaga tcagggcgat   2700
gtcaaagtcg tagtagcaaa gacatttcag gagatgatta tgaacgttga gaaggatgtt   2760
cttatcgaat tctacgctcc ctggtgtggc cactgtaagg ctctggcccc taaatacgac   2820
gagctcggtc agaagttgag tggtgagcct ggagtggtga tagctaagat ggacgcaacc   2880
gccaacgacg tgcctccacc attccaggtg caaggttttc caacgctata ctgggtccca   2940
aagaacaaga aagataagcc cgagccatat tcaggtggaa gggaggtcga cgacttcatc   3000
aaatacatcg cgaaacacgc taccgaagag ctgaagggtt ataaaagaga tggcaaaccc   3060
aagaagaaag aggagctggg ttctagtggt actgacaaac ttgaacgcat cgaggaagaa   3120
cttcgcgaca cacagaagaa gatgatgcaa actgagaacg atctcgataa ggcccaagag   3180
gatctcgctg tcgctaacac aaacttggaa gaaaaggaga agaaggtgca agaggctgaa   3240
gctgaagtgg ctgcactcaa cagacgcatg acgttactcg aggaagagct ggagagggct   3300
gaggagcgcc taaagatagc caccgataaa ctcgaggagg caacccatac tgctgatgaa   3360
agcgaaagag tccgcaaagt catggagaat cgttccttcc aagatgaaga acgcgcaaac   3420
accgtggaaa gccaactgaa agaagcacag ttgctggcag aggaagccga taggaaatat   3480
gatgaagttg cgagaaagct ggccatggtt gaggctgatt tagaacgcgc ggaagaacgc   3540
gccgaagccg gtgaaaacaa aattgtcgag ctcgaagagg agctgagagt cgtgggcaac   3600
aacttgaagt ctctggaggt atcggaggag aaggccctgc agagggaaga ttcctacgag   3660
gaacaaattc gtaccgtttc agcacgactt aaggaggcgg aaacacgcgc tgaattcgct   3720
```

```
gaaaggagtg tgcaaaagct ccagaaagag gtagaccgtc tggaggacga actggtgcac   3780

gaaaaggagc gttacaagaa catctcggag gaattagacc aaacctttca ggagctctca   3840

ggctacgaac agaagctgat cagtgaggaa gatctt                             3876


<210> SEQ ID NO 53
<211> LENGTH: 207
<212> TYPE: PRT
<213> ORGANISM: Artificial Sequence
<220> FEATURE:
<223> OTHER INFORMATION: GST segment of GST-Cathepsin (GC) Chimera

<400> SEQUENCE: 53

Ser Tyr Lys Leu Thr Tyr Phe Pro Ile Arg Gly Leu Ala Glu Pro Ile
1               5                   10                  15

Arg Leu Leu Leu Val Asp Gln Gly Ile Lys Phe Thr Asp Glu His Ile
            20                  25                  30

Pro Lys Asp Asp Phe Val Ser Ile Lys Ser Gln Phe Gln Phe Gly Gln
        35                  40                  45

Leu Pro Cys Phe Tyr Asp Gly Asp Gln Gln Ile Val Gln Ser Gly Ala
    50                  55                  60

Ile Leu Arg His Leu Ala Arg Lys Phe Asn Leu Asn Gly Glu Asn Asn
65                  70                  75                  80

Ala Glu Thr Ser Tyr Val Asp Met Phe Tyr Glu Gly Ile Arg Asp Leu
                85                  90                  95

His Ser Lys Tyr Thr Arg Met Ile Tyr Glu Ala Tyr Glu Thr Gln Lys
            100                 105                 110

Asp Pro Phe Ile Lys Asn Ile Leu Pro Gln Glu Leu Ala Lys Leu Glu
        115                 120                 125

Lys Leu Leu Ala Thr Arg Asp Asn Gly Lys Asn Phe Ile Leu Gly Asp
    130                 135                 140

Lys Ile Ser Phe Ala Asp Tyr Val Leu Phe Glu Glu Leu Asp Val Gln
145                 150                 155                 160

Gln Ile Leu Asp Pro His Cys Leu Glu Lys Phe Pro Leu Leu Lys Ala
                165                 170                 175

Phe His Gln Arg Leu Gly Asp Lys Pro Lys Ile Lys Glu Tyr Cys Ala
            180                 185                 190

Lys Arg Asn Ala Ser Lys Met Pro Val Asn Gly Asn Gly Lys Gln
        195                 200                 205


<210> SEQ ID NO 54
<211> LENGTH: 515
<212> TYPE: PRT
<213> ORGANISM: Artificial Sequence
<220> FEATURE:
<223> OTHER INFORMATION: Cathepsin segment of GC Chimera

<400> SEQUENCE: 54

Thr Arg Arg Ser Phe Pro Thr Ile Ala Phe His Ser Phe Phe Leu Val
1               5                   10                  15

Ser Phe Tyr Pro Ser Leu Phe Ser Asp Arg Asn Gly Gly Arg Gly Arg
            20                  25                  30

Gly Arg Asn Lys Val Met Arg Glu Lys Lys Arg Gly Arg Glu Met Glu
        35                  40                  45

Arg Asn Val Ser Val Ile Leu Lys Tyr Phe Leu Ser Phe Ile Ile Leu
    50                  55                  60

His Leu Cys Phe Leu Ser Met Val Val Ile Gly Arg Gly His His Ala
```

```
65                  70                  75                  80

Met Thr Phe Thr Thr Ile Ala Thr Thr Phe Leu Ser Val Leu Thr Ile
                85                  90                  95

Ile Thr Leu Cys Asn Lys His Thr Ile Ala Ile Ala Asp Glu Lys Asp
            100                 105                 110

His Leu Thr Arg Ile Met Leu His Lys Gln Asp Ser Ile Arg Thr His
        115                 120                 125

Leu Ile Lys Ala Gly Ser Trp Glu Ala Tyr Ser Asp Leu Leu Asn Phe
    130                 135                 140

Gln Ile Gln Arg Lys Lys Ile Gln His Lys Ile Glu Ser Asp Leu Asp
145                 150                 155                 160

Ser Ala Ser Lys Ser Asp Ala Ile Asp Glu Thr Asp Glu Val Leu Lys
                165                 170                 175

Asn Tyr Met Asp Ala Gln Tyr Tyr Gly Gln Ile Ser Ile Gly Thr Pro
            180                 185                 190

Pro Gln Asn Phe Ser Val Ile Phe Asp Thr Gly Ser Ser Asn Leu Trp
        195                 200                 205

Val Pro Ser Ile Lys Cys Pro Phe Leu Asp Ile Ala Cys Leu Leu His
    210                 215                 220

Asn Lys Tyr Lys Gly Thr Glu Ser Lys Thr Tyr Lys Pro Asp Gly Arg
225                 230                 235                 240

Lys Ile Gln Ile Gln Tyr Gly Arg Gly Ser Met Lys Gly Phe Ile Ser
                245                 250                 255

Leu Asp Thr Val Cys Ile Ala Asp Ile Cys Val Lys Asn Gln Pro Phe
            260                 265                 270

Ala Glu Ala Ile Ala Glu Pro Gly Ala Thr Phe Val Met Ala Lys Phe
        275                 280                 285

Asp Gly Ile Leu Gly Met Ala Phe Pro Glu Ile Ala Val Leu Glu Leu
    290                 295                 300

Ser Pro Val Phe His Thr Met Ile Asn Gln Lys Val Leu Gln Gln Pro
305                 310                 315                 320

Val Phe Ala Phe Trp Leu Asp Arg Asn Pro Asn Asp Glu Ile Gly Gly
                325                 330                 335

Glu Ile Thr Leu Gly Gly Ile Asp Met Asn Arg Phe Val Ser Pro Ile
            340                 345                 350

Thr Tyr Thr Pro Ile Ser Arg Leu Gly Tyr Trp Gln Phe Lys Met Asp
        355                 360                 365

Ser Ile Gln Gly Asp Asn Glu Ala Ile Gly Cys Ala Lys Gly Cys Gln
    370                 375                 380

Ala Ile Ala Asp Thr Gly Thr Ser Leu Ile Ala Gly Pro Lys Ser Gln
385                 390                 395                 400

Val Glu Lys Ile Gln Gln Tyr Ile Gly Ala Glu Tyr Val Phe Ala Gly
                405                 410                 415

Glu Tyr Ile Ile Pro Cys Tyr Lys Val Ser Ser Leu Pro Glu Ile Lys
            420                 425                 430

Phe Val Ile Ala Gly Lys Ser Tyr Ala Leu Lys Gly Ser Asp Tyr Val
        435                 440                 445

Leu Asn Val Thr Ser Lys Gly Lys Ser Ile Cys Leu Ser Gly Phe Met
    450                 455                 460

Gly Ile Asp Leu Pro Glu Arg Leu Gly Glu Leu Trp Ile Leu Gly Asp
465                 470                 475                 480

Val Phe Ile Gly Arg Tyr Tyr Thr Val Phe Asp Val Gly Asn Ala Gln
                485                 490                 495
```

```
Ile Gly Phe Ala Gln Ala Arg Asp Ser Lys Gly Lys Pro Val Gly Lys
            500                 505                 510

Arg Val Asn
        515


<210> SEQ ID NO 55
<211> LENGTH: 757
<212> TYPE: PRT
<213> ORGANISM: Artificial Sequence
<220> FEATURE:
<223> OTHER INFORMATION: GC Chimera with 5' Murine IgK chain leader and
      3' C-myc tag

<400> SEQUENCE: 55

Met Glu Thr Asp Thr Leu Leu Leu Trp Val Leu Leu Leu Trp Val Pro
1               5                   10                  15

Gly Ser Thr Gly Asp Ser Tyr Lys Leu Thr Tyr Phe Pro Ile Arg Gly
            20                  25                  30

Leu Ala Glu Pro Ile Arg Leu Leu Leu Val Asp Gln Gly Ile Lys Phe
        35                  40                  45

Thr Asp Glu His Ile Pro Lys Asp Asp Phe Val Ser Ile Lys Ser Gln
    50                  55                  60

Phe Gln Phe Gly Gln Leu Pro Cys Phe Tyr Asp Gly Asp Gln Gln Ile
65                  70                  75                  80

Val Gln Ser Gly Ala Ile Leu Arg His Leu Ala Arg Lys Phe Asn Leu
                85                  90                  95

Asn Gly Glu Asn Asn Ala Glu Thr Ser Tyr Val Asp Met Phe Tyr Glu
            100                 105                 110

Gly Ile Arg Asp Leu His Ser Lys Tyr Thr Arg Met Ile Tyr Glu Ala
        115                 120                 125

Tyr Glu Thr Gln Lys Asp Pro Phe Ile Lys Asn Ile Leu Pro Gln Glu
    130                 135                 140

Leu Ala Lys Leu Glu Lys Leu Leu Ala Thr Arg Asp Asn Gly Lys Asn
145                 150                 155                 160

Phe Ile Leu Gly Asp Lys Ile Ser Phe Ala Asp Tyr Val Leu Phe Glu
                165                 170                 175

Glu Leu Asp Val Gln Gln Ile Leu Asp Pro His Cys Leu Glu Lys Phe
            180                 185                 190

Pro Leu Leu Lys Ala Phe His Gln Arg Leu Gly Asp Lys Pro Lys Ile
        195                 200                 205

Lys Glu Tyr Cys Ala Lys Arg Asn Ala Ser Lys Met Pro Val Asn Gly
    210                 215                 220

Asn Gly Lys Gln Gly Ser Ser Gly Thr Arg Arg Ser Phe Pro Thr Ile
225                 230                 235                 240

Ala Phe His Ser Phe Phe Leu Val Ser Phe Tyr Pro Ser Leu Phe Ser
                245                 250                 255

Asp Arg Asn Gly Gly Arg Gly Arg Gly Arg Asn Lys Val Met Arg Glu
            260                 265                 270

Lys Lys Arg Gly Arg Glu Met Glu Arg Asn Val Ser Val Ile Leu Lys
        275                 280                 285

Tyr Phe Leu Ser Phe Ile Ile Leu His Leu Cys Phe Leu Ser Met Val
    290                 295                 300

Val Ile Gly Arg Gly His His Ala Met Thr Phe Thr Thr Ile Ala Thr
305                 310                 315                 320

Thr Phe Leu Ser Val Leu Thr Ile Ile Thr Leu Cys Asn Lys His Thr
```

```
                325                 330                 335

Ile Ala Ile Ala Asp Glu Lys Asp His Leu Thr Arg Ile Met Leu His
            340                 345                 350

Lys Gln Asp Ser Ile Arg Thr His Leu Ile Lys Ala Gly Ser Trp Glu
        355                 360                 365

Ala Tyr Ser Asp Leu Leu Asn Phe Gln Ile Gln Arg Lys Lys Ile Gln
    370                 375                 380

His Lys Ile Glu Ser Asp Leu Asp Ser Ala Ser Lys Ser Asp Ala Ile
385                 390                 395                 400

Asp Glu Thr Asp Glu Val Leu Lys Asn Tyr Met Asp Ala Gln Tyr Tyr
                405                 410                 415

Gly Gln Ile Ser Ile Gly Thr Pro Pro Gln Asn Phe Ser Val Ile Phe
            420                 425                 430

Asp Thr Gly Ser Ser Asn Leu Trp Val Pro Ser Ile Lys Cys Pro Phe
        435                 440                 445

Leu Asp Ile Ala Cys Leu Leu His Asn Lys Tyr Lys Gly Thr Glu Ser
    450                 455                 460

Lys Thr Tyr Lys Pro Asp Gly Arg Lys Ile Gln Ile Gln Tyr Gly Arg
465                 470                 475                 480

Gly Ser Met Lys Gly Phe Ile Ser Leu Asp Thr Val Cys Ile Ala Asp
                485                 490                 495

Ile Cys Val Lys Asn Gln Pro Phe Ala Glu Ala Ile Ala Glu Pro Gly
            500                 505                 510

Ala Thr Phe Val Met Ala Lys Phe Asp Gly Ile Leu Gly Met Ala Phe
        515                 520                 525

Pro Glu Ile Ala Val Leu Glu Leu Ser Pro Val Phe His Thr Met Ile
    530                 535                 540

Asn Gln Lys Val Leu Gln Gln Pro Val Phe Ala Phe Trp Leu Asp Arg
545                 550                 555                 560

Asn Pro Asn Asp Glu Ile Gly Gly Glu Ile Thr Leu Gly Gly Ile Asp
                565                 570                 575

Met Asn Arg Phe Val Ser Pro Ile Thr Tyr Thr Pro Ile Ser Arg Leu
            580                 585                 590

Gly Tyr Trp Gln Phe Lys Met Asp Ser Ile Gln Gly Asp Asn Glu Ala
        595                 600                 605

Ile Gly Cys Ala Lys Gly Cys Gln Ala Ile Ala Asp Thr Gly Thr Ser
    610                 615                 620

Leu Ile Ala Gly Pro Lys Ser Gln Val Glu Lys Ile Gln Gln Tyr Ile
625                 630                 635                 640

Gly Ala Glu Tyr Val Phe Ala Gly Glu Tyr Ile Ile Pro Cys Tyr Lys
                645                 650                 655

Val Ser Ser Leu Pro Glu Ile Lys Phe Val Ile Ala Gly Lys Ser Tyr
            660                 665                 670

Ala Leu Lys Gly Ser Asp Tyr Val Leu Asn Val Thr Ser Lys Gly Lys
        675                 680                 685

Ser Ile Cys Leu Ser Gly Phe Met Gly Ile Asp Leu Pro Glu Arg Leu
    690                 695                 700

Gly Glu Leu Trp Ile Leu Gly Asp Val Phe Ile Gly Arg Tyr Tyr Thr
705                 710                 715                 720

Val Phe Asp Val Gly Asn Ala Gln Ile Gly Phe Ala Gln Ala Arg Asp
                725                 730                 735

Ser Lys Gly Lys Pro Val Gly Lys Arg Val Asn Glu Gln Lys Leu Ile
            740                 745                 750
```

Ser Glu Glu Asp Leu
755

<210> SEQ ID NO 56
<211> LENGTH: 621
<212> TYPE: DNA
<213> ORGANISM: Artificial Sequence
<220> FEATURE:
<223> OTHER INFORMATION: GST segment of GST-Cathepsin (GC) Chimera

<400> SEQUENCE: 56
tcctacaagt taacctactt ccccataaga ggcctggccg aaccaatcag actgctcttg 60
gtcgaccagg gtatcaaatt cacggatgag cacatcccta aagacgattt cgtcagcatc 120
aagagccagt ttcagttcgg tcaactcccc tgcttctatg acggcgacca acagatagtg 180
caaagtggcg ctattctgcg tcacttggct cgaaagttca acctcaacgg tgagaacaac 240
gccgagactt catatgtgga catgttctac gagggtatac gcgacttgca ttccaaatac 300
acccgtatga tctatgaagc ctacgagaca cagaaagacc cgttcatcaa gaacatactg 360
cctcaagagc ttgcaaagct ggagaaacta ttagccacac gagataatgg caagaacttc 420
atcttaggtg acaaaatctc cttcgcggat tacgttctat tcgaggagct cgatgtccag 480
cagatcctag acccacattg tctggaaaag ttccccttgt taaaggcttt tcaccagaga 540
ctgggcgaca aacccaagat caaggaatat tgcgccaaaa ggaatgcatc caagatgcct 600
gtaaatggca atggtaagca g 621

<210> SEQ ID NO 57
<211> LENGTH: 1545
<212> TYPE: DNA
<213> ORGANISM: Artificial Sequence
<220> FEATURE:
<223> OTHER INFORMATION: Cathepsin segment of GC Chimera

<400> SEQUENCE: 57
acccgcagat cttttcccac gatcgccttt cactctttct ttctagtgtc gttttaccca 60
agtctgtttt cggatcgcaa cggtggacgc ggaaggggtc gcaacaaagt gatgagggag 120
aagaagagag gacgtgagat ggaacgcaat gtaagtgtca ttctcaaata cttcctttcc 180
ttcattatcc tgcatctgtg ctttctctca atggtcgtta ttggccgagg ccatcacgca 240
atgacgttca ctactatcgc aaccaccttc ctgtctgtgc ttacaatcat cactctctgc 300
aacaagcaca ctatagctat cgcggatgaa aaggaccact tgactcgcat catgctgcat 360
aagcaggatt ccattcgcac acacctgata aaagcgggat catgggaagc ttattcagac 420
ctgttgaact tccaaatcca gcgtaagaag attcagcaca aaatcgagtc cgacttagac 480
agtgcatcaa agtctgacgc cattgatgaa acagacgagg tccttaagaa ttacatggat 540
gctcagtact acggccagat aagcatcggt acccctccac aaaacttctc cgtcatcttc 600
gacacaggct catctaacct ttgggtcccg tctattaagt gcccgttctt ggatatcgcc 660
tgtttgttgc acaacaaata caagggaacg gaatcaaaga catacaagcc tgacggtcgt 720
aaaatccaga ttcaatacgg tcgtggttcg atgaagggct tcatttcgct tgacaccgtg 780
tgtatagctg atatctgcgt caagaaccaa cctttcgccg aagctatagc tgaacctggt 840
gcgactttcg taatggcgaa attcgacggc atcctcggta tggcattccc tgagattgct 900
gtactggaac taagcccagt attccatacc atgattaacc aaaaggtcct ccaacagccg 960
gtattcgcgt tttggctgga cagaaaccca aacgatgaga ttggcggaga aatcactttg 1020

```
ggcggaatcg acatgaatcg ctttgtttct ccgataacct acactcctat ctcgcgtcta   1080

ggatattggc agttcaagat ggactctatc caaggcgata acgaggctat cggttgtgcc   1140

aagggttgtc aggccattgc tgacacaggt actagcctga ttgctggccc caagagccaa   1200

gttgagaaaa ttcagcaata tatcggagcc gaatacgtgt ttgcaggaga atacatcatt   1260

ccctgctaca aggttagcag tttgcccgag atcaaattcg ttatcgccgg taaatcgtac   1320

gcacttaagg gttcagacta tgtgttgaat gtgacgagta agggaaaatc catctgcctc   1380

tcaggcttca tgggtataga tctgccagag aggctgggag agctctggat cttgggagat   1440

gtgttcattg gacgctacta caccgttttc gacgttggta atgcgcaaat tggatttgct   1500

caggctaggg atagtaaggg caaacccgtg ggtaagaggg tgaac                  1545
```

<210> SEQ ID NO 58
<211> LENGTH: 2271
<212> TYPE: DNA
<213> ORGANISM: Artificial Sequence
<220> FEATURE:
<223> OTHER INFORMATION: GC Chimera with 5' Murine IgK chain leader and 3' C-myc tag

<400> SEQUENCE: 58

```
atggaaacgg ataccttatt actctgggtg ctcttgctct gggtcccagg tagcaccgga     60

gactcctaca agttaaccta cttccccata agaggcctgg ccgaaccaat cagactgctc    120

ttggtcgacc agggtatcaa attcacggat gagcacatcc ctaaagacga tttcgtcagc    180

atcaagagcc agtttcagtt cggtcaactc ccctgcttct atgacggcga ccaacagata    240

gtgcaaagtg gcgctattct gcgtcacttg gctcgaaagt tcaacctcaa cggtgagaac    300

aacgccgaga cttcatatgt ggacatgttc tacgagggta tacgcgactt gcattccaaa    360

tacacccgta tgatctatga agcctacgag acacagaaag acccgttcat caagaacata    420

ctgcctcaag agcttgcaaa gctggagaaa ctattagcca cacgagataa tggcaagaac    480

ttcatcttag gtgacaaaat ctccttcgcg gattacgttc tattcgagga gctcgatgtc    540

cagcagatcc tagacccaca ttgtctggaa aagttcccct tgttaaaggc ttttcaccag    600

agactgggcg acaaacccaa gatcaaggaa tattgcgcca aaaggaatgc atccaagatg    660

cctgtaaatg gcaatggtaa gcagggaagc tctggtaccc gcagatcttt tcccacgatc    720

gcctttcact ctttctttct agtgtcgttt tacccaagtc tgttttcgga tcgcaacggt    780

ggacgcggaa ggggtcgcaa caaagtgatg agggagaaga agagaggacg tgagatggaa    840

cgcaatgtaa gtgtcattct caaatacttc ctttccttca ttatcctgca tctgtgcttt    900

ctctcaatgg tcgttattgg ccgaggccat cacgcaatga cgttcactac tatcgcaacc    960

accttcctgt ctgtgcttac aatcatcact ctctgcaaca agcacactat agctatcgcg   1020

gatgaaaagg accacttgac tcgcatcatg ctgcataagc aggattccat tcgcacacac   1080

ctgataaaag cgggatcatg ggaagcttat tcagacctgt tgaacttcca aatccagcgt   1140

aagaagattc agcacaaaat cgagtccgac ttagacagtg catcaaagtc tgacgccatt   1200

gatgaaacag acgaggtcct taagaattac atggatgctc agtactacgg ccagataagc   1260

atcggtaccc ctccacaaaa cttctccgtc atcttcgaca caggctcatc taacctttgg   1320

gtcccgtcta ttaagtgccc gttcttggat atcgcctgtt tgttgcacaa caaatacaag   1380

ggaacggaat caaagacata caagcctgac ggtcgtaaaa tccagattca atacggtcgt   1440

ggttcgatga agggcttcat ttcgcttgac accgtgtgta tagctgatat ctgcgtcaag   1500
```

-continued

```
aaccaacctt tcgccgaagc tatagctgaa cctggtgcga ctttcgtaat ggcgaaattc   1560

gacggcatcc tcggtatggc attccctgag attgctgtac tggaactaag cccagtattc   1620

cataccatga ttaaccaaaa ggtcctccaa cagccggtat tcgcgttttg gctggacaga   1680

aacccaaacg atgagattgg cggagaaatc actttgggcg gaatcgacat gaatcgcttt   1740

gtttctccga taacctacac tcctatctcg cgtctaggat attggcagtt caagatggac   1800

tctatccaag gcgataacga ggctatcggt tgtgccaagg gttgtcaggc cattgctgac   1860

acaggtacta gcctgattgc tggccccaag agccaagttg agaaaattca gcaatatatc   1920

ggagccgaat acgtgtttgc aggagaatac atcattccct gctacaaggt tagcagtttg   1980

cccgagatca aattcgttat cgccggtaaa tcgtacgcac ttaagggttc agactatgtg   2040

ttgaatgtga cgagtaaggg aaaatccatc tgcctctcag gcttcatggg tatagatctg   2100

ccagagaggc tgggagagct ctggatcttg ggagatgtgt tcattggacg ctactacacc   2160

gttttcgacg ttggtaatgc gcaaattgga tttgctcagg ctagggatag taagggcaaa   2220

cccgtgggta agagggtgaa cgaacaaaag ctgatttccg aagaggacct t            2271
```